(12) United States Patent
Kataoka et al.

(10) Patent No.: US 9,937,263 B2
(45) Date of Patent: Apr. 10, 2018

(54) CARRIER FOR USE IN DELIVERING DRUG, CONJUGATE, COMPOSITION COMPRISING SAME, AND METHOD FOR ADMINISTRATING SAME

(71) Applicants: THE UNIVERSITY OF TOKYO, Bunkyo-ku (JP); NATIONAL UNIVERSITY CORPORATION TOKYO MEDICAL AND DENTAL UNIVERSITY, Bunkyo-ku (JP)

(72) Inventors: Kazunori Kataoka, Tokyo (JP); Yasutaka Anraku, Tokyo (JP); Nobuhiro Nishiyama, Tokyo (JP); Kanjiro Miyata, Tokyo (JP); Takehiko Ishii, Tokyo (JP); Yu Matsumoto, Tokyo (JP); Yu Fukusato, Tokyo (JP); Akihiro Mizoguchi, Tokyo (JP); Takanori Yokota, Tokyo (JP); Hiroya Kuwahara, Tokyo (JP); Kazutaka Nishina, Tokyo (JP); Hidehiro Mizusawa, Tokyo (JP)

(73) Assignees: THE UNIVERSITY OF TOKYO, Bunkyo-ku (JP); NATIONAL UNIVERSITY CORPORATION TOKYO MEDICAL AND DENTAL UNIVERSITY, Bunkyo-ku (JP)

( * ) Notice: Subject to any disclaimer, the term of this patent is extended or adjusted under 35 U.S.C. 154(b) by 0 days.

(21) Appl. No.: 15/038,374

(22) PCT Filed: Nov. 21, 2014

(86) PCT No.: PCT/JP2014/005856
§ 371 (c)(1),
(2) Date: May 20, 2016

(87) PCT Pub. No.: WO2015/075942
PCT Pub. Date: May 28, 2015

(65) Prior Publication Data
US 2016/0287714 A1    Oct. 6, 2016

(30) Foreign Application Priority Data
Nov. 22, 2013 (JP) ................................ 2013-242347
May 8, 2014 (JP) ................................ 2014-096935

(51) Int. Cl.
*A61K 9/127* (2006.01)
*A61K 47/48* (2006.01)
(Continued)

(52) U.S. Cl.
CPC ...... *A61K 47/48092* (2013.01); *A61K 9/0019* (2013.01); *A61K 9/127* (2013.01);
(Continued)

(58) Field of Classification Search
None
See application file for complete search history.

(56) References Cited

U.S. PATENT DOCUMENTS

2013/0202711 A1    8/2013    Kataoka et al.

FOREIGN PATENT DOCUMENTS

WO    2007/068429 A1    6/2007
WO    2011/145745 A1    11/2011

OTHER PUBLICATIONS

Qu et al., Eur. J. Med. Chem., 2014, vol. 72, pp. 110-118.*
(Continued)

*Primary Examiner* — Brian Gulledge
(74) *Attorney, Agent, or Firm* — Oblon, McClelland, Maier & Neustadt, L.L.P.

(57) ABSTRACT

The present invention provides a vesicle, a conjugate, a composition comprising the vesicle or the conjugate, for use in delivering a drug to the brain, and a method for admin-
(Continued)

istering the same. The composition of the present invention is a composition for administration to a subject according to a dosing regimen, comprising a carrier for drug delivery, wherein the dosing regimen comprises administering the composition to a subject who has been fasted or caused to have hypoglycemia and inducing an increase in blood glucose level in the subject, and the carrier is modified at the outer surface thereof with a GLUT1 ligand.

24 Claims, 15 Drawing Sheets

(51) Int. Cl.

| | | |
|---|---|---|
| *A61K 31/7088* | (2006.01) | |
| *B01J 13/02* | (2006.01) | |
| *C08G 81/00* | (2006.01) | |
| *C08G 69/10* | (2006.01) | |
| *C08G 69/40* | (2006.01) | |
| *A61K 9/00* | (2006.01) | |
| *A61K 39/44* | (2006.01) | |
| *A61K 47/60* | (2017.01) | |
| *A61K 47/54* | (2017.01) | |
| *A61K 47/64* | (2017.01) | |
| *A61K 47/69* | (2017.01) | |
| *A61K 39/00* | (2006.01) | |

(52) U.S. Cl.
CPC .......... *A61K 31/7088* (2013.01); *A61K 39/44* (2013.01); *A61K 47/543* (2017.08); *A61K 47/549* (2017.08); *A61K 47/554* (2017.08); *A61K 47/60* (2017.08); *A61K 47/645* (2017.08); *A61K 47/6905* (2017.08); *A61K 47/6911* (2017.08); *B01J 13/02* (2013.01); *C08G 69/10* (2013.01); *C08G 69/40* (2013.01); *C08G 81/00* (2013.01); *A61K 2039/505* (2013.01); *A61K 2039/54* (2013.01); *A61K 2039/545* (2013.01); *A61K 2039/6093* (2013.01)

(56) References Cited

OTHER PUBLICATIONS

Patient Information Leaflet, "Questions and Answers About Taxotere Injection Concentrate", 2004, pp. 1-35.*
Safdie et al., Aging (Albany NY), 2009, 1(12), pp. 1-20.*
NCI, "Eating Hints: Before, During, and After Cancer Treatment", 2011, pp. 1-68.*
Boyi Qu, et al., "Design, synthesis and biological evaluation of multivalent glucosides with high affinity as ligands for brain targeting liposomes", European Journal of Medicinal Chemistry, vol. 72, pp. 110-118, (Nov. 20, 2013).
Wataru Kawamura, et al., Construction of Size-Tunable and Ligand Introduction Rate-Adjustable Polyion Complex Vesicles (PICsomes) and Functional Evaluation thereof, Polymer Preprints, vol. 62, No. 2, 10 pages, (Aug. 28, 2013), (with English Translation).
Ian A. Simpson, et al., "Blood-Brain Barrier Glucose Transporter: Effects of Hypo- and Hyperglycemia Revisited", Journal of Neurochemistry, vol. 72, pp. 238-247, (1999).
International Search Report dated Feb. 24, 2015 in PCT/JP14/005856 Filed Nov. 21, 2014.
Extended Search Report dated Sep. 8, 2017 in European Patent Application No. 14863728.3.
Fulan Xie, et al., "Investigation of glucose-modified liposomes using polyethylene glycols with different chain lengths as the linkers for brain targeting", International Journal of Nanomedicine, 2012, XP55352405, pp. 163-175.
Fan Lei, et al., "Design, synthesis and preliminary bio-evaluation of glucose-cholesterol derivatives as ligands for brain targeting liposomes", Chines Chemical Letters, vol. 22, No. 7, 2011, XP002705344, pp. 831-834.
Christine Dufes, et al., "Glucose-targeted niosomes deliver vasoactive intestinal peptide (VIP) to the brain", International Journal of Pharmaceutics, vol. 285, No. 1-2, 2004, XP004602818, pp. 77-85.
Christine Dufes, et al., "Niosomes and Polymeric Chitosan Based Vesicles Bearing Transferrin and Glucose Ligands for Drug Targeting", Pharmaceutical Research, vol. 17, No. 10, 2000, XP 55399377, pp. 1250-1258.
Luca Constantino, et al., "Nanoparticulate drug carriers based on hybrid poly(D, L-lactide-co-glycoolide)-Dendron structures", Biomaterials, vol. 27, No. 26, 2006, XP027951263, pp. 4635-4645.

\* cited by examiner

A 0 min   35min   70min   80min   90min

B

A

Glc(6)-PEG-PAsp(TEP)-Chol

+

Chol-siRNA-Cy5

Stirring and mixing →

80 nm

Glc(6)-siRNA micelle

B

CARRIER FOR USE IN DELIVERING DRUG, CONJUGATE, COMPOSITION COMPRISING SAME, AND METHOD FOR ADMINISTRATING SAME

CROSS REFERENCE TO RELATED APPLICATIONS

The present application claims the benefits of the priorities of Japanese Patent Application Nos. 2013-242347 (filed on Nov. 22, 2013) and 2014-96935 (filed on May 8, 2014), the contents of which are incorporated herein by reference in their entirety.

TECHNICAL FIELD

The present invention relates to a carrier for use in delivering a drug, a conjugate, a composition comprising the carrier or the conjugate, a method for producing the same, and a method for administering the same.

BACKGROUND ART

The blood-brain barrier, which restricts the exchange of materials, is known to exist between the blood and the brain. This is presumably based on events in which: cerebrovascular endothelial cells form tight junctions with very narrow intercellular gaps; and the cells themselves perform the selective uptake and excretion of materials.

The blood-brain barrier has high penetration selectivity, which rarely permits materials, except for some materials (e.g., alcohols, caffeine, nicotine, and glucose), to cross the blood-brain barrier. This makes it difficult to treat brain diseases with brain therapeutic drugs, to diagnose brain diseases with brain diagnostic drugs, or to image the brain with contrast media.

A technique of delivering antibodies to the brain has been developed through the use of the property of glucose of crossing the blood-brain barrier (Patent Literature 1). This technique, however, merely glycosylates antibodies and exhibits only limited effects.

CITATION LIST

Patent Literature

Patent Literature 1: WO2007/068429

SUMMARY OF INVENTION

The present invention provides a carrier for delivering a drug, a conjugate, a composition comprising the carrier or the conjugate, and a method for administering the same.

The present inventors have found that a vesicle such as a micelle can be delivered very efficiently to the brain by administering the vesicle modified at the outer surface thereof with glucose to a subject who has been caused to have hypoglycemia and then raising the blood glucose level. The present invention is based on this finding.

Specifically, the present invention provides the following aspects:
(1) A composition for administration to a subject according to a dosing regimen, comprising a carrier for use in delivering a drug, wherein
  the dosing regimen involves administering the composition to a subject who has been fasted or caused to have hypoglycemia and inducing an increase in blood glucose level in the subject, and
  the carrier is modified at the outer surface thereof with a GLUT1 ligand.
(2) A composition for administration to a subject according to a dosing regimen comprising a conjugate of a drug and a GLUT1 ligand, wherein
  the dosing regimen involves administering the composition to a subject who has been fasted or caused to have hypoglycemia and inducing an increase in blood glucose level in the subject.
(3) The composition according to (1) or (2), for use in delivering the drug to the brain.
(4) The composition according to (1) or (2), for use in permeating the drug across the blood-brain barrier.
(5) The composition according to (1) or (2), for use in permeating the drug across the blood-nerve barrier, the blood-retina barrier, or the blood-cerebrospinal fluid barrier.
(6) The composition according to (1) or (2), for use in delivering the drug to a cerebrovascular endothelial cell.
(7) The composition according to any of (1) to (6), wherein the increase in blood glucose level is induced by glucose administration.
(8) The composition according to (7), wherein the composition is administered concurrently with or before the administration of glucose.
(9) The composition according to any of (1) to (8), wherein the composition is administered in the form of an intravenous infusion, and the infusion administration is continued for 10 minutes or longer.
(10) The composition according to any of (1) and (3) to (9), wherein the carrier is a vesicle, and 10 to 40% by mol of a polymer constituting the vesicle is modified with the GLUT1 ligand.
(11) The composition according to any of (1) and (3) to (9), wherein the carrier is a vesicle, and 40 to 100% by mol of a polymer constituting the vesicle is modified with the GLUT1 ligand.
(12) The composition according to any of (1) and (3) to (11), wherein the carrier incorporates the drug to be delivered.
(13) The composition according to any of (1) and (3) to (12), wherein the carrier is a vesicle, and the vesicle is a vesicle having a diameter of 400 nm or smaller.
(14) The composition according to any of (2) to (9), wherein the conjugate comprises the drug and the GLUT1 ligand linked via a linker.
(15) The composition according to any of (1) to (14), wherein the GLUT1 ligand is glucose.
(16) The composition according to any of (1) to (15), wherein the drug is at least one drug selected from a biologically active substance, an antibody, a nucleic acid, a biocompatible fluorescent dye, and a contrast medium.
(17) A conjugate of one molecule of a GLUT1 ligand and one molecule of a polymer, wherein the conjugate is capable of forming a vesicle such that the GLUT1 ligand is exposed on the surface of the vesicle.
(18) The conjugate according to (17), wherein the GLUT1 ligand is glucose.
(19) The conjugate according to (18), wherein the glucose is conjugated via carbon at position 6 thereof with the polymer.
(20) The conjugate according to (19) or a pharmaceutically acceptable salt thereof, wherein the conjugate is represented by the following formula (I), (II), (III), or (XVI):

[Formula 1]

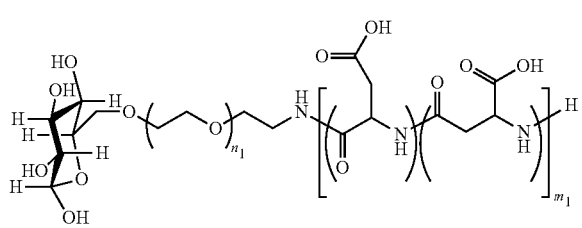

wherein $n_1$ and $m_1$ each represent an integer of 5 to 20,000,

[Formula 2]

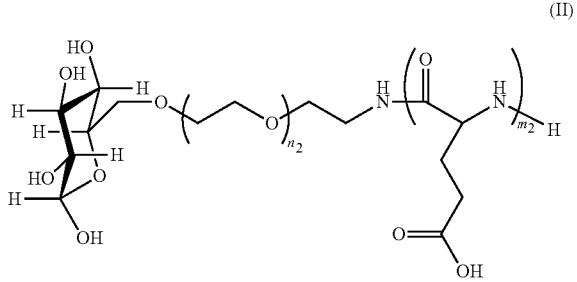

wherein $n_2$ and $m_2$ each represent an integer of 5 to 20,000,

[Formula 3]

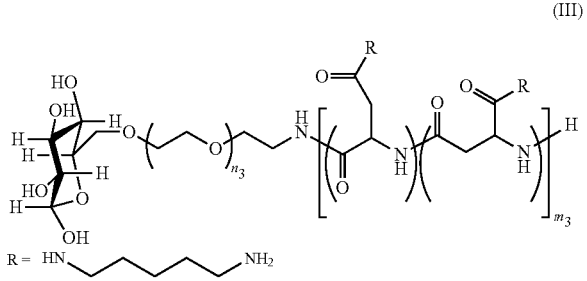

wherein $n_3$ and $m_3$ each represent an integer of 5 to 20,000, and

[Formula 4]

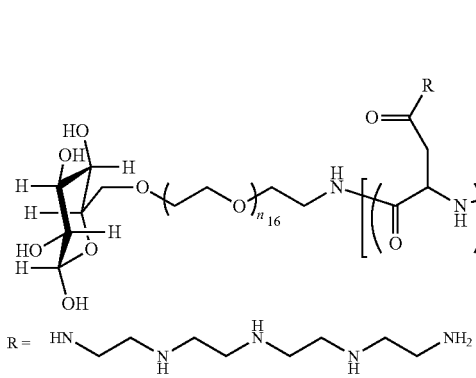
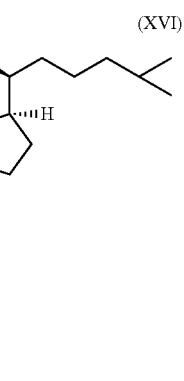

wherein $n_{16}$ represents an integer of 5 to 20,000, and $m_{16}$ represents an integer of 2 to 5,000.

(21) A vesicle for drug delivery comprising a conjugate according to any of (17) to (20), wherein
the conjugate accounts for 10 to 40% by mol of all polymers constituting the vesicle.

(22) A vesicle for drug delivery comprising a conjugate according to any of (17) to (20), wherein
the conjugate accounts for 40 to 100% by mol of all polymers constituting the vesicle.

(23) Use of a GLUT1 ligand for producing a composition according to any of (1) to (16) or a vesicle according to (21) or (22).

BRIEF DESCRIPTION OF DRAWINGS

FIG. 7A shows the siRNA micelle and a preparation method thereof, and FIG. 7B shows changes in the amount of the siRNA micelle accumulated in the brain.

DETAILED DESCRIPTION OF INVENTION

Figure 1:
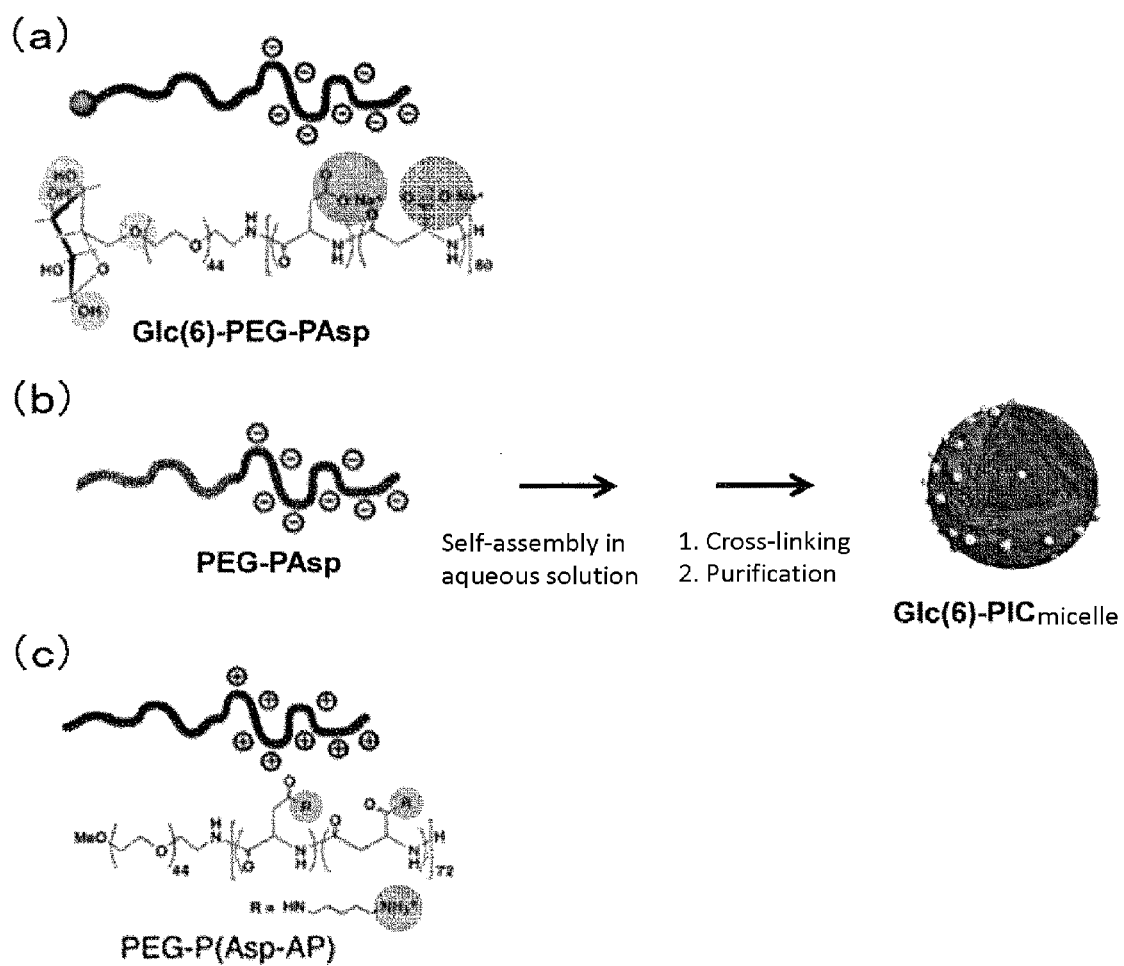
FIG. 1 shows a polyion complex micelle (PIC micelle) modified at the outer surface thereof with glucose and a preparation method thereof.

In the present invention, the "drug transporter" means a carrier for drug delivery. Examples thereof include fine particles capable of incorporating drugs, for example, vesicles, dendrimers, hydrogels, and nanospheres. The drug transporter generally has a size of 10 nm to 400 nm in terms of a diameter.

In the present specification, the "vesicle" refers to a micelle or a hollow fine particle. The vesicle preferably has a biocompatible shell and is modified at the outer surface thereof with a GLUT1 ligand. This allows the vesicle to interact with GLUT1.

In the present specification, the "micelle" means a vesicle formed from a single-layer molecular membrane. Examples of the micelle include a micelle formed from an amphipathic molecule such as a surfactant, and a micelle formed from a polyion complex (PIC micelle). It is known that the micelle is preferably modified at the outer surface thereof with polyethylene glycol from the viewpoint of a blood retention time.

In the present specification, the "liposome" means a vesicle formed from a double-layer molecular membrane. The molecular membrane is normally a phospholipid bilayer.

In the present specification, the "polyion complex polymersome" (hereinafter, also referred to as "PICsome") means a hollow fine particle formed from a polyion complex. It is known that PICsome is preferably modified at the outer surface thereof with polyethylene glycol from the viewpoint of a blood retention time.

In the present specification, the "polyion complex" (hereinafter, also referred to as "PIC") is an ion layer formed between a cationic block and an anionic block of two block copolymers as a result of mixing a copolymer of PEG and the anionic block and a copolymer of PEG and the cationic block in an aqueous solution so as to neutralize the charges. The bonding between PEG and each of these charged chains is aimed at preventing the polyion complex from being precipitated by aggregation and at thereby allowing the polyion complex to form a nanoparticle having a monodisperse core-shell structure having a particle size of several tens of nm. In this respect, PEG is also known to be convenient for attaining high biocompatibility and an improved blood retention time, because of covering the shell of the nanoparticle. It has been revealed that one of the charged block copolymers does not require the PEG moiety for the polyion complex formation, and the charged block copolymers may be replaced with a homopolymer, a surfactant, a nucleic acid, and/or an enzyme. Furthermore, in the polyion complex formation, at least one of the anionic polymer and the cationic polymer is copolymerized with PEG, or both of these polymers may be copolymerized with PEG. As well-known, an increased content of PEG facilitates forming a PIC micelle, while a decreased content of PEG facilitates forming PICsome. Examples of the anionic polymer or block that is often used in the preparation of the polyion complex include polyglutamic acid, polyaspartic acid, and nucleic acids (e.g., DNA, mRNA, and siRNA). Examples of the cationic polymer or block include polylysine and poly(5-aminopentylaspartic acid). In this context, the mRNA means messenger RNA that is used in protein synthesis through translation. The siRNA means double-stranded RNA (nucleic acid) that can induce RNA interference (RNAi). The siRNA is not particularly limited and is double-stranded RNA of 20 to 30 bp, preferably 21 to 23 bp, 25 bp, or 27 bp, and this double-stranded RNA has a sequence homologous to the sequence of a target gene.

In the present specification, the term "for drug delivery" means being biocompatible and rendering the vesicle capable of incorporating a drug. In the present specification, the term "for drug delivery" may mean use based on the effect of prolonging the blood retention time of a drug compared with the blood retention time of a naked drug.

In the present specification, the phrase "cause a subject to have hypoglycemia" means that the blood glucose level in the subject is lowered to below blood glucose supposed to be exhibited by the subject without the procedure. Examples of the method for causing a subject to have hypoglycemia include the administration of an antidiabetic drug. For example, when the subject is caused to have hypoglycemia, the subject is permitted, for example, to take other drugs or to drink a beverage such as water as long as the object to cause the subject to have hypoglycemia is attained. Other procedures that do not substantially influence blood glucose may be further carried out for causing a subject to have hypoglycemia.

In the present specification, the term "fast" means that the subject is fasted for, for example, 3 hours or longer, 4 hours or longer, 5 hours or longer, 6 hours or longer, 7 hours or longer, 8 hours or longer, 9 hours or longer, 10 hours or longer, 11 hours or longer, 12 hours or longer, 13 hours or longer, 14 hours or longer, 15 hours or longer, 16 hours or longer, 17 hours or longer, 18 hours or longer, 19 hours or longer, 20 hours or longer, 21 hours or longer, 22 hours or longer, 23 hours or longer, 24 hours or longer, 25 hours or longer, 26 hours or longer, 27 hours or longer, 28 hours or longer, 29 hours or longer, 30 hours or longer, 31 hours or longer, 32 hours or longer, 33 hours or longer, 34 hours or longer, 35 hours or longer, 36 hours or longer, 37 hours or longer, 38 hours or longer, 39 hours or longer, 40 hours or longer, 41 hours or longer, 42 hours or longer, 43 hours or longer, 44 hours or longer, 45 hours or longer, 46 hours or longer, 47 hours or longer, or 48 hours or longer. As a result of this fasting, hypoglycemia is caused in the subject. The fasting period is determined by a physician or the like in light of the physical conditions of the subject and is preferably, for example, a period of time or longer by which the subject reaches fasting blood glucose. The fasting period may be, for example, a period of time or longer by which the expression of GLUT1 on the intravascular surface of cerebrovascular endothelial cells is increased or reaches a plateau. The fasting period can be the aforementioned period of, for example, 12 hours or longer, 24 hours or longer, or 36 hours or longer. Other procedures that do not substantially influence blood glucose levels or the expression of GLUT1 on the intravascular surface may be further carried out for the fasting.

In the present specification, the phrase "induce an increase in blood glucose level" means that the blood glucose level is raised in the subject caused to have hypoglycemia or the subject with the hypoglycemic state maintained. The blood glucose level can be raised by various methods well known to those skilled in the art and can be raised, for example, by the administration of a material that induces an increase in blood glucose level, for example, the administration of a monosaccharide that induces a rise in blood glucose level, such as glucose, fructose, or galactose, the administration of a polysaccharide that induces an increase in blood glucose level, such as maltose, or the ingestion of a carbohydrate that induces an increase in blood glucose level, such as starch, or by diet.

In the present specification, the "blood glucose control" refers to causing a subject to have hypoglycemia and then raising the blood glucose level of the subject. The blood glucose level of the subject thus caused to have hypoglycemia can be kept at hypoglycemia. The time for which the blood glucose level of the subject is kept at hypoglycemia can be, for example, 0 hours or longer, 1 hour or longer, 2 hours or longer, 3 hours or longer, 4 hours or longer, 5 hours or longer, 6 hours or longer, 7 hours or longer, 8 hours or longer, 9 hours or longer, 10 hours or longer, 11 hours or longer, 12 hours or longer, 13 hours or longer, 14 hours or longer, 15 hours or longer, 16 hours or longer, 17 hours or longer, 18 hours or longer, 19 hours or longer, 20 hours or longer, 21 hours or longer, 22 hours or longer, 23 hours or longer, 24 hours or longer, 25 hours or longer, 26 hours or longer, 27 hours or longer, 28 hours or longer, 29 hours or longer, 30 hours or longer, 31 hours or longer, 32 hours or longer, 33 hours or longer, 34 hours or longer, 35 hours or longer, 36 hours or longer, 37 hours or longer, 38 hours or longer, 39 hours or longer, 40 hours or longer, 41 hours or longer, 42 hours or longer, 43 hours or longer, 44 hours or longer, 45 hours or longer, 46 hours or longer, 47 hours or longer, or 48 hours or longer. Then, the blood glucose level can be raised. In the present specification, the subject whose "blood glucose is maintained or kept" is permitted, for example, to take other drugs or to drink a beverage such as water as long as the object to maintain the hypoglycemia is attained. Other procedures that do not substantially influence blood glucose may be further carried out for causing a subject to have hypoglycemia.

In the present specification, the "subject" is a mammal including a human. The subject may be a healthy subject or may be a subject affected by some disease. In this context, examples of the disease include cranial nerve diseases, for example, psychotic disorder, depression, mood disorder, anxiety, sleep disorder, dementia, and substance-related disorder. Examples of the dementia include, but are not particularly limited to, Alzheimer's disease and Creutzfeldt-Jakob disease.

In the present specification, the "blood-brain barrier" refers to a functional barrier that is located between blood circulation and the brain and has the penetration selectivity of materials. The entity of the blood-brain barrier is considered to be cerebrovascular endothelial cells, etc. Although much remains unknown about the material penetration of the blood-brain barrier, glucose, alcohols, and enzymes are known to easily cross the blood-brain barrier. Fat-soluble substances or small molecules (having a molecular weight of, for example, smaller than 500) are considered to tend to more easily cross the blood-brain barrier than water-soluble molecules or large molecules (having a molecular weight of, for example, 500 or larger). Many therapeutic drugs for brain diseases and brain diagnostic drugs fail to cross the blood-brain barrier. This largely hinders the treatment of brain diseases, the analysis of the brain, etc. In the present specification, the "blood-nerve barrier" refers to a functional barrier that is located between blood circulation and peripheral nerve and has the penetration selectivity of materials. In the present specification, the "blood-cerebrospinal fluid barrier" refers to a functional barrier that is located between blood circulation and cerebrospinal fluid and has the penetration selectivity of materials. In the present specification, the "blood-retina barrier" refers to a functional barrier that is located between blood circulation and retina tissues and has the penetration selectivity of materials. The entities of the blood-nerve barrier, the blood-cerebrospinal fluid barrier, and the blood-retina barrier are considered to be respective vascular endothelial cells, etc., present in these barriers. These barriers seem to be functionally similar to the blood-brain barrier.

In the present specification, the "GLUT1 ligand" means a substance specifically binding to GLUT1. Various ligands are known as GLUT1 ligands. Examples of GLUT1 ligands include, but are not particularly limited to, molecules such as glucose and hexose. In the present invention, any of these GLUT1 ligands can be used in the preparation of a carrier or a conjugate instead of glucose. The GLUT1 ligand preferably has affinity equivalent to or higher than that of glucose for GLUT1. 2-N-4-(1-azi-2,2,2-trifluoroethyl)benzoyl-1,3-bis(D-mannos-4-yloxy)-2-propylamine (ATB-BMPA), 6-(N-(7-nitrobenz-2-oxa-1,3-diazol-4-yl)amino)-2-deoxyglucose (6-NBDG), 4,6-O-ethylidene-α-D-glucose, 2-deoxy-D-glucose, and 3-O-methylglucose are also known to bind to GLUT1. In the present invention, any of these molecules can also be used as the GLUT1 ligand.

It has been found that the carrier modified at the outer surface thereof with glucose according to the present invention exhibits accumulation in the brain by mere administration to a subject. Thus, the dosing regimen according to the present invention does not require fasting a subject or causing a subject to have hypoglycemia and/or does not require inducing an increase in blood glucose level. The present inventors have also found that a carrier, specifically, a vesicle such as a micelle or a polyion complex polymersome (PICsome), modified at the outer surface thereof with glucose such that the glucose is exposed on the surface thereof is administered according to a certain dosing regimen, whereby the carrier is significantly delivered into the brain (brain parenchyma) across the blood-brain barrier. Thus, the dosing regimen according to the present invention preferably comprises administering the composition to a subject who has been fasted or caused to have hypoglycemia. The dosing regimen according to the present invention more preferably comprises administering the composition to a subject who has been fasted or caused to have hypoglycemia and inducing an increase in blood glucose level in the subject. In the dosing regimen according to the present invention, the composition can be administered to the subject simultaneously, consecutively, or successively with the induction of an increase in blood glucose level in the subject. The dosing regimen may or may not have an interval between the administration of the composition to the subject and the induction of an increase in blood glucose level in the subject. In the case of administering the composition to the subject simultaneously with the induction of an increase in blood glucose level, the composition may be administered to the subject in a form mixed with a drug that induces an increase in blood glucose level, or may be administered to the subject in a form separate from a drug that induces an increase in blood glucose level. In the case of administering the composition to the subject consecutively or successively with the induction of an increase in blood glucose level in the subject, the composition may be administered to the subject before or after the induction of an increase in blood glucose level in the subject. Preferably, the composition can be administered to the subject before the induction of an increase in blood glucose level in the subject. In the case of inducing an increase in blood glucose level in the subject before the administration of the composition to the subject, the composition is preferably administered to the subject within 1 hour, within 45 minutes, within 30 minutes, within 15 minutes, or within 10 minutes after the induction of an increase in blood glucose level in the subject. In the case of inducing an increase in blood glucose level in the subject after the administration of the composition to the subject, a rise in blood glucose level is preferably induced in the subject within 6 hours, within 4 hours, within 2 hours, within 1 hour, within 45 minutes, within 30 minutes, within 15 minutes, or within 10 minutes after the administration of the composition to the subject. The aforementioned cycle of the dosing regimen may be carried out two or more times. The order in which glucose and the sample are administered can be determined according to crossing timing at the blood-brain barrier.

The cerebral cortex is composed of 6 layers and contains a molecular layer (first layer), an external granular layer (second layer), an external pyramidal layer (third layer), an internal granular layer (fourth layer), an internal pyramidal layer (fifth layer), and a multiform layer (sixth layer) in this order from the cortical layer. According to the present invention, the carrier can be delivered to the brain parenchyma in any of these layers. Particularly, the delivery of the carrier according to the present invention is significantly effective for the external pyramidal layer (third layer) and the internal granular layer (fourth layer) among these layers.

According to the present invention, very surprisingly, a giant carrier (diameter: approximately 40 nm to 100 nm), such as a micelle or PICsome, was also successfully delivered very efficiently to the brain. The fact that even such a vesicle was successfully delivered to the brain means that various macromolecules and carriers each modified with glucose are administered according to the aforementioned dosing regimen, whereby these macromolecules and carriers can effectively cross the blood-brain barrier.

Hereinafter, the role of glucose in the blood-brain barrier in the present invention will be described. The role of glucose in the present invention is considered to bind to a glucose transporter GLUT1 expressed on the intravascular surface of vascular endothelial cells in the brain. Thus, in the present invention, the GLUT1 ligand can also play the same role as that of glucose. Also, in the present invention, the GLUT' ligand can be conjugated such that the GLUT' ligand is exposed on the outer surface so as to be able to bind to the glucose transporter expressed on the intravascular surface of vascular endothelial cells in the brain. Thus, a molecule, a complex, and a vesicle, etc., capable of presenting the GLUT1 ligand to GLUT1 can bind to GLUT1 and, after this binding, is probably taken up into the vascular endothelial cells together with GLUT1 upon cellular uptake thereof through glucose. The vesicle thus taken up into the vascular endothelial cells crosses the blood-brain barrier and enters the brain parenchyma. When the vesicle was modified with a large number of glucose molecules, the proportion of a vesicle arriving at the brain parenchyma was decreased, albeit slightly. This suggests that: such vesicles modified with a large number of glucose molecules are taken up into the cells by endocytosis so that the vesicles cross the cells toward the brain parenchyma; and the dissociation efficiency between the vesicles and the vascular endothelial cells is reduced when the vesicles enter the brain parenchyma from the vascular endothelial cells. In other words, some of the vesicles taken up into the cells by endocytosis are accumulated in the cerebrovascular endothelial cells without being dissociated from the cerebrovascular endothelial cells. Thus, the composition or the conjugate of the present invention can be used for delivery to a cerebrovascular endothelial cell. Glucose in the present invention also plays a similar role in the blood-nerve barrier, the blood-retina barrier, and the blood-cerebrospinal fluid barrier. GLUT1 is expressed on the vascular endothelial cells at the time of hypoglycemia, particularly, in the blood-nerve barrier, the blood-retina barrier, and the blood-cerebrospinal fluid barrier. Thus, the composition or the conjugate of the present invention can be used for crossing the blood-nerve barrier, the blood-retina barrier, and the blood-cerebrospinal fluid barrier. The composition or the conjugate of the present invention can also be used for delivery to a vascular endothelial cell present in the blood-nerve barrier, the blood-retina barrier, and the blood-cerebrospinal fluid barrier.

The present inventor has also found that a micelle obtained using a polymer conjugated with glucose via carbon at position 6 thereof (see e.g., FIG. 1($a$)) has higher uptake efficiency into the brain than that of a micelle obtained using a polymer conjugated with glucose via carbon at position 3 thereof. It is known that OH groups serving as substituents of carbon atoms at positions 1, 3, and 4 of glucose are strongly involved in the binding between GLUT1 and glucose. A micelle obtained by the modification of a polymer via the carbon atom at position 6, which is not used in binding to GLUT1, tends to be more effectively accumulated in the brain, indicating the involvement of GLUT1 in accumulation in the brain. Even a micelle obtained by the modification of a polymer via the carbon atom at position 3 reportedly important for the recognition of GLUT1 exhibited accumulation in the brain. This indicates that a micelle obtained by the modification of a polymer via the carbon atom at position 2 that is less involved in binding to GLUT1 has more chance of being accumulated in the brain. Thus, glucose can be conjugated, via any one of the carbon atoms at positions 1, 3, and 4 thereof, preferably via the carbon atom at position 2 or 6 thereof, with a polymer or a drug. In one embodiment, at least the OH groups at positions 1, 3, and 4 of the conjugated glucose are reducing ends. Thus, in the present invention, the GLUT1 ligand can be allowed to modify an additional molecule without losing the functions thereof as a ligand. Those skilled in the art can readily determine a binding site for a drug on the basis of the binding pattern with GLUT1. In the present specification, glucose conjugated via the carbon atom at position n is also referred to as "Glc(n)" wherein n is any integer of 1 to 4 and 6. In the present specification, for example, glucose conjugated via the carbon atom at position 6 is also referred to as "Glc(6)"; glucose conjugated via the carbon atom at position 2 is also referred to as "Glc(2)"; and glucose conjugated via the carbon atom at position 3 is also referred to as "Glc(3)".

In the present invention, a glucose derivative binding to GLUT1 may be used instead of glucose.

In the present invention, examples of the carrier that can be modified at the outer surface thereof with the GLUT1 ligand include vesicles for drug delivery, such as micelles, liposomes, and PICsome as well as dendrimers, nanospheres, and hydrogels. In the present invention, use of the carrier for drug delivery has the advantages that, for example, a drug is incorporated within the carrier so that the drug concentration is increased at a target site or the adverse reaction of the drug is reduced at sites other than the target site. The carrier used in the present invention has a diameter of, for example, 400 nm or smaller, 200 nm or smaller, 150 nm or smaller, 100 nm or smaller, or 80 nm or smaller and, for example, 20 nm or larger, 30 nm or larger, or 40 nm or larger, though the diameter is not particularly limited thereto. The carrier used in the present invention has a diameter of, for example, 30 nm to 150 nm, or, for example, 30 nm to 100 nm.

Examples of the micelle used in the present invention include micelles for drug delivery. A micelle formed from a block copolymer is known as such a micelle for drug delivery. The block copolymer constituting the micelle is not particularly limited and, in the case of a PIC micelle, can be a copolymer of a charged polymer block (e.g., a polyanion block or a polycation block) and a biocompatible block (e.g., a polyethylene glycol block) or a pharmaceutically acceptable salt thereof. A biodegradable block copolymer is preferably used as the block copolymer. Various copolymers are known as such copolymers, and any of these copolymers may be used in principle. For example, polyethylene glycol-polyaspartic acid, polyethylene glycol-polyglutamic acid, and polyethylene glycol-poly((5-aminopentyl)-aspartic acid) block copolymers can be used as, for example, highly biocompatible and biodegradable block copolymers. A micelle having a polyion complex layer formed through the electrostatic interaction between a polyanion and a polycation is known as the polyion complex micelle (PIC micelle). A hydrophobic moiety such as a cholesteryl group may be linked to an end different from the shell-forming PEG side in each charged block (see e.g., an siRNA micelle described in Examples) from the viewpoint of stabilizing the respective hydrophobic moieties of the charged blocks within the micelle. The block copolymer can be labeled with a fluorescent dye by the modification of an end opposite to the polyethylene glycol side of the block copolymer with the fluorescent dye (e.g., the NH$_2$ terminus of a compound shown in FIG. 1(a)). In the case of a PIC micelle, the GLUT' ligand is linked to the end on the PEG side so that the GLUT' ligand is exposed on the outer surface of the micelle.

Examples of the polyion complex polymersome used in the present invention include PICsome for drug delivery. PICsome formed from a block copolymer is known as such PICsome for drug delivery. Examples of the block copolymer constituting the PICsome include a block copolymer of a PEG block and a polycation block and homopolyanion, and a block copolymer of a PEG block and a polyanion block and homopolycation. A biodegradable block copolymer is preferably used as the block copolymer. Various copolymers are known as such copolymers, and any of these copolymers may be used in principle. For example, a poly(aspartic acid-tetraethylenepentamine (Asp-TEP)) block copolymer and a polyethylene glycol-poly((5-aminopentyl)-aspartic acid) block copolymer can be used as, for example, highly biocompatible and biodegradable block copolymers. In the case of PICsome, the GLUT1 ligand is linked to the end on the PEG side so that the GLUT1 ligand is exposed on the outer surface of the PICsome.

The present invention provides each of compounds represented by the formulas (I) to (XV) given below or salts thereof. The salts are preferably pharmaceutically acceptable salts.

Glc(6)-PEG-Polyaspartic Acid

[Formula 5]

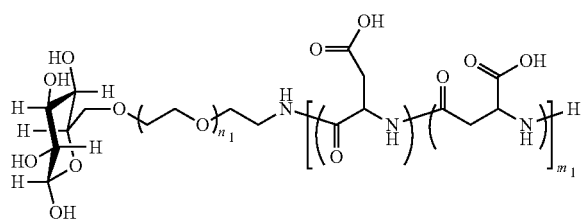

(I)

wherein $n_1$ and $m_1$ each represent 5 to 20,000.

Glc(6)-PEG-Polyglutamic Acid

[Formula 6]

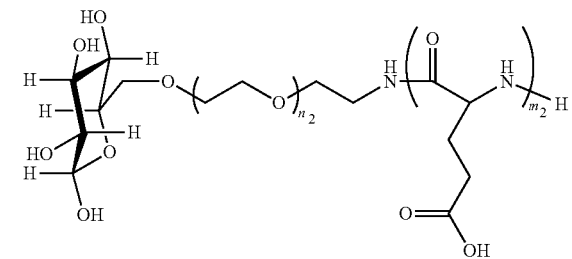

(II)

wherein $n_2$ and $m_2$ each represent 5 to 20,000.

Glc(6)-PEG-Poly((5-Aminopentyl)-Aspartic Acid)

[Formula 7]

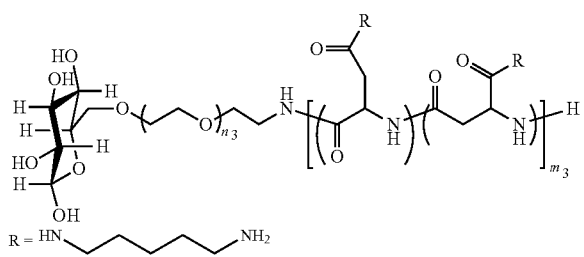

(III)

wherein $n_3$ and $m_3$ each represent 5 to 20,000.

PEG-Polyaspartic Acid

[Formula 8]

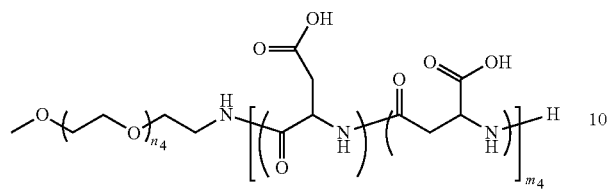

(IV)

wherein $n_4$ and $m_4$ each represent 5 to 20,000.

PEG-Polyglutamic Acid

[Formula 9]

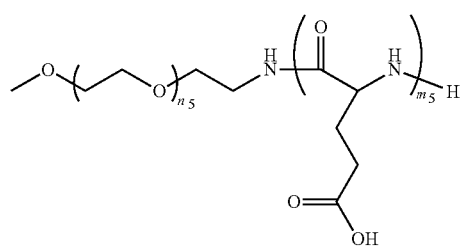

(V)

wherein $n_5$ and $m_5$ each represent 5 to 20,000.

PEG-Poly((5-Aminopentyl)-Aspartic Acid)

[Formula 10]

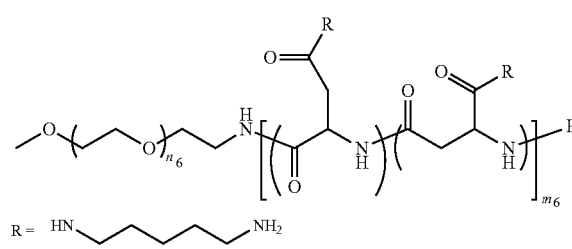

(VI)

wherein $n_6$ and $m_6$ each represent 5 to 20,000.

Polyaspartic Acid

[Formula 11]

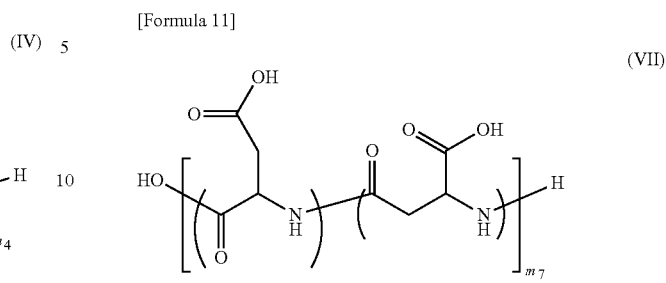

(VII)

wherein $m_7$ represents 5 to 20,000.

Polyglutamic Acid

[Formula 12]

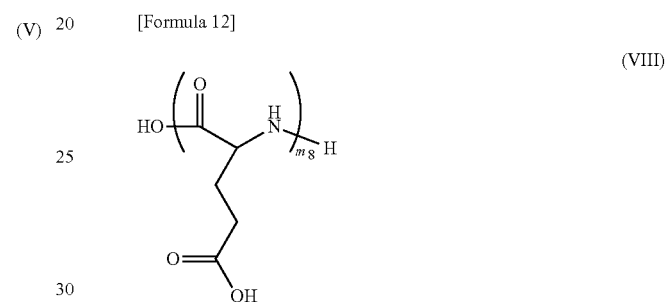

(VIII)

wherein $m_8$ represents 5 to 20,000.

Poly((5-Aminopentyl)-Aspartic Acid)

[Formula 13]

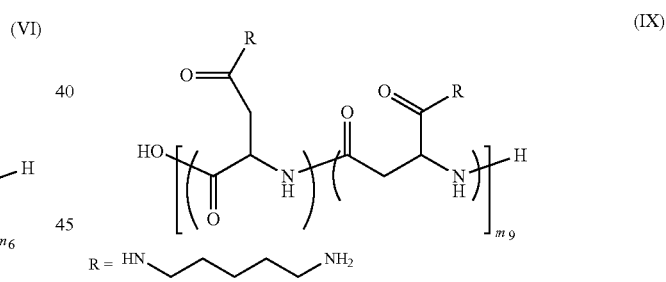

(IX)

wherein $m_9$ represents 5 to 20,000.

Glc(3)-PEG-Polyaspartic Acid

[Formula 14]

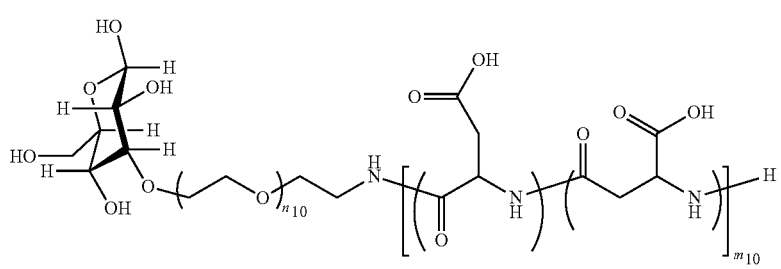

(X)

wherein $n_{10}$ and $m_{10}$ each represent 5 to 20,000.

Glc(3)-PEG-Polyglutamic Acid
[Formula 15]
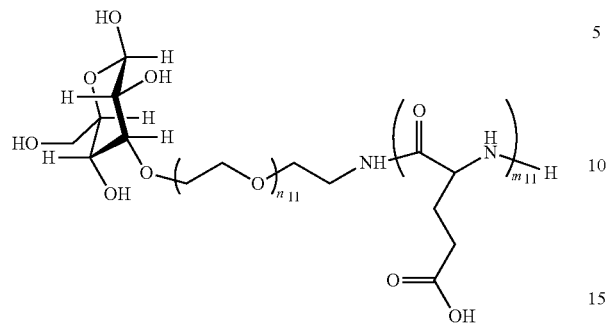
(XI)
wherein $n_{11}$ and $m_{11}$ each represent 5 to 20,000.
Glc(3)-PEG-Poly((5-Aminopentyl)-Aspartic Acid)
[Formula 16]
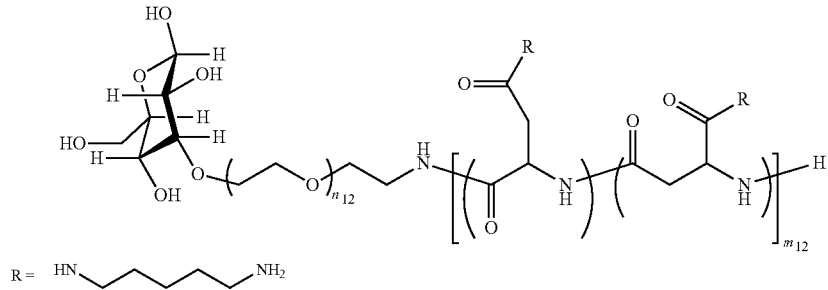
(XII)
wherein $n_{12}$ and $m_{12}$ each represent 5 to 20,000.
Glc(2)-PEG-Polyaspartic Acid
[Formula 17]
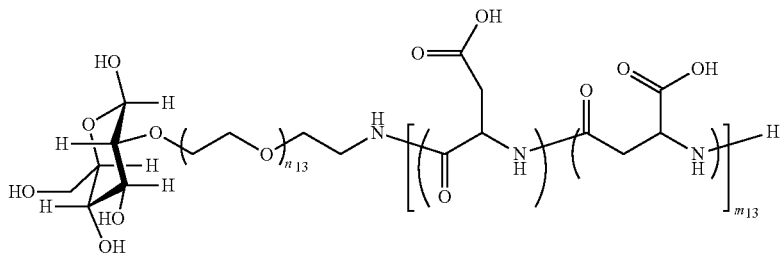
(XIII)
wherein $n_{13}$ and $m_{13}$ each represent 5 to 20,000.
Glc(2)-PEG-Polyglutamic Acid
[Formula 18]
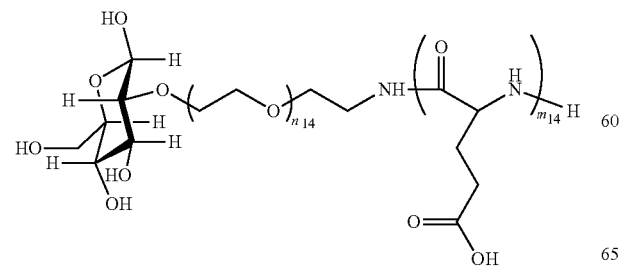
(XIV)
wherein $n_{14}$ and $m_{14}$ each represent 5 to 20,000.

Glc(2)-PEG-Poly((5-Aminopentyl)-Aspartic Acid)

[Formula 19]

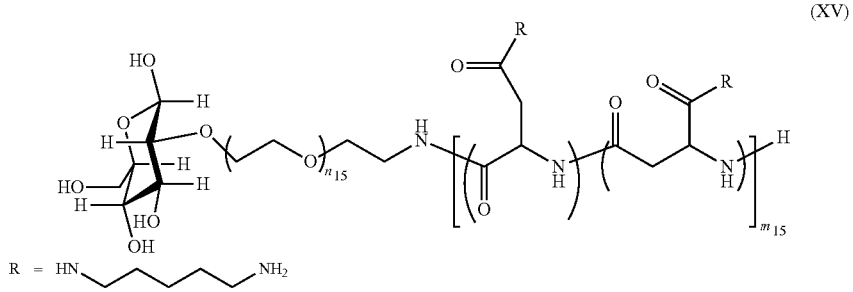

wherein $n_{15}$ and $m_{15}$ each represent 5 to 20,000.

The compounds of the formulas (I) to (XV) or the salts thereof can each be used for forming a PIC micelle or PICsome modified at the outer surface thereof with glucose. For forming polyion complexes using the salts of the compounds of the formulas (I) to (XV) $n_1$, $n_2$, $n_3$, $n_4$, $n_5$, $n_6$, $n_7$, $n_8$, $n_9$, $n_{10}$, $n_{11}$, $n_{12}$, $n_{13}$, $n_{14}$, and $n_{15}$ can each independently be an integer of 5 to 20,000, preferably an integer of 10 to 5,000, more preferably an integer of 40 to 500, further preferably an integer of 5 to 1,000, still further preferably an integer of 10 to 200. Also, $m_1$, $m_2$, $m_3$, $m_4$, $m_5$, $m_6$, $m_7$, $m_8$, $m_9$, $m_{10}$, $m_{11}$, $m_{12}$, $m_{13}$, $m_{14}$, and $m_{15}$ can each independently be an integer of 2 to 20,000, preferably an integer of 2 to 5,000, more preferably an integer of 40 to 500, further preferably an integer of 5 to 1,000, still further preferably an integer of 10 to 200. The salts are preferably pharmaceutically acceptable salts.

In one embodiment, the PIC micelle is obtained by mixing the compound of the formula (I) or the salt thereof, the compound of the formula (X) or the salt thereof or the compound of the formula (XIII) or the salt thereof, the compound of the formula (IV) or the salt thereof, and the compound of the formula (VI) or the salt thereof. In a further particular embodiment of the PIC micelle, in the above formulas, each of $n_1$, $n_{10}$, $n_{13}$, $n_4$, and $n_6$ is 44, each of $m_1$, $m_{10}$, $m_{13}$, and $m_4$ is 80, and $m_6$ is 72. The salts are preferably pharmaceutically acceptable salts.

In one embodiment, the PICsome is obtained by mixing the compound of the formula (I) or the salt thereof, the compound of the formula (X) or the salt thereof or the compound of the formula (XIII) or the salt thereof, the compound of the formula (IV) or the salt thereof, and the compound of the formula (IX) or the salt thereof. In a further particular embodiment of the PICsome, in the above formulas, each of $n_1$, $n_{10}$, $n_{13}$, $n_4$, and $n_9$ is 44, each of $m_1$, $m_{10}$, $m_{13}$, and $m_4$ is 80, and $m_9$ is 72. The salts are preferably pharmaceutically acceptable salts.

In one embodiment, the siRNA micelle is obtained by mixing cholesterol-conjugated siRNA with cholesterol-conjugated Glc(6)-PEG-poly(Asp-TEP) represented by the formula (XVI) or a salt thereof. The salt is preferably a pharmaceutically acceptable salt. The cholesterol-conjugated siRNA is not particularly limited and is siRNA comprising an RNA strand conjugated at the 5' end or 3' end thereof with cholesterol. Such siRNA can be appropriately synthesized by those skilled in the art or is commercially available by custom-made synthesis. Any of these siRNAs can be used in the present invention. The siRNA can be preferably conjugated at the 3' end of the sense strand thereof or the 5' end or 3' end of the antisense strand thereof with cholesterol, though the position is not limited thereto.

Glc(6)-PEG-Poly(Asp-TEP)-Chol

[Formula 20]

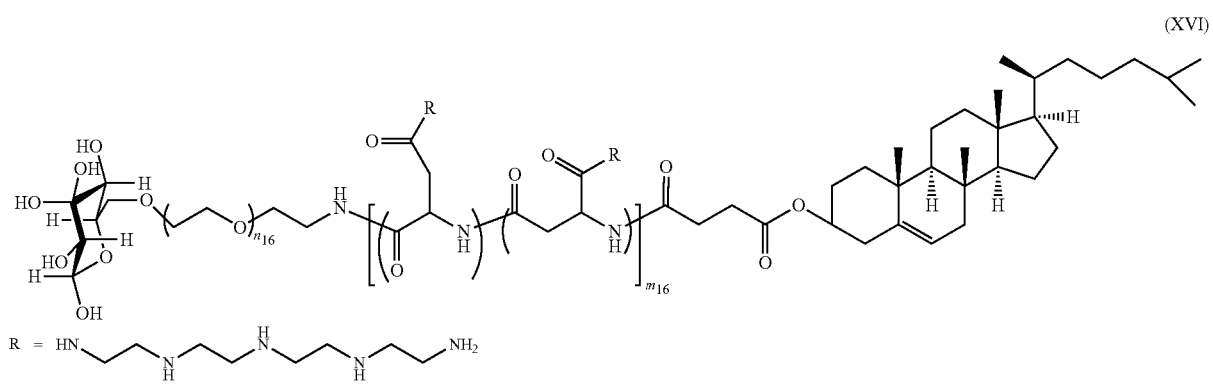

wherein $n_{16}$ and $m_{16}$ each represent 5 to 20,000.

$n_{16}$ is an integer of 5 to 20,000, preferably an integer of 10 to 5,000, more preferably an integer of 40 to 500, further preferably an integer of 5 to 1,000. $m_{16}$ is an integer of 2 to 20,000, preferably an integer of 2 to 5,000, more preferably an integer of 40 to 500, further preferably an integer of 5 to 1,000, still further preferably an integer of 10 to 200. In a further particular embodiment of the siRNA micelle, in the above formula, $n_{16}$ is 440, and $m_{16}$ is 60.

Examples of the liposome used in the present invention include, but are not particularly limited to, liposomes formed from phospholipids, for example, dimyristoyl phosphatidylcholine (DMPC). Various liposomes have heretofore been known and can be appropriately prepared by those skilled in the art. A drug can be appropriately incorporated to the liposome by those skilled in the art.

The modification of the vesicle with the GLUT1 ligand is not particularly limited and can be carried out, for example, by modifying a vesicle-forming polymer with the GLUT1 ligand and then forming the vesicle. The modification site of the polymer can be a site that is positioned on the outer surface of the formed vesicle from the viewpoint of exposure on the outer surface of the vesicle. The polymer thus modified with the GLUT1 ligand can be appropriately prepared by those skilled in the art. Hereinafter, an exemplary method for preparing a polymer modified with glucose (particularly, a Glc(6)-PEG-poly(anion) block copolymer or a Glc(6)-PEG-poly(cation) block copolymer) will be described as one example. The Glc(6)-PEG-poly(anion) block copolymer or the Glc(6)-PEG-poly(cation) block copolymer can be obtained, for example, by protecting hydroxy groups on carbon atoms at positions other than position 6 of glucose and then polymerizing the block copolymer with the resulting glucose.

Scheme 1A illustrates a synthesis scheme of the compound of the formula (I) wherein $n_1$ is 44, and $m_1$ is 80.

Scheme 1A

[Formula 21]

Scheme 1A

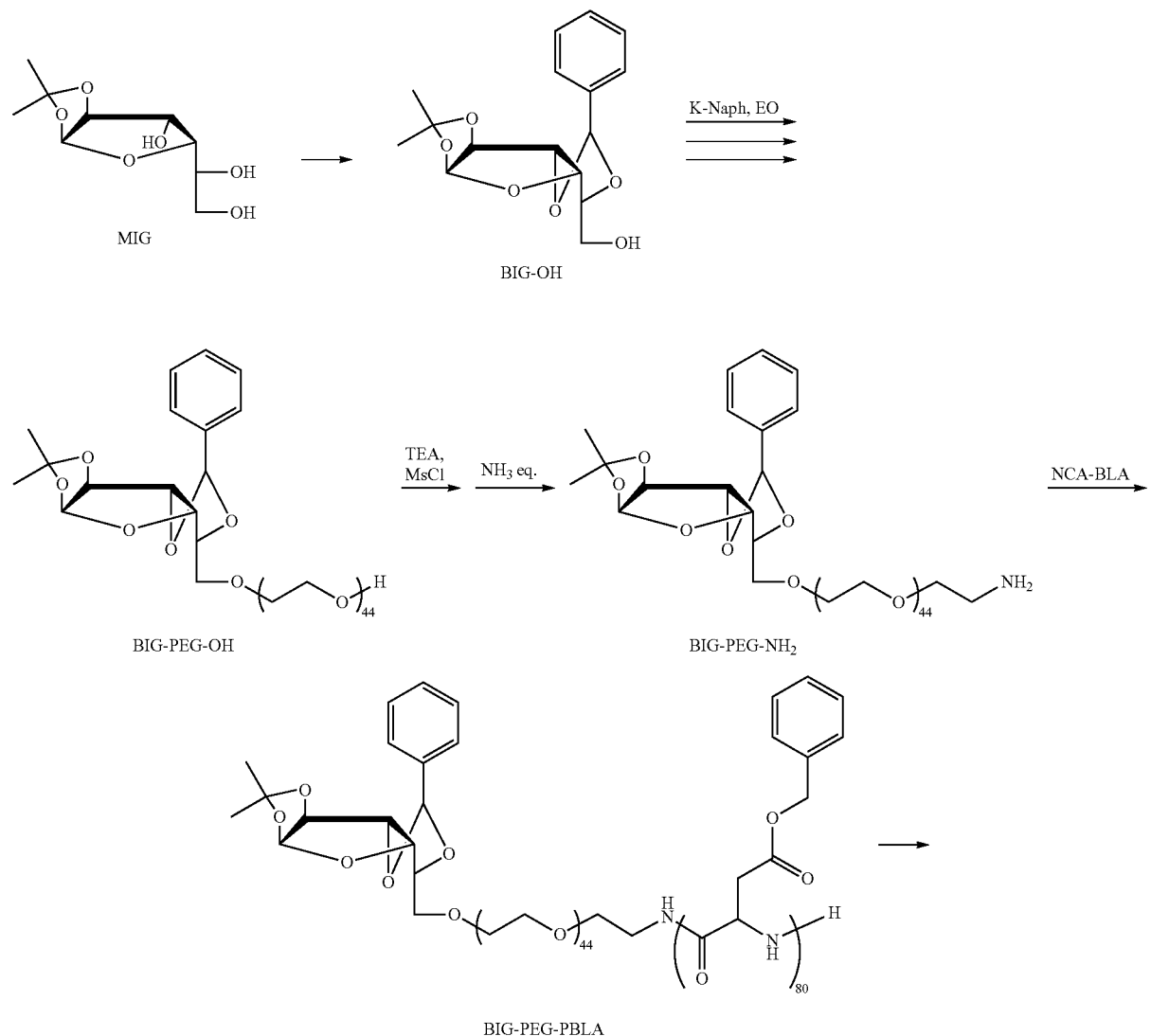

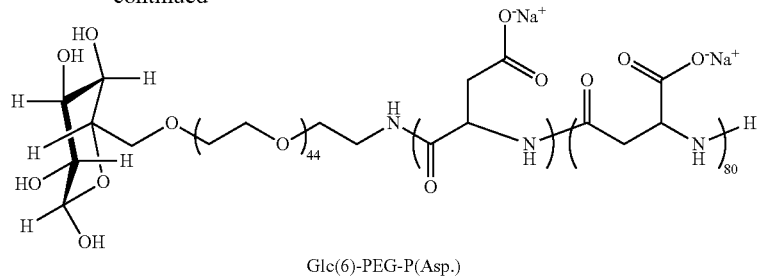

Glc(6)-PEG-P(Asp.)

In scheme 1A, EO represents ethylene oxide; K-Naph represents potassium naphthalene; TEA represents triethylamine; MsCl represents methanesulfonyl chloride; NH$_3$aq. represents ammonia water; and NCA-BLA represents β-benzyl-L-aspartate-N-carboxylic anhydride.

Hereinafter, scheme TA will be described briefly. The introduction of protective groups into glucose is achieved with, for example, 1,2-O-isopropylidene-5,6-O-benzylidene-α-D-glucofuranose (hereinafter, referred to as "BIG"). In the case of preparing, for example, a PIC micelle or PICsome, ethylene oxide is polymerized with BIG to synthesize BIG-PEG-OH. BIG is obtained, for example, by protecting OH groups serving as substituents on the carbon atoms at positions 3 and 5 of 1,2-O-isopropylidene-α-D-glucofuranose (hereinafter, referred to as "MIG") with benzyl groups. Specifically, BIG is obtained by reacting MIG with benzaldehyde, followed by extraction with ethyl acetate. From the viewpoint of keeping the molecular weight of PEG constant, it is preferred that, before the polymerization reaction, BIG-OH should be freeze-dried over benzene in a reaction vessel and then dried under reduced pressure (e.g., dried under reduced pressure overnight at 70° C.) to attach the BIG-OH to the wall of the vessel. The degree of polymerization can be appropriately adjusted by the amount of ethylene oxide added. After the polymerization, the OH group of BIG-PEG-OH is aminated to obtain BIG-PEG-NH$_2$. A polycation or a polyanion, or a protected precursor thereof (e.g., β-benzyl-L-aspartate-N-carboxylic anhydride (BLA-NCA), which is a protected monomer of polyaspartic acid, or γ-benzyl-L-glutamate-N-carboxylic anhydride (BLG-NCA), which is a protected monomer of polyglutamic acid) can be further polymerized with the NH$_2$ group of BIG-PEG-NH$_2$ to obtain BIG-PEG-poly(anion) or BIG-PEG-poly(cation). The degree of polymerization can be appropriately adjusted by the amount of the polycation or the polyanion, or the protected precursor thereof. Finally, the protective groups in the glucose and the anion or the cation can be deprotected to obtain glucose-PEG-poly(anion) or glucose-PEG-poly(cation). The copolymer conjugated with glucose can be used in the preparation of a PIC micelle or PICsome. Specifically, the polymer having a polycation block and the polymer having a polyanion block are mixed at a ratio that neutralizes the charges in an aqueous solution. As a result, the PIC micelle or the PICsome is spontaneously formed. In this way, a PIC micelle or PICsome in which the polyion complex is covered with a biocompatible moiety that is modified with glucose can be obtained.

Likewise, Glc(3)-PEG-poly(anion) and Glc(3)-PEG-poly(cation) can be synthesized in totally the same way as above except that, for example, 1,2,5,6-di-O-isopropylidene-α-D-glucofuranose (DIG) is used as a starting material instead of BIG (see scheme 1B). Likewise, Glc(2)-PEG-poly(anion) and Glc(2)-PEG-poly(cation) can be appropriately synthesized by those skilled in the art, Scheme 1B illustrates a synthesis scheme of the compound of the formula (X) wherein n$_1$ is 44, and m$_1$ is 80. Scheme 1B is the same as scheme 1A except that DIG is used as a starting material instead of BIG.

Scheme 1B

[Formula 22]

Scheme 1B

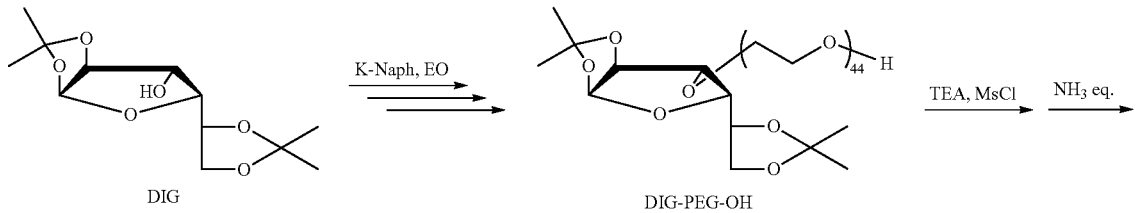

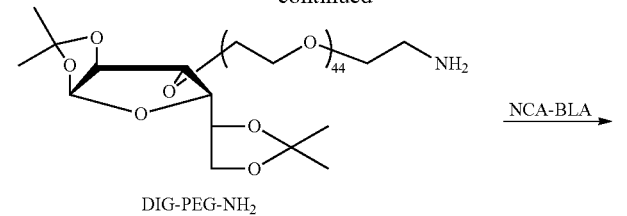

DIG-PEG-NH₂ →NCA-BLA→

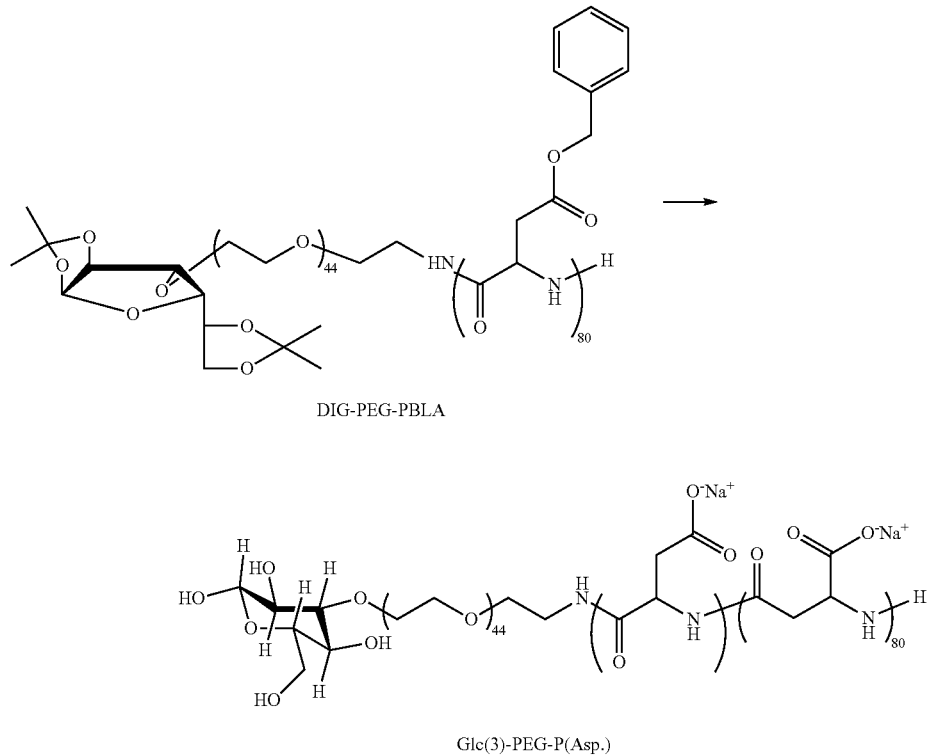

DIG-PEG-PBLA

Glc(3)-PEG-P(Asp.)

In scheme 1B, EO represents ethylene oxide; K-Naph represents potassium naphthalene; TEA represents triethylamine; MsCl represents methanesulfonyl chloride; NH₃aq. represents ammonia water; and NCA-BLA represents β-benzyl-L-aspartate-N-carboxylic anhydride.

The present invention provides a method for producing a conjugate represented by the formula (I) or a pharmaceutically acceptable salt thereof:

[Formula 23]

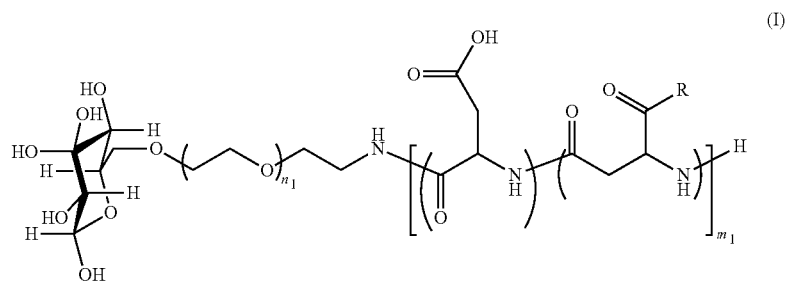

(I)

wherein $n_1$ and in each represent 5 to 20,000, the method comprising:

(i) reacting 1,2-O-isopropylidene-α-D-glucofuranose represented by the formula (Ia):

[Formula 24]

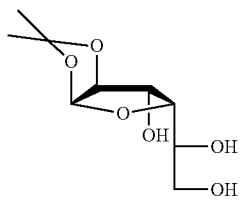

(Ia)

with benzaldehyde to obtain 1,2-O-isopropylidene-5,6-O-benzylidene-α-D-glucofuranose (BIG) represented by the formula (Ib):

[Formula 25]

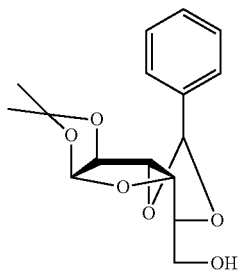

(Ib)

(ii) reacting the BIG represented by the formula (Ib) with ethylene oxide to obtain BIG-polyethylene glycol (BIG-PEG-OH) represented by the formula (Ic):

[Formula 26]

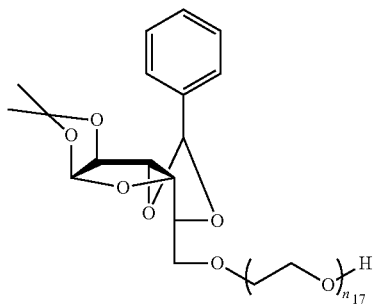

(Ic)

wherein $n_{17}$ is equal to $n_1$, (iii) aminating the BIG-PEG-OH represented by the formula (Ic) to obtain BIG-PEG-NH$_2$ represented by the formula (Id):

[Formula 27]

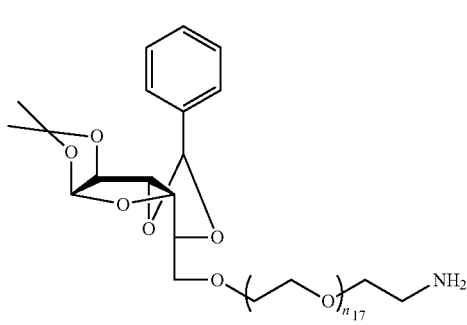

(Id)

and (iv) polymerizing β-benzyl-L-aspartate-N-carboxylic anhydride with the BIG-PEG-NH$_2$ represented by the formula (Id), followed by the deprotection of the protective groups.

The present invention provides a method for producing a conjugate represented by the formula (II) or a pharmaceutically acceptable salt thereof:

[Formula 28]

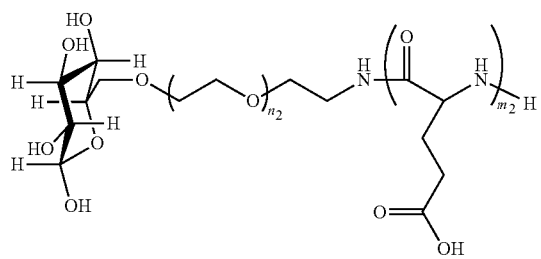

(II)

wherein $n_2$ and $m_2$ each represent 5 to 20,000, the method comprising:

(i) reacting 1,2-O-isopropylidene-α-D-glucofuranose represented by the formula (Ia):

[Formula 29]

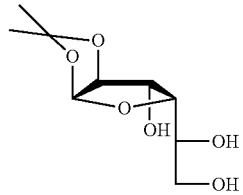

(Ia)

with benzaldehyde to obtain 1,2-O-isopropylidene-5,6-O-benzylidene-α-D-glucofuranose (BIG) represented by the formula (Ib):

[Formula 30]

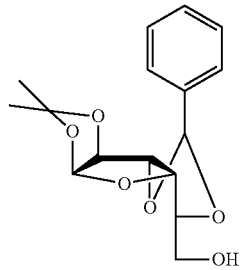

(Ib)

(ii) reacting the BIG represented by the formula (Ib) with ethylene oxide to obtain BIG-polyethylene glycol (BIG-PEG-OH) represented by the formula (Ic):

[Formula 31]

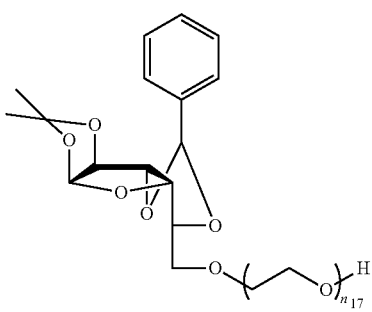
(Ic)

wherein $n_{17}$ is equal to $n_2$, (iii) aminating the BIG-PEG-OH represented by the formula (IC) to obtain BIG-PEG-NH$_2$ represented by the formula (Id):

[Formula 32]

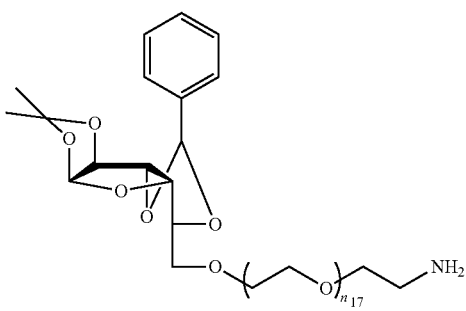
(Id)

and (iv) reacting the BIG-PEG-NH$_2$ with γ-benzyl-L-glutamate-N-carboxylic anhydride, followed by the deprotection of the protective groups.

The present invention provides a method for producing a conjugate represented by the formula (III) or a pharmaceutically acceptable salt thereof:

[Formula 33]

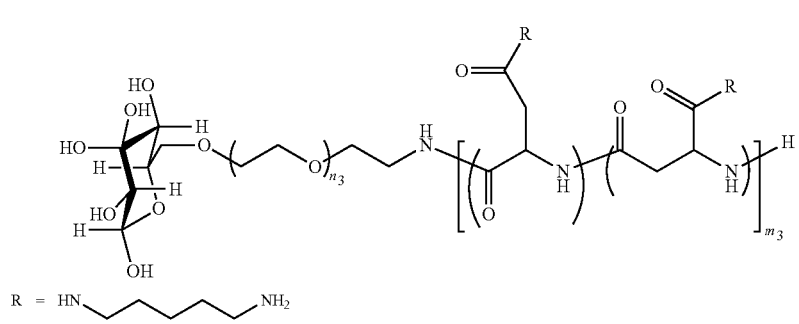
(III)

wherein $n_3$ and $m_3$ each represent 5 to 20,000, the method comprising:

(i) reacting 1,2-O-isopropylidene-α-D-glucofuranose represented by the formula (Ia):

[Formula 34]

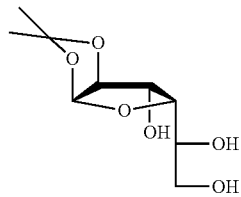
(Ia)

with benzaldehyde to obtain 1,2-O-isopropylidene-5,6-O-benzylidene-α-D-glucofuranose (BIG) represented by the formula (Ib):

[Formula 35]

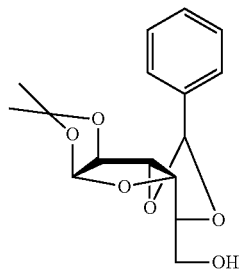
(Ib)

(ii) reacting the BIG represented by the formula (Ib) with ethylene oxide to obtain BIG-polyethylene glycol (BIG-PEG-OH) represented by the formula (Ic):

[Formula 36]

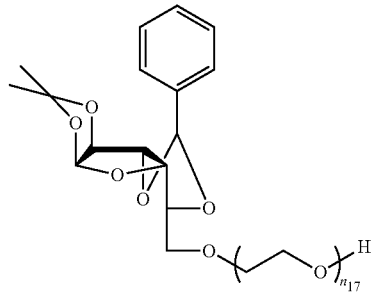
(Ic)

wherein $n_{17}$ is equal to $n_3$, (iii) aminating the BIG-PEG-OH represented by the formula (Ic) to obtain BIG-PEG-NH$_2$ represented by the formula (Id):

[Formula 37]

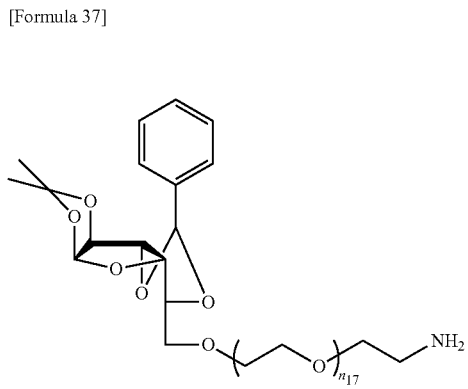

(Id)

(iv) polymerizing β-benzyl-L-aspartate-N-carboxylic anhydride with the BIG-PEG-NH$_2$ represented by the formula (Id), and (v) reacting the obtained compound with 1,5-diaminopentane (DAP), followed by the deprotection of the protective groups.

The present invention provides a method for producing a conjugate represented by the formula (X) or a pharmaceutically acceptable salt thereof:

[Formula 38]

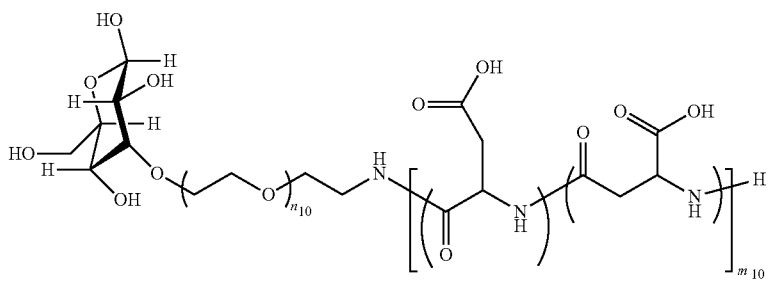

wherein $N_{10}$ and $m_{10}$ each represent 5 to 20,000, the method comprising:

(i) reacting 1,2,5,6-di-O-isopropylidene-α-D-glucofuranose (DIG) represented by the formula (Xa):

[Formula 39]

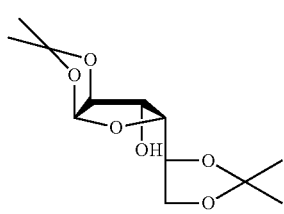

(Xa)

with ethylene oxide to obtain DIG-polyethylene glycol (DIG-PEG-OH) represented by the formula (Xb):

[Formula 40]

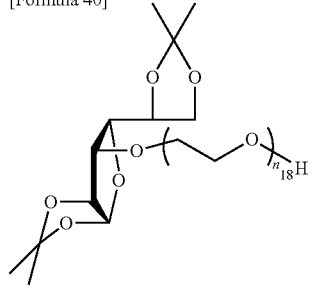

(Xb)

wherein $n_{18}$ is equal to $n_{10}$, (ii) substituting the OH group of the DIG-PEG-OH represented by the formula (Xb) by an amino group to obtain DIG-PEG-NH$_2$ represented by the formula (Xc):

[Formula 41]

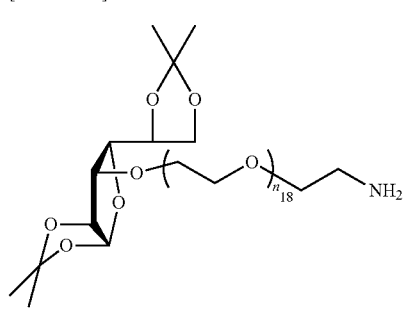

(Xc)

and (iii) polymerizing β-benzyl-L-aspartate-N-carboxylic anhydride with the amino group of the DIG-PEG-NH$_2$, followed by the deprotection of the protective groups.

The present invention provides a method for producing a conjugate represented by the formula (XI) or a pharmaceutically acceptable salt thereof:

[Formula 42]

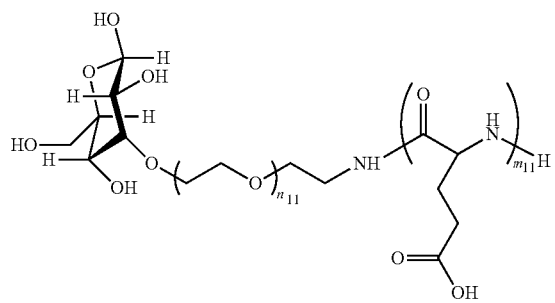

(XI)

wherein $n_{11}$ and $m_{11}$ each represent 5 to 20,000, the method comprising:

(i) reacting 1,2,5,6-di-O-isopropylidene-α-D-glucofuranose (DIG) represented by the formula (Xa):

[Formula 43]

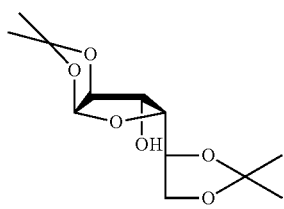

(Xa)

with ethylene oxide to synthesize DIG-polyethylene glycol (DIG-PEG-OH) represented by the formula (Xb):

[Formula 44]

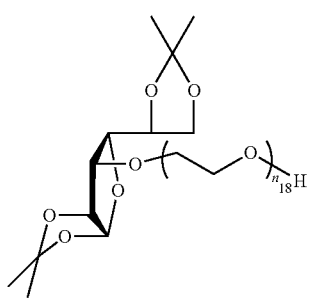

(Xb)

wherein $n_{18}$ is equal to $n_{11}$, (ii) substituting the OH group of the DIG-PEG-OH represented by the formula (Xb) by an amino group to obtain DIG-PEG-NH$_2$ represented by the formula (Xc):

[Formula 45]

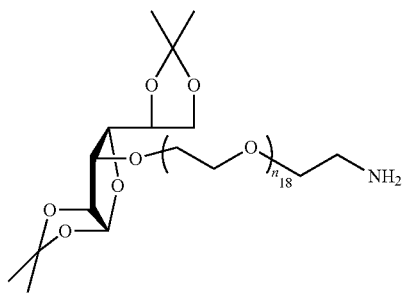

(Xc)

and (iii) reacting the amino group of the DIG-PEG-NH$_2$ with γ-benzyl-L-glutamate-N-carboxylic anhydride, followed by the deprotection of the protective groups.

The present invention provides a method for producing a conjugate represented by the formula (XII) or a pharmaceutically acceptable salt thereof:

[Formula 46]

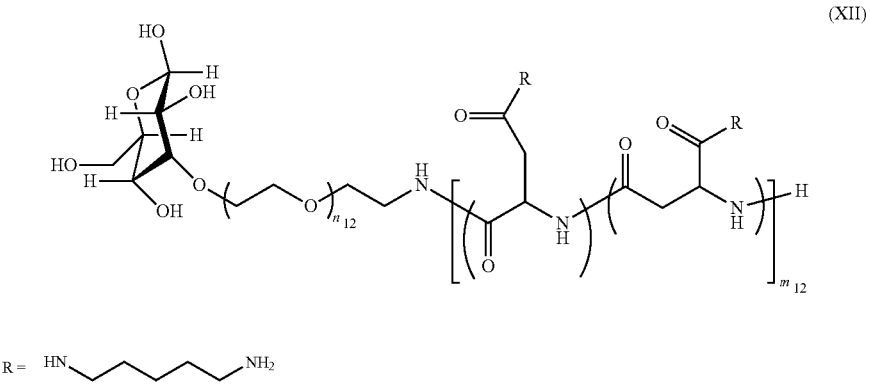

(XII)

wherein $n_{12}$ and $m_{12}$ each represent 5 to 20,000, the method comprising:

(i) reacting 1,2,5,6-di-O-isopropylidene-α-D-glucofuranose (DIG) represented by the formula (Xa):

[Formula 47]

(Xa)

with ethylene oxide to synthesize DIG-polyethylene glycol (DIG-PEG-OH) represented by the formula (Xb):

[Formula 48]

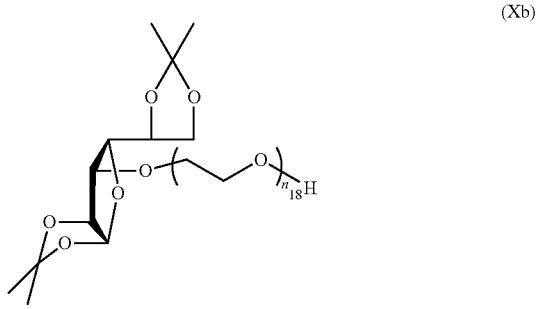

(Xb)

wherein $n_{18}$ is equal to $n_{10}$, (ii) substituting the OH group of the DIG-PEG-OH represented by the formula (Xb) by an amino group to obtain DIG-PEG-NH$_2$ represented by the formula (Xc):

[Formula 49]

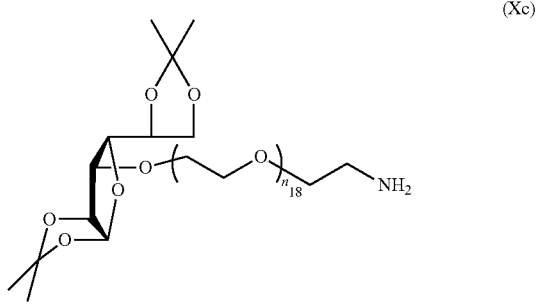

(Xc)

(iii) polymerizing β-benzyl-L-aspartate-N-carboxylic anhydride with the amino group of the DIG-PEG-NH$_2$, and
(iv) reacting the obtained compound with 1,5-diaminopentane (DAP), followed by the deprotection of the protective groups.

Likewise, Glc(2)-PEG-poly(anion) and Glc(2)-PEG-poly(cation) can also be appropriately synthesized by those skilled in the art. The Glc(2)-PEG-poly(anion) and the Glc(2)-PEG-poly(cation) can each be synthesized using glucose with OH groups, except for an OH group serving as a substituent on carbon at position 2, protected as a starting material, though the synthesis method is not limited thereto. The glucose with OH groups, except for an OH group serving as a substituent on carbon at position 2, protected may be obtained, for example, by using 1,3,4,6-tetra-O-acetyl-β-D-mannopyranose as a starting compound, protecting the OH group serving as a substituent on carbon at position 2 with a benzyl group, then alkali-hydrolyzing the acetyl group into an OH group, protecting the OH groups with silyl protective groups (e.g., TBS groups), then deprotecting the benzyl group with a palladium catalyst or a platinum catalyst and hydrogen gas, and sterically inverting the OH group serving as a substituent on carbon at position 2 through Mitsunobu reaction. Those skilled in the art could readily understand that synthesis can be carried out in the same way as in the production of Glc(3), Glc(6)-PEG-poly(anion), and Glc(2)-PEG-poly(anion) except that the molecule obtained above is used instead of BIG or DIG.

The present invention provides a method for producing a conjugate represented by the formula (XVI):

[Formula 50]

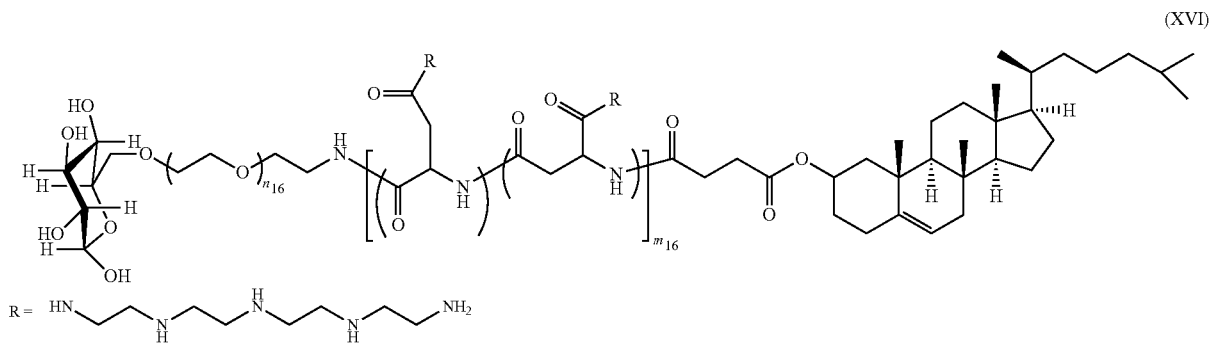

(XVI)

wherein $n_{16}$ and $m_{16}$ each represent 5 to 20,000, the method comprising:

(i) reacting 1,2-O-isopropylidene-α-D-glucofuranose represented by the formula (Ia):

[Formula 51]

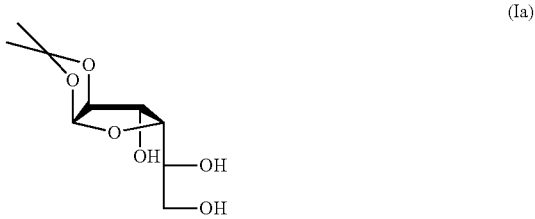

(Ia)

with benzaldehyde to obtain 1,2-O-isopropylidene-5,6-O-benzylidene-α-D-glucofuranose (BIG) represented by the formula (Ib):

[Formula 52]

(Ib)

(ii) reacting the BIG represented by the formula (Ib) with ethylene oxide to obtain BIG-polyethylene glycol (BIG-PEG-OH) represented by the formula (Ic):

[Formula 53]

(Ic)

wherein $n_{17}$ is equal to $n_1$, (iii) aminating the BIG-PEG-OH represented by the formula (Ic) to obtain BIG-PEG-NH$_2$ represented by the formula (Id):

[Formula 54]

(Id)

(iv) polymerizing β-benzyl-L-aspartate-N-carboxylic anhydride with the BIG-PEG-NH$_2$ represented by the formula (Id) to obtain BIG-PEG-PBLA, (v) reacting the BIG-PEG-PBLA with 4-cholesterylamino-4-butanoic acid to obtain BIG-PEG-PBLA-Chol represented by the formula (XVIa):

[Formula 55]

(XVIa)

and (vi) reacting the BIG-PEG-PBLA-Chol with tetraethylenepentamine (TEP) to obtain BIG-PEG-poly(Asp-TEP)-chol represented by the formula (XVIb):

[Formula 56]

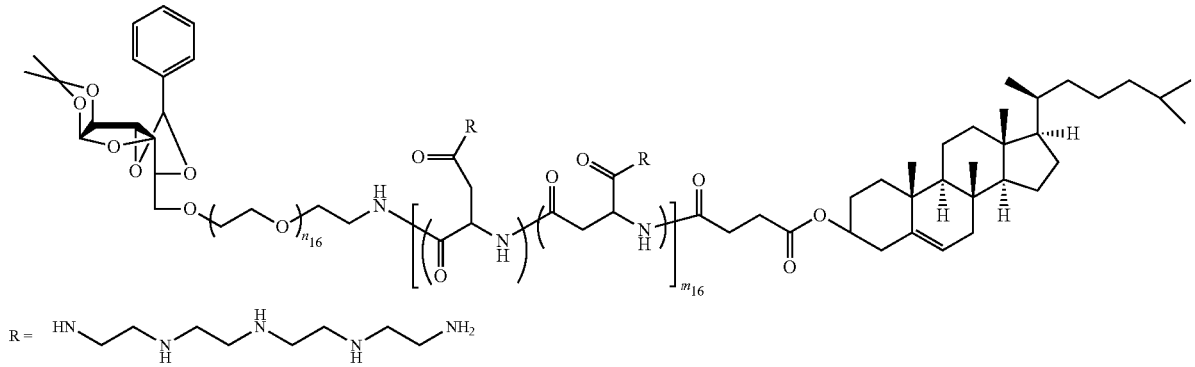

(XVIb)

followed by the deprotection of the protective groups.

The vesicle can be formed by a well-known method using any of the polymers described above. In general, the vesicle can be obtained by stirring a solution containing such a polymer dissolved at a concentration equal to or higher than a predetermined concentration. The vesicle formed on the basis of a polyion complex can be obtained by mixing a polymer having a polycation moiety and a polymer having a polyanion moiety at the same ratios. A method for allowing the vesicle to incorporate a drug is well-known to those skilled in the art, and such a well-known method can also be used in the present invention. For example, the PIC micelle can be allowed to incorporate a drug by forming the micelle and then adding the drug to the micelle solution. The drug is spontaneously incorporated through the charge thereof into the PIC micelle. In the case of, for example, PICsome, a drug is incorporated into the PICsome by preparing a mixed solution of a PICsome-forming polymer and the drug, followed by stirring and mixing. In the case of a liposome, a drug is also incorporated into the liposome by preparing a mixed solution of a liposome-forming polymer and the drug, followed by stirring and mixing. The anionic block and the cationic block in the polyion complex may be cross-linked. The cross-linking agent used for this purpose is not particularly limited, and, for example, 1-ethyl-3-(3-dimethylamino-propyl)carbodiimide hydrochloride (EDC) capable of condensing an amino group with a carboxy group can be preferably used.

When the ratio of the glucose-conjugated polymer to all polymers constituting the vesicle is 10 to 40%, the delivery efficiency of the composition to the brain parenchyma is particularly high. The ratio of the glucose-conjugated polymer to all polymers constituting the vesicle can be 10 to 40%, preferably 20 to 30%, more preferably 22 to 28%, further preferably 24 to 26% (e.g., approximately 25%). When the ratio of the glucose-conjugated molecule to all polymers constituting the vesicle is 40% or more, the delivery efficiency of the composition to cerebrovascular endothelial cells is particularly high. The ratio of the glucose-conjugated polymer to all polymers constituting the vesicle can be 40 to 100%, for example, 40 to 60%. In order to modify the outer surface of the vesicle with the GLUT1 ligand, the vesicle itself may be modified (e.g., glycosylated) with the GLUT1 ligand. From the viewpoint of controlling the ratio of modification with the GLUT1 ligand on the surface of the vesicle, it is preferred to conjugate each vesicle-forming polymer with the GLUT1 ligand in advance and adjust a mixing ratio between this polymer and a polymer unmodified with the GLUT1 ligand, followed by the formation of the vesicle with these polymers.

According to the present invention, a conjugate of a drug and a GLUT1 ligand can also be delivered to the brain by the blood glucose control of the present invention. The drug and the GLUT1 ligand may be conjugated via a linker. The linker can be a biocompatible linker, and, for example, polyethylene glycol can be used. The drug may be conjugated with two or more molecules of the GLUT1 ligand. These two or more molecules of the GLUT1 ligand can be preferably conjugated with the drug via linkers. In the case of conjugating two or more molecules of the GLUT1 ligand with the drug via linkers, for example, this conjugation can be achieved using a polyamino acid (e.g., polyaspartic acid) with side chains bound with a plurality of GLUT1 ligands. A linker such as PEG may intervene between the drug and the polyamino acid. For example, a compound represented by the following formula (XIX):

[Formula 57]

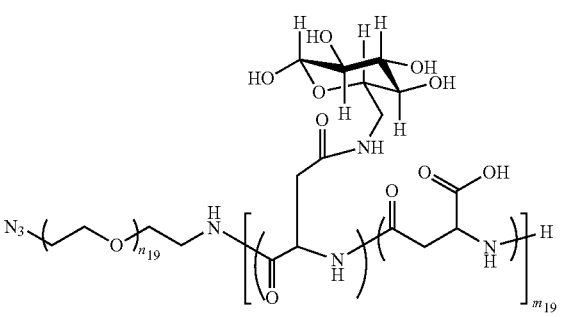

(XIX)

wherein $n_{19}$ represents an integer of 5 to 20,000, and $m_{19}$ represents an integer of 2 to 5,000 can be used as the polyamino acid (e.g., polyaspartic acid) with side chains bound with a plurality of GLUT1 ligands. $n_{19}$ is an integer of 5 to 20,000, preferably an integer of 10 to 5,000, more preferably an integer of 40 to 500, further preferably an integer of 5 to 1,000, still further preferably an integer of 10 to 200. $m_{19}$ is an integer of 2 to 20,000, preferably an integer of 2 to 5,000, more preferably an integer of 40 to 500, further preferably an integer of 5 to 1,000, still further preferably an integer of 10 to 200. In one embodiment, $n_{19}$ is 273, and $m_{19}$ is 48.

A copolymer of PEG and polyaspartic acid bound with a plurality of GLUT1 ligands can be synthesized as follows:

Scheme 2
[Formula 58]
Scheme 2
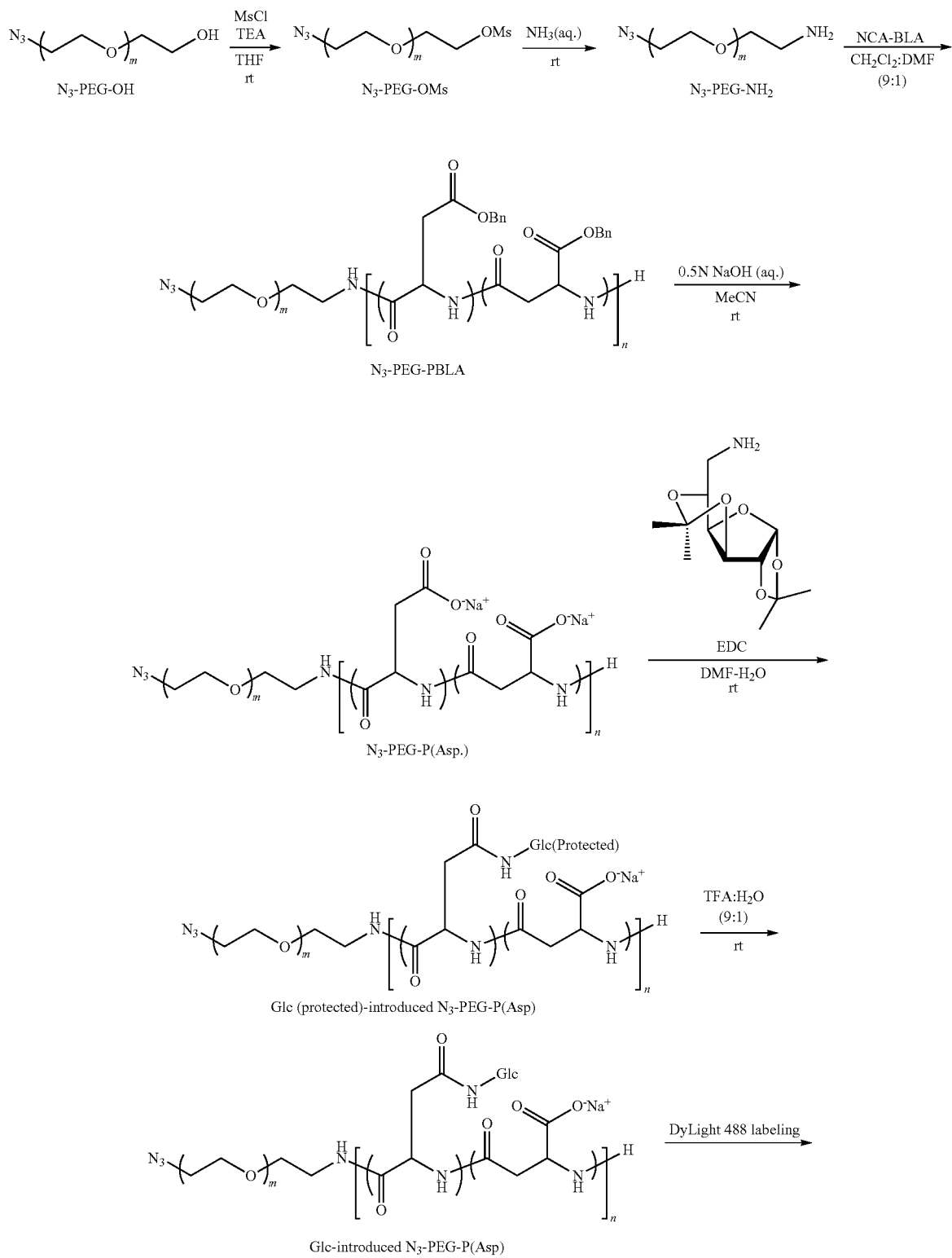

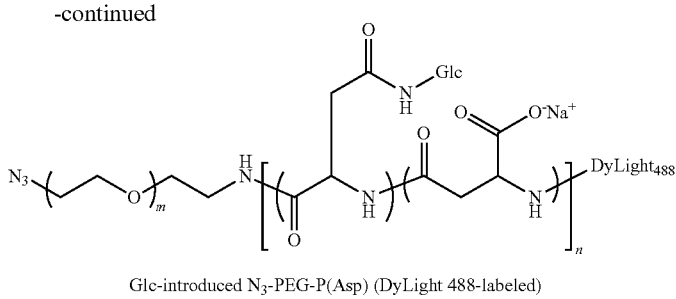

Glc-introduced N₃-PEG-P(Asp) (DyLight 488-labeled)

DMF represents N,N'-dimethylformamide; Bn represents a benzyl group; and EDC represents 1-ethyl-3-(3-dimethylaminopropyl)carbodiimide hydrochloride. Other abbreviations are as defined in the above schemes.

Hereinafter, scheme 2 will be described briefly. The compound represented by the formula (XIXa), which is a starting compound in scheme 2, can be obtained as follows:

[Formula 59]

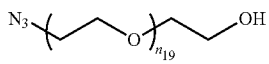
(XIXa)

wherein $n_{19}$ represents an integer of 5 to 20,000.

2-(2-Hydroxyethoxy)tetrahydropyran is reacted with ethylene oxide to obtain THP-PEG-OH. Next, the OH group of the THP-PEG-OH is mesylated using methanesulfonyl chloride or the like. The obtained MsO-PEG-THP is reacted with sodium azide to obtain polyethylene glycol of a tetrahydropyranyl group having an azide group at one end (N₃-PEG-THP). Then, the THP protective group is deprotected to obtain polyethylene glycol of a 3-hydroxypropyl group having an azide group at one end (N₃-PEG-OH) represented by the formula (XIXa). The degree of polymerization can be appropriately adjusted by the amount of ethylene oxide added.

After the obtainment of the compound represented by the formula (XIXa) as mentioned above, the OH group of the N₃-PEG-OH is aminated to obtain N₃-PEG-NH₂. The NH₂ group of the N₃-PEG-NH₂ is further reacted with β-benzyl-L-aspartate-N-carboxylic anhydride (BLA-NCA) to obtain N₃-PEG-PBLA. The protective groups are deprotected by alkali hydrolysis. The resulting product is reacted with 6-amino-6-deoxy-1,2:3,5-di-O-isopropylidene-α-D-glucofuranose (P-aminoglucose), which is protected aminoglucose, in the presence of EDC to condense the amino group of the aminoglucose with the carboxy group of the aspartic acid residue. Then, the protective groups are deprotected to obtain a block copolymer of polyethylene glycol having an azide group at one end and polyaspartic acid (N₃-PEG-P(Asp)).

The 6-amino-6-deoxy-1,2:3,5-di-O-isopropylidene-α-D-glucofuranose (P-aminoglucose) can be prepared on the basis of the description of, for example, Carbohydr. Res. 19, 197-210 (1971). According to Carbohydr. Res. 19, 197-210 (1971), the P-aminoglucose is obtained by the following scheme 3:

Scheme 3

[Formula 60]
Scheme 3

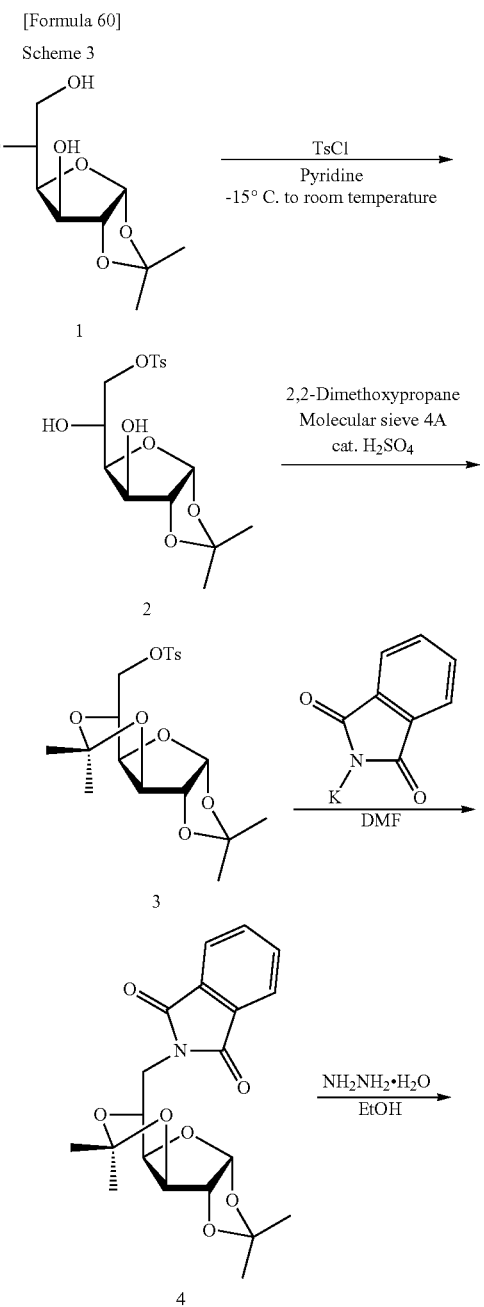

-continued

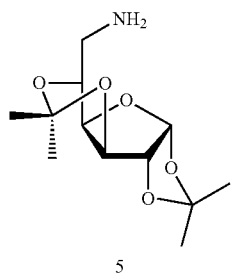
5

TsCl represents toluenesulfonyl chloride.

Hereinafter, scheme 3 will be described briefly. First, 1,2-O-isopropylidene-α-D-glucofuranose (1) is tosylated to obtain 1,2-O-isopropylidene-6-O-p-toluenesulfonyl-α-D-glucofuranose (2). Next, the obtained 1,2-O-isopropylidene-6-O-p-toluenesulfonyl-α-D-glucofuranose (2) is reacted with 2,2-dimethoxypropane to obtain 1,2:3,5-di-O-isopropylidene-6-O-p-toluenesulfonyl-α-D-glucofuranose (3). Then, the 1,2:3,5-di-O-isopropylidene-6-O-p-toluenesulfonyl-α-D-glucofuranose (3) is reacted with potassium phthalimide to obtain 6-deoxy-1,2:3,5-di-O-isopropylidene-6-phthalimido-α-D-glucofuranose (4). The 6-deoxy-1,2:3,5-di-O-isopropylidene-6-phthalimido-α-D-glucofuranose (4) can be reacted with hydrazine hydrate to obtain 6-amino-6-deoxy-1,2:3,5-di-O-isopropylidene-α-D-glucofuranose (P-aminoglucose) (5).

The present invention provides a method for producing a multi-glucose polymer represented by the formula (XIX):

[Formula 61]

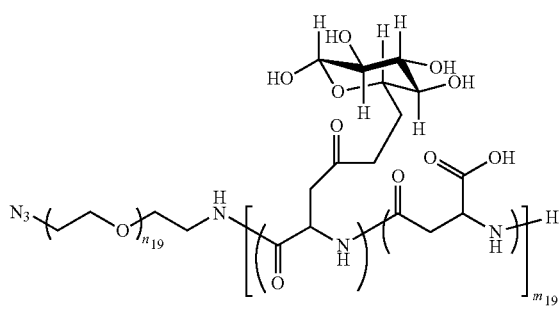
(XIX)

wherein $n_{19}$ represents an integer of 5 to 20,000, and $m_{19}$ represents an integer of 2 to 5,000, the method comprising:

(i) aminating the OH group of $N_3$-PEG-OH represented by the formula (XIXa):

[Formula 62]

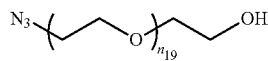
(XIXa)

to obtain $N_3$-PEG-$NH_2$ represented by the formula (XIXb):

[Formula 63]

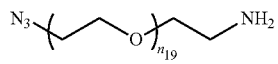
(XIXb)

(ii) reacting the obtained $N_3$-PEG-$NH_2$ with β-benzyl-L-aspartate-N-carboxylic anhydride to obtain $N_3$-PEG-PBLA represented by the formula (XIXc):

[Formula 64]

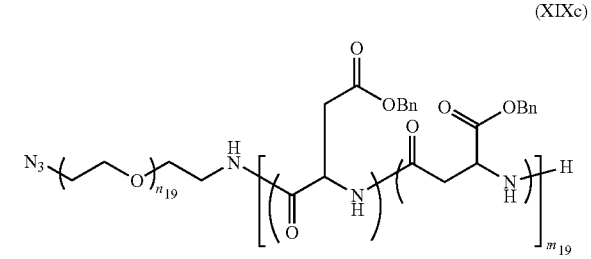
(XIXc)

wherein Bn represents a benzyl group serving as a protective group, (iii) deprotecting the protective groups in the obtained $N_3$-PEG-PBLA by alkali hydrolysis, and (iv) condensing the carboxy group of the obtained $N_3$-PEG-polyaspartic acid with the amino group of 6-amino-6-deoxy-1,2:3,5-di-O-isopropylidene-α-D-glucofuranose, followed by the deprotection of the protective groups on the OH groups.

The drug used in the present invention is not particularly limited, and any of a biologically active substance, an antibody, a nucleic acid, a biocompatible fluorescent dye, and a contrast medium such as a contrast medium for ultrasound, MRI, or CT can be used. According to the present invention, the drug can be delivered to the brain with high selectivity. Thus, for example, any of a biologically active substance that enhances the physiological functions of the brain, a biologically active substance capable of treating brain diseases, an antibody that recognizes an antigen characteristic of brain diseases, a nucleic acid that regulates the expression of a gene associated with brain diseases, a biocompatible fluorescent dye capable of staining the brain, and a contrast medium such as a contrast medium for ultrasound, MRI, or CT can be used as the drug, though the drug is not particularly limited thereto. The composition of the present invention containing, for example, a biologically active substance that enhances the physiological functions of the brain, a biologically active substance capable of treating brain diseases, an antibody that recognizes an antigen characteristic of brain diseases, or a nucleic acid that regulates the expression of a gene associated with brain diseases, as the drug can be provided as a pharmaceutical composition. The composition of the present invention containing a biocompatible fluorescent dye capable of staining the brain, or a contrast medium such as a contrast medium for ultrasound, MRI, or CT as the drug can be provided as a diagnostic drug.

The composition or the conjugate of the present invention may be administered as-is to the subject or may be administered thereto on the basis of the dosing regimen according to the present invention. The dosing regimen according to the present invention preferably involves first fasting the subject or causing the subject to have hypoglycemia, and then administering the composition to the subject. The dosing regimen according to the present invention more preferably comprises first fasting the subject or causing the subject to have hypoglycemia, and then administering the composition to the subject and inducing an increase in blood glucose level in the subject. In this context, in the dosing regimen according to the present invention, the administration of the composition to the subject is carried out simultaneously, consecutively, or successively with the induction of an increase in blood glucose level in the subject. The induction of a hypoglycemic state is probably useful for expressing GLUT1 on the inner surface of vascular endothelial cells (e.g., cerebrovascular endothelial cells). However, according to the present invention, the increase in blood glucose level in the recipient subject makes it very effective to deliver the composition or the conjugate of the present invention to the brain. According to the present invention, the composition (carrier, etc.) or the conjugate of the present invention can be delivered very effectively into the brain by raising the blood glucose level when the blood concentration of the composition (carrier, etc.) or the conjugate of the present invention in the subject who has been fasted or caused to have hypoglycemia is equal to or higher than a predetermined level. According to Examples of the present invention, the composition (carrier, etc.) or the conjugate of the present invention is delivered into the brain of the subject for a while even after the induction of an increase in blood glucose level in the subject.

From the viewpoint of keeping the blood concentration of the composition (carrier, etc.) or the conjugate of the present invention at a predetermined level or higher, it is preferred that the composition or the conjugate of the present invention should be administered in the form of an intravenous infusion to the subject. This facilitates securing the predetermined blood concentration of even a composition or a conjugate having a short blood retention time. For example, an siRNA micelle incorporating siRNA having a short blood retention time is more effective when administered in the form of an infusion to the subject. The infusion administration can be preferably carried out for 10 minutes or longer, 15 minutes or longer, 30 minutes or longer, 45 minutes or longer, 60 minutes or longer, 90 minutes or longer, or 2 hours or longer. The infusion administration is preferably carried out at a constant infusion speed. The administration at a constant infusion speed can be achieved using, for example, a precise dosing pump. The infusion administration may be carried out simultaneously with the induction of an increase in blood glucose level in the subject. Alternatively, an increase in blood glucose level may be induced in the subject during the infusion administration.

When the composition or the conjugate of the present invention is administered on the basis of the dosing regimen according to the present invention, the delivery efficiency thereof to the brain is selectively enhanced. Thus, the composition or the conjugate of the present invention can be used for delivering a drug to the brain. The composition or the conjugate of the present invention can also allow a drug to cross the blood-brain barrier. Thus, the composition or the conjugate of the present invention can be used for delivering a drug, for example, a biologically active substance, an antibody, a nucleic acid, a biocompatible fluorescent dye, or a contrast medium such as a contrast medium for ultrasound, MRI, or CT, to the brain parenchyma to which drug delivery has heretofore been difficult. The composition or the conjugate of the present invention can also allow a drug to be accumulated in cerebrovascular endothelial cells. Thus, the composition or the conjugate of the present invention can be used for delivering a drug, for example, a biologically active substance, an antibody, a nucleic acid, a biocompatible fluorescent dye, or a contrast medium such as a contrast medium for ultrasound, MRI, or CT, to cerebrovascular endothelial cells to which drug delivery has heretofore been difficult. The composition or the conjugate of the present invention can also be used for delivering a drug that weakens or destroys the adhesion between cerebrovascular endothelial cells to cerebrovascular endothelial cells. Likewise, the composition or the conjugate of the present invention can be used for delivering a drug, for example, a biologically active substance, an antibody, a nucleic acid, a biocompatible fluorescent dye, or a contrast medium such as a contrast medium for ultrasound, MRI, or CT, to the retina, the peripheral nerve, and/or cerebrospinal fluid. The composition or the conjugate of the present invention can also be used for delivering a drug, for example, a biologically active substance, an antibody, a nucleic acid, a biocompatible fluorescent dye, or a contrast medium such as a contrast medium for ultrasound, MRI, or CT, to vascular endothelial cells present in the blood-nerve barrier, the blood-retina barrier, or the blood-cerebrospinal fluid barrier. The composition or the conjugate of the present invention can also be used for delivering a drug that weakens or destroys the adhesion between vascular endothelial cells present in the blood-nerve barrier, the blood-retina barrier, or the blood-cerebrospinal fluid barrier to cerebrovascular endothelial cells. The adhesion between vascular endothelial cells is weakened or destroyed, whereby the functions of the barrier can be attenuated to allow various drugs to cross the barrier.

The composition and the conjugate of the present invention can be administered orally and parenterally (e.g., intravenously or intraperitoneally).

The present invention provides a method for targeting a brain tissue, comprising administering a carrier for drug delivery modified at the outer surface thereof with a GLUT1 ligand to a subject according to a dosing regimen. The present invention also provides a method for targeting a cerebrovascular endothelial cell, comprising administering a carrier for drug delivery modified at the outer surface thereof with a GLUT1 ligand to a subject according to a dosing regimen. The dosing regimen according to the present invention preferably comprises administering the carrier to a subject who has been fasted or caused to have hypoglycemia. The dosing regimen according to the present invention more preferably comprises administering the composition to a subject who has been fasted or caused to have hypoglycemia and inducing an increase in blood glucose level in the subject. Likewise, the present invention provides a method for targeting a peripheral nerve tissue, the retina, and/or cerebrospinal fluid, comprising administering a carrier for drug delivery modified at the outer surface thereof with a GLUT1 ligand to a subject according to a dosing regimen. The present invention also provides a method for targeting a vascular endothelial cell present in the blood-nerve barrier, the blood-retina barrier, or the blood-cerebrospinal fluid barrier, comprising administering a carrier for drug delivery modified at the outer surface thereof with a GLUT1 ligand to a subject according to a dosing regimen.

According to the present invention, a drug, for example, a biologically active substance, an antibody, a nucleic acid, a biocompatible fluorescent dye, or a contrast medium such as a contrast medium for ultrasound, MRI, or CT, can be incorporated in the carrier, whereby the drug incorporated in the carrier can be effectively delivered to the brain, a peripheral nerve tissue, the retina, and/or cerebrospinal fluid.

The present invention provides a method for targeting a brain tissue or a method for delivering a drug to a brain tissue, comprising administering a conjugate of the drug and a GLUT1 ligand or a conjugate comprising the drug and a GLUT1 ligand linked via a linker to a subject according to a dosing regimen. The present invention also provides a method for targeting a cerebrovascular endothelial cell, comprising administering a conjugate of the drug and a GLUT1 ligand or a conjugate comprising the drug and a GLUT1 ligand linked via a linker to a subject according to a dosing regimen. The dosing regimen according to the present invention preferably comprises administering the composition to a subject has been fasted or caused to have hypoglycemia. The dosing regimen according to the present invention more preferably comprises administering the composition to a subject has been fasted or caused to have hypoglycemia and inducing an increase in blood glucose level in the subject. Likewise, the present invention provides a method for targeting a peripheral nerve tissue, the retina, and/or cerebrospinal fluid, comprising administering a conjugate of the drug and a GLUT1 ligand or a conjugate comprising the drug and a GLUT1 ligand linked via a linker to a subject according to a dosing regimen. The present invention also provides a method for targeting a vascular endothelial cell present in the blood-nerve barrier, the blood-retina barrier, or the blood-cerebrospinal fluid barrier, comprising administering a conjugate of the drug and a GLUT1 ligand or a conjugate comprising the drug and a GLUT1 ligand linked via a linker to a subject according to a dosing regimen.

According to the present invention, a drug, for example, a biologically active substance, an antibody, a nucleic acid, a biocompatible fluorescent dye, or a contrast medium such as a contrast medium for ultrasound, MRI, or CT, can be used as the drug contained in the conjugate, whereby the drug can be effectively delivered to the brain, a peripheral nerve tissue, the retina, and/or cerebrospinal fluid.

According to the present invention, a therapeutic drug or a prophylactic drug for brain diseases can be used as the drug. In this case, the present invention provides a method for treating or preventing a brain disease, comprising administering a carrier for drug delivery modified at the outer surface thereof with a GLUT1 ligand and incorporating a therapeutic drug or a prophylactic drug for the brain disease, to a subject in need thereof according to a dosing regimen. Likewise, the present invention provides a method for treating or preventing a brain disease, comprising administering a carrier for drug delivery modified at the outer surface thereof with a GLUT1 ligand and incorporating a therapeutic drug or a prophylactic drug for the peripheral nerve disease, to a subject in need thereof according to a dosing regimen. Likewise, the present invention provides a method for treating or preventing a brain disease, comprising administering a carrier for drug delivery modified at the outer surface thereof with a GLUT1 ligand and incorporating a therapeutic drug or a prophylactic drug for the retinal disease, to a subject in need thereof according to a dosing regimen. The dosing regimen according to the present invention preferably comprises administering the composition to a subject who has been fasted or caused to have hypoglycemia. The dosing regimen according to the present invention more preferably comprises administering the composition to a subject who has been fasted or caused to have hypoglycemia and inducing an increase in blood glucose level in the subject.

According to the present invention, a therapeutic drug or a prophylactic drug for brain diseases can be used as the drug. In this case, the present invention provides a method for treating or preventing a brain disease, comprising administering a conjugate of a therapeutic drug or a prophylactic drug for the brain disease and a GLUT1 ligand or a conjugate comprising a therapeutic drug or a prophylactic drug for the brain disease and a GLUT1 ligand linked via a linker, to a subject in need thereof according to a dosing regimen. Likewise, the present invention provides a method for treating or preventing a peripheral nerve disease, comprising administering a conjugate of a therapeutic drug or a prophylactic drug for the peripheral nerve disease and a GLUT1 ligand or a conjugate comprising a therapeutic drug or a prophylactic drug for the peripheral nerve disease and a GLUT1 ligand linked via a linker, to a subject in need thereof according to a dosing regimen. Likewise, the present invention provides a method for treating or preventing a retinal disease, comprising administering a conjugate of a therapeutic drug or a prophylactic drug for the retinal disease and a GLUT1 ligand or a conjugate comprising a therapeutic drug or a prophylactic drug for the retinal disease and a GLUT1 ligand linked via a linker, to a subject in need thereof according to a dosing regimen. The dosing regimen according to the present invention preferably comprises administering the composition to a subject who has been fasted or caused to have hypoglycemia. The dosing regimen according to the present invention more preferably comprises administering the composition to a subject who has been fasted or caused to have hypoglycemia and inducing an increase in blood glucose level in the subject.

Thus, the present invention provides a pharmaceutical composition for treating or preventing a brain disease, comprising a therapeutic drug or a prophylactic drug for the brain disease. According to the present invention, the uptake of the drug to the brain is improved. Thus, it is obvious that the pharmaceutical composition of the present invention is useful in the treatment or prevention of brain diseases. The present invention also provides a pharmaceutical composition for use in treating or preventing a peripheral nerve disease, comprising a therapeutic drug or a prophylactic drug for the peripheral nerve disease. According to the present invention, the uptake of the drug to the peripheral nerve is improved. Thus, it is obvious that the pharmaceutical composition of the present invention is useful in the treatment or prevention of peripheral nerve diseases. The present invention further provides a pharmaceutical composition for use in treating or preventing a retinal disease, comprising a therapeutic drug or a prophylactic drug for the retinal disease. According to the present invention, the uptake of the drug to the retina is improved. Thus, it is obvious that the pharmaceutical composition of the present invention is useful in the treatment or prevention of retinal diseases. According to the present invention, each of the therapeutic drugs or the prophylactic drugs mentioned above may be contained in the composition in a form incorporated in the carrier or may be contained in the composition in a form conjugated with the GLUT1 ligand via or without a linker.

Examples of the brain disease include brain diseases that can be treated by allowing therapeutic drugs for brain diseases to cross the blood-brain barrier, for example, anxiety, depression, sleep disorder, Alzheimer's disease, Parkinson's disease, and multiple sclerosis. Thus, in the present invention, therapeutic drugs or prophylactic drugs for brain diseases, such as antianxiety drugs, antidepressants, sleep inducing drugs, therapeutic drugs for Alzheimer's disease, therapeutic drugs for Parkinson's disease, and therapeutic drugs for multiple sclerosis can be used for treating these brain diseases. For example, Aβ antibodies are well-known as the therapeutic drugs for Alzheimer's disease. For example, dopamine receptor agonists and L-dopa are well-known as the therapeutic drugs for Parkinson's disease. For example, adrenal steroids, interferon β (IFNβ), and immunosuppressants are well-known as the therapeutic drugs for multiple sclerosis. Any of these therapeutic drugs can be used in the present invention. Examples of the peripheral nerve disease include peripheral nerve diseases that can be treated by allowing therapeutic drugs for peripheral nerve diseases to cross the blood-brain barrier, for example, Guillain-Barre syndrome, Fisher syndrome, and chronic inflammatory demyelinating polyneuropathy. Examples of the retinal disease include retinal diseases that can be treated by allowing therapeutic drugs for retinal diseases to cross the blood-brain barrier, for example, retinitis pigmentosa, gyrate atrophy of the choroid and retina, choroideremia, Bietti crystalline retinopathy, congenital amaurosis, congenital stationary night blindness, Oguchi disease, fundus albipunctatus, retinopathy *punctata albescens*, pigmented paravenous retinochoroidal atrophy, Stargardt's disease, vitelliform macular dystrophy, K-linked juvenile retinoschisis, central areolar choroidal dystrophy, occult macular dystrophy, familial exudative vitreoretinopathy, and angioid streaks.

EXAMPLES

Example 1: Preparation of Glc(6)-PIC Micelle

In Example 1, a polymer necessary for micelle formation was synthesized.

1-1. Synthesis of Glc(6)-PEG-P(Asp)

First, 1,2-O-isopropylidene-5,6-O-benzylidene-α-D-glucofuranose (hereinafter, referred to as "BIG-OH") was synthesized. Specifically, 10 g of 1,2-O-isopropylidene-α-D-glucofuranose (hereinafter, referred to as "MIG") (manufactured by Wako Pure Chemical Industries, Ltd.) and 40 mL of benzaldehyde were mixed in a flask and reacted by mixing under rotation for 4 hours in a rotary evaporator. After the reaction, 66 mL of ethyl acetate was added thereto, and the reaction mixture was washed with 120 mL of distilled water. Only the organic layer (ethyl acetate layer) was recovered, added to 500 mL of hexane, and recrystallized at 0° C. to obtain 9.2 g of BIG-OH (yield: 85%).

Next, BIG-polyethylene glycol (BIG-PEG-OH) was synthesized from the obtained BIG-OH. Specifically, in order to uniformly attach BIG to the glass wall of a reaction vessel, the compound was freeze-dried over benzene and then dried under reduced pressure overnight at 70° C. 0.72 g of the resulting BIG-OH was dissolved in 5 mL of tetrahydrofuran (THF). In this way, a gel permeation chromatogram having a unimodal peak with a constant molecular weight was obtained (data not shown). 3.3 mL of a THF solution containing 0.3 M potassium naphthalene was added dropwise to the BIG-OH solution, then 2.2 mL of ethylene oxide (EO) was added thereto in an argon atmosphere, and the mixture was reacted at ordinary temperature for 48 hours. Then, 1 mL of methanol was added to the reaction solution, and the mixture was reprecipitated with cold ether containing 10% methanol to recover 2.8 g of BIG-PEG-OH (yield: 89%).

The OH group of the obtained BIG-PEG-OH was further aminated to synthesize BIG-PEG-NH$_2$ having an aminoethyl group. Specifically, 2.0 g of the benzene-freeze-dried BIG-PEG-OH is dissolved 20 mL of a THF solution containing 0.8 mL of triethylamine dissolved therein. A solution containing 570 mg of methanesulfonyl chloride dissolved in 20 mL of cold THF was added to the BIG-PEG-OH solution, and the mixture was stirred overnight at room temperature. The precipitated salt was removed by filtration, and the filtrate was reprecipitated with 500 mL of a freezing mixture containing diethyl ether containing 10% methanol, then filtered, and then dried under reduced pressure. The obtained powder was dissolved in 100 mL of a 25% aqueous ammonia solution, and the solution was reacted at room temperature for 2 days. The reaction solution was dialyzed against an aqueous ammonium solution diluted 2000-fold using a dialysis membrane (molecular weight cutoff: 1,000) and then dialyzed against pure water. Then, a fraction in which the amination did not proceed was removed using Sephadex C-25 (GE Healthcare Japan Corp.), and the residue was freeze-dried to recover 1.6 g of BIG-PEG-NH$_2$ (yield: 85%). No peak attributed to impurities was observed in the H$^1$ NMR spectrum of BIG-PEG-NH$_2$ after purification (data not shown).

BIG-PEG-poly(β-benzyl-L-aspartate) (hereinafter, referred to as "BIG-PEG-PBLA") was further synthesized from the obtained BIG-PEG-NH$_2$. Specifically, 1.7 g of β-benzyl-L-aspartate-N-carboxylic anhydride (hereinafter, referred to as "BLA-NCA") was dissolved in 3.5 mL of DMF, and the solution was diluted with 30 mL of dichloromethane. 200 mg of the benzene-freeze-dried BIG-PEG-NH$_2$ was dissolved in 4 mL of dichloromethane, and the solution was added to the BLA-NCA solution, followed by polymerization at 35° C. for 40 hours in the presence of argon. After the completion of the polymerization reaction was confirmed by IR analysis, the reaction mixture was added dropwise to 500 mL of hexane/ethyl acetate=6:4, and the precipitated polymer was recovered by suction filtration and dried in vacuum to obtain 1.39 g of BIG-PEG-PBLA (yield: 58%). The obtained BIG-PEG-PBLA exhibited a gel permeation chromatogram having a unimodal peak with a constant molecular weight (data not shown).

BIG-PEG-polyaspartic acid (hereinafter, referred to as "BIG-PEG-P(Asp.)") was further synthesized from the obtained BIG-PEG-PBLA. 500 mg of the BIG-PEG-PBLA was suspended in 0.5 N sodium hydroxide, while benzyl ester is hydrolyzed at room temperature. After dissolution of the copolymer, the reaction solution was dialyzed in water using a dialysis membrane (molecular weight cutoff: 1,000). The intramembrane solution was freeze-dried to obtain 132 mg of BIG-PEG-P(Asp.) (yield: 68%).

Then, Glc(6)-PEG-P(Asp.) was synthesized from the BIG-PEG-P(Asp.). In this context, Glc(6) means that glucose is conjugated via carbon at position 6 thereof with PEG. 100 mg of the BIG-PEG-P(Asp.) was dissolved in 10 mL of trifluoroacetic acid/pure water (8:2), and the solution was reacted for 1 hour. The reaction solution was dialyzed against 0.01 N NaOH and pure water in this order using a dialysis membrane (molecular weight cutoff: 1,000). The intramembrane solution was freeze-dried to obtain 70 mg of Glc(6)-PEG-P(Asp.) (yield: 70%).

1-2. Synthesis of PEG-P(Asp) and PEG-P(Asp.-AP)

First, a polyethylene glycol-poly(β-benzyl-L-aspartate) block copolymer (PEG-PBLA) was obtained by the polymerization of β-benzyl-L-aspartate-N-carboxylic anhydride (BLA-NCA) (obtained by contract manufacture by Chuo Kaseihin Co., Inc.). Specifically, 18.9 g of BLA-NCA is dissolved in 20 mL of N,N'-dimethylformamide (DMF). 2.0 g of polyethylene glycol having a methoxy group terminus and an aminoethyl group terminus (PEG-NH$_2$) (molecular weight: 2,000) was dissolved in 20 mL of DMF, and the solution is added to the BLA-NCA solution. The mixed solution was kept at 35° C., while polymerization was carried out for 40 hours. After the completion of the polymerization reaction was confirmed by IR analysis, the reaction mixture was added dropwise to 2 L of diethyl ether, and the precipitated polymer was recovered by suction filtration, washed with diethyl ether, and then dried in vacuum to obtain 15.51 g of PEG-PBLA (yield: 79%).

Next, a polyethylene glycol-polyaspartic acid block copolymer (PEG-P(Asp.)) was synthesized from the PEG-PBLA. Specifically, 1.0 g of the PEG-PBLA was suspended in 0.5 N sodium hydroxide, while benzyl ester was hydrolyzed at room temperature. After dissolution of the copolymer, the reaction solution was dialyzed in water using a dialysis membrane (molecular weight cutoff: 6,000-8,000). The intramembrane solution was freeze-dried to obtain 654 mg of PEG-P(Asp.) (yield: 78%).

Next, a polyethylene glycol-poly((5-aminopentyl)-aspartic acid) block copolymer (PEG-P(Asp.-AP)) was synthesized from the PEG-PBLA. Specifically, 1 g of the benzene-freeze-dried PEG-PBLA is dissolved in 10 mL of DMF. 8 mL of 1,5-diaminopentane (DAP) was added to the PEG-PBLA solution. The mixed solution was kept at 5° C., while reaction was carried out for 1 hour. Then, 15.2 mL of an aqueous solution containing 20% by weight of acetic acid was added to the reaction solution, and the mixture was dialyzed in water using a dialysis membrane (molecular weight cutoff: 6,000-8,000). The intramembrane solution was freeze-dried to obtain 954 mg of PEG-P(Asp.-AP) (yield: 81%).

1-3. Synthesis of Fluorescently Labeled Polymer Cy5-PEG-P(Asp.)

500 mg of the PEG-PBLA thus obtained was dissolved in 20 mL of dimethyl sulfoxide (DMSO). 25 mg of sulfo-type Cy5-N-hydroxysuccinimide ester (manufactured by Lumiprobe GmbH, product No: 43320) was added to the PEG-PBLA solution, and the mixture was reacted at ordinary temperature for 2 days. Then, 75 mL of 0.5 N sodium hydroxide was added thereto, and benzyl ester was hydrolyzed at room temperature. The reaction solution was dialyzed against ethanol and water in this order using a dialysis membrane (molecular weight cutoff: 6,000-8,000). The intramembrane solution was freeze-dried to obtain 456 mg of Cy5-PEG-P(Asp.) (yield: 86%).

1-4. Synthesis of Glc(3)-PEG-P(Asp)

First, DIG-PEG-OH was obtained from benzene-freeze-dried 1,2,5,6-di-O-isopropylidene-α-D-glucofuranose (DIG). Specifically, 0.72 g of DIG (manufactured by Tokyo Chemical Industry Co., Ltd. (TCI)) was dissolved in 5 mL of THF to obtain a DIG-OH solution. Then, 3.5 mL of a THF solution containing 0.3 M potassium naphthalene was added dropwise to the obtained DIG-OH solution, then 2.5 mL of ethylene oxide (EO) was added thereto in an argon atmosphere, and the mixture was reacted at ordinary temperature for 48 hours. Then, 1 mL of methanol was added to the reaction solution, and the mixture was reprecipitated with freezing mixture-well cold ether containing 10% methanol to recover 3.2 g of DIG-PEG-OH (yield: 86%).

Next, the obtained DIG-PEG-OH was aminated to obtain DIG-PEG-NH$_2$. Specifically, 3.2 g of the benzene-freeze-dried DIG-PEG-OH is dissolved in 32 mL of a THF solution containing 0.8 mL of triethylamine dissolved therein. A solution containing 912 mg of methanesulfonyl chloride dissolved in 32 mL of cold THF was added to the DIG-PEG-OH solution, and the mixture was reacted overnight at room temperature. The precipitated salt was removed by filtration, and the filtrate was reprecipitated with 500 mL of a freezing mixture containing diethyl ether containing 10% methanol, then filtered, and then dried under reduced pressure. The obtained powder was dissolved in 100 mL of a 25% aqueous ammonia solution, and the solution was reacted at room temperature for 2 days. The reaction solution was dialyzed against an aqueous ammonium solution diluted 2000-fold and pure water in this order using a dialysis membrane (molecular weight cutoff: 1,000). Then, a fraction in which the amination did not proceed was removed through Sephadex C-25 (GE Healthcare Japan Corp.), and the residue was freeze-dried to recover 2.95 g of DIG-PEG-NH$_2$ (yield: 89%).

DIG-PEG-PBLA was further synthesized from the obtained DIG-PEG-NH$_2$. Specifically, 1.7 g of BLA-NCA was dissolved in 3.5 mL of DMF, and the solution was diluted with 30 mL of dichloromethane. 200 mg of the benzene-freeze-dried DIG-PEG-NH$_2$ was dissolved in 4 mL of dichloromethane, and the solution was added to the BLA-NCA solution, followed by polymerization at 35° C. for 40 hours in the presence of argon. After the completion of the polymerization reaction was confirmed by IR analysis, the reaction mixture was added dropwise to 500 mL of hexane/ethyl acetate (hexane:ethyl acetate=6:4), and the precipitated polymer was recovered by suction filtration and dried in vacuum to obtain 1.32 g of DIG-PEG-PBLA (yield: 70%).

DIG-PEG-polyaspartic acid (DIG-PEG-P(Asp.)) was further synthesized from the obtained DIG-PEG-PBLA. Specifically, 500 mg of the DIG-PEG-PBLA was suspended in 0.5 N sodium hydroxide, while benzyl ester is hydrolyzed at room temperature. After dissolution of the copolymer, the reaction solution was dialyzed in water using a dialysis membrane (molecular weight cutoff: 1,000). The intramembrane solution was freeze-dried to obtain 145 mg of DIG-PEG-P(Asp.) (yield: 54%).

Glc(3)-PEG-P(Asp.) was further synthesized from the obtained DIG-PEG-P(Asp.). In this context, Glc(3) means that glucose is conjugated via carbon at position 3 thereof with PEG. Specifically, 100 mg of the DIG-PEG-P(Asp.) was dissolved in 10 mL of trifluoroacetic acid/pure water (trifluoroacetic acid:water=8:2), and the solution was reacted for 1 hour. The reaction solution was dialyzed against 0.01 N NaOH and pure water in this order using a dialysis membrane (molecular weight cutoff: 1,000). The intramembrane solution was freeze-dried to obtain 75 mg of Glc(3)-PEG-P(Asp.) (yield: 86%).

1-5. Preparation of Cy5-PIC Micelle 50 mg of Cy5-PEG-P(Asp.) was dissolved in 50 mL of a 10 mM phosphate buffer solution (PB, pH 7.4, 0 mM NaCl) to prepare a 1 mg/mL Cy5-PEG-P(Asp.) solution. 50 mg of PEG-P(Asp.-AP) was similarly dissolved in 50 mL of PB to prepare a 1 mg/mL PEG-P(Asp.-AP) solution. These two types of aqueous solutions containing the Cy5-PEG-P(Asp.) or the PEG-P(Asp.-AP) were added at 4 mL and 7.0 mL, respectively, to a 50 mL conical tube and stirred for 2 minutes by vortex (2000 rpm). Then, 5.6 mL of a PB solution containing a water-soluble condensing agent 1-ethyl-3-(3-dimethylaminopropyl)carbodiimide hydrochloride (EDC) (10 mg/mL) was added thereto, and the tube was left standing overnight to cross-link the core of a polyion complex. Then, polymers that were not involved in micelle formation, and EDC by-products, etc. were removed using an ultrafiltration tube equipped with a membrane having a molecular weight cutoff of 100,000.

1-6. Characterization of Obtained Cy5-PIC Micelle

The size (Z-average particle size) and polydispersity index (PDI) of the obtained Cy5-PIC micelle were measured using Zetasizer (Malvern Instruments Ltd.). The size was determined by measuring the diffusion of particles moving by the Brownian movement and converting the measurement results to a particle size and a particle size distribution according to the Stokes-Einstein equation. The shape of the micelle was evaluated using a transmission electron microscope (TEM, JEM-1400). In this context, the Z-average particle size is data obtained by analyzing dynamic light scattering measurement data such as particle dispersions using the cumulant analysis method. In the cumulant analysis, an average particle size and a polydispersity index (PDI) are obtained. In the present invention, this average particle size is defined as the Z-average particle size. To be exact, a procedure of fitting a polynomial to the logarithm of a G1 correlation function obtained by measurement is referred to as the cumulant analysis. A constant b in the following expression:

$$LN(G1)=a+bt+ct^2+dt^3+et^4+\ldots$$

is called secondary cumulant or Z-averaged diffusion coefficient. The value of the Z-averaged diffusion coefficient is converted to a particle size using the viscosity of a dispersion medium and some apparatus constants, and the resulting value is the Z-average particle size and is suitable as an index for dispersion stability for the purpose of quality control.

1-7. Preparation of Glc(6)-Cy5-PIC Micelle 20 mg of Glc(6)-PEG-P(Asp.) and 40 mg of Cy5-PEG-P(Asp.) were dissolved in 60 mL of a 10 mM phosphate buffer solution (PB, pH 7.4, 0 mM NaCl) to prepare a 1 mg/mL mixed solution of Cy5-Glc(6)-PEG-P(Asp.) and PEG-P(Asp.). 50 mg of PEG-P(Asp.-AP) was similarly dissolved in 50 mL of PB to prepare a 1 mg/mL PEG-P(Asp.-AP) solution. These two types of aqueous solutions, i.e., the mixed solution of Cy5-PEG-P(Asp.) and PEG-P(Asp.) and the PEG-P(Asp.-AP) solution, were added at 4 mL and 7.0 mL, respectively, to a 50 mL conical tube and stirred for 2 minutes by vortex (2000 rpm). Then, 5.6 mL of a PB solution containing a water-soluble condensing agent EDC (10 mg/mL) was added thereto, and the tube was left standing overnight to cross-link the core of a polyion complex. Then, polymers that were not involved in micelle formation, and EDC by-products, etc. were removed using an ultrafiltration tube equipped with a membrane having a molecular weight cutoff of 100,000.

1-8. Characterization of Glc(6)-Cy5-PIC Micelle

Figure 2:
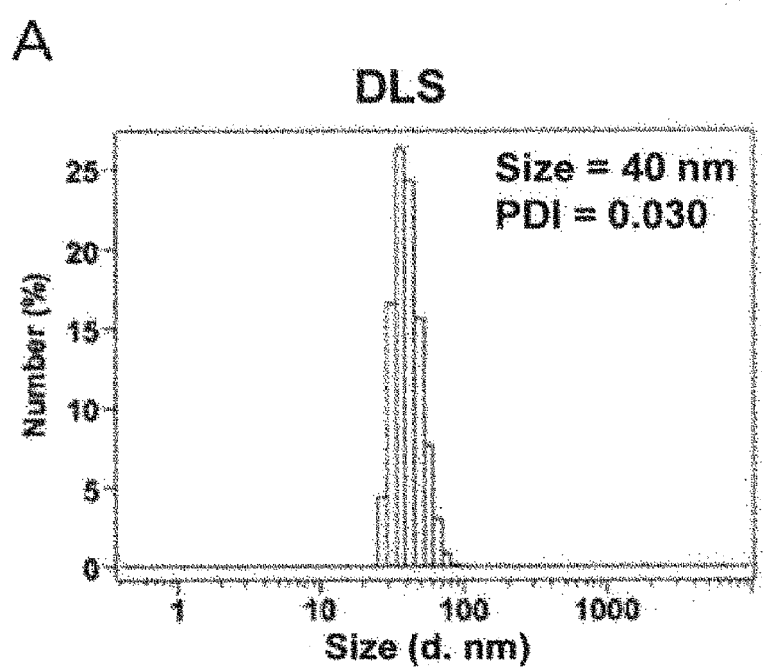
FIG. 2 shows results of dynamic light scattering measurement (DLS) of the particle size distribution of a Glc(6)-Cy5-PIC micelle obtained in Example 1, and a particle image taken under a transmission electron microscope (TEM). In this context, Glc(6) represents that glucose is conjugated via carbon at position 6 with a polymer constituting the micelle.

The size (Z-average particle size) and polydispersity index (PDI) of the obtained Glc(6)-Cy5-PIC micelle were measured using Zetasizer (Malvern Instruments Ltd.). As a result, the average particle size was 40 nm, demonstrating that a micelle having a uniform particle size was obtained (FIG. 2A). The shape of the micelle was observed using a transmission electron microscope (TEM, JEM-1400) after staining with uranyl acetate (FIG. 2B).

1-9. Preparation of Glc(3)-Cy5-PIC Micelle 20 mg of Glc(3)-PEG-P(Asp.) and 40 mg of Cy5-PEG-P(Asp.) were dissolved in 60 mL of a 10 mM phosphate buffer solution (PB, 0 mM NaCl) of pH 7.4 to prepare a 1 mg/mL mixed solution of Cy5-Glc(3)-PEG-P(Asp.) and PEG-P(Asp.). 50 mg of PEG-P(Asp.-AP) was similarly dissolved in 50 mL of PB to prepare a 1 mg/mL PEG-P(Asp.-AP) solution. These two types of aqueous solutions, i.e., the mixed solution of Cy5-PEG-P(Asp.) and PEG-P(Asp.) and the PEG-P(Asp.-AP) solution, were added at 4 mL and 4.3 mL, respectively, to a 50 mL conical tube and stirred for 2 minutes by vortex (2000 rpm). Then, 5.6 mL of a PB solution containing a water-soluble condensing agent EDC (10 mg/mL) was added thereto, and the tube was left standing overnight to cross-link the core of a polyion complex. Then, polymers that were not involved in micelle formation, and EDC by-products, etc. were removed using an ultrafiltration tube equipped with a membrane having a molecular weight cutoff of 100,000. The size (Z-average particle size) and polydispersity index (PDI) of the obtained Glc(6)-Cy5-PIC micelle were measured using Zetasizer (Malvern Instruments Ltd.). The shape of the micelle was evaluated using a transmission electron microscope (TEM, JEM-1400). The obtained micelle had a diameter of 32 nm (PDI=0.043) (data not shown).

Example 2: Pharmacokinetic Evaluation Experiment of PIC Micelle

Each micelle prepared in Example 1 was intravenously administered to mice and examined for the pharmacokinetics thereof. The effect of blood glucose control was additionally evaluated in the administration of the micelle.

In Examples below, accumulation in the brain was evaluated on the basis of the amount (%) of a micelle, etc., accumulated per g of the brain with respect to the total dose.

Each micelle solution described above (i.e., the Glc(6)-Cy5-PIC micelle, Glc(3)-Cy5-PIC micelle, or Cy5-PIC micelle solution (concentration: 1 mg/mL)) having a volume of 200 μL was intravenously administered (i.v.) at a dose of 200 μL to each of 24-hour fasted mice (Balb/c, female, 6 weeks old) and freely fed mice. In this context, the concentration 1 mg/mL is a value determined as a result of measuring fluorescence derived from Cy5 bound with each polyanion using NanoDrop. The fasted mouse group was refed 6 hours after the micelle solution administration. After a lapse of a predetermined time, the abdomen of each mouse was opened under anesthesia. Then, blood was collected from the abdominal aorta, and the brain, the liver, the spleen, the kidney, the heart, the lung, and the thigh muscle were further taken out thereof. The collected blood was centrifuged at 15,000 rpm at 4° C. for 5 minutes to prepare plasma, which was then dispensed to wells of a 96-well plate (Thermo Fisher Scientific Inc., USA). The micelle concentration in blood was determined from the fluorescence intensity of the plasma by fluorophotometry using Tecan Infinite M1000 PRO. In this operation, the blood of mice that were not given the sample was used as a control. On the hypothesis that the amount of plasma would be 55% in 2 mL of the whole blood of each mouse, the drug was evaluated for the pharmacokinetics thereof. A lysis buffer solution and a metal cone were added to each of the brain, the liver, the spleen, the kidney, the heart, the lung, and the thigh muscle, and suspensions thereof were prepared by homogenization and each dispensed to wells of a 96-well plate (Thermo Fisher Scientific Inc., USA). The accumulation efficiency (%) of the micelle in each organ was determined by fluorophotometry using Tecan Infinite M1000 PRO.

Figure 3:
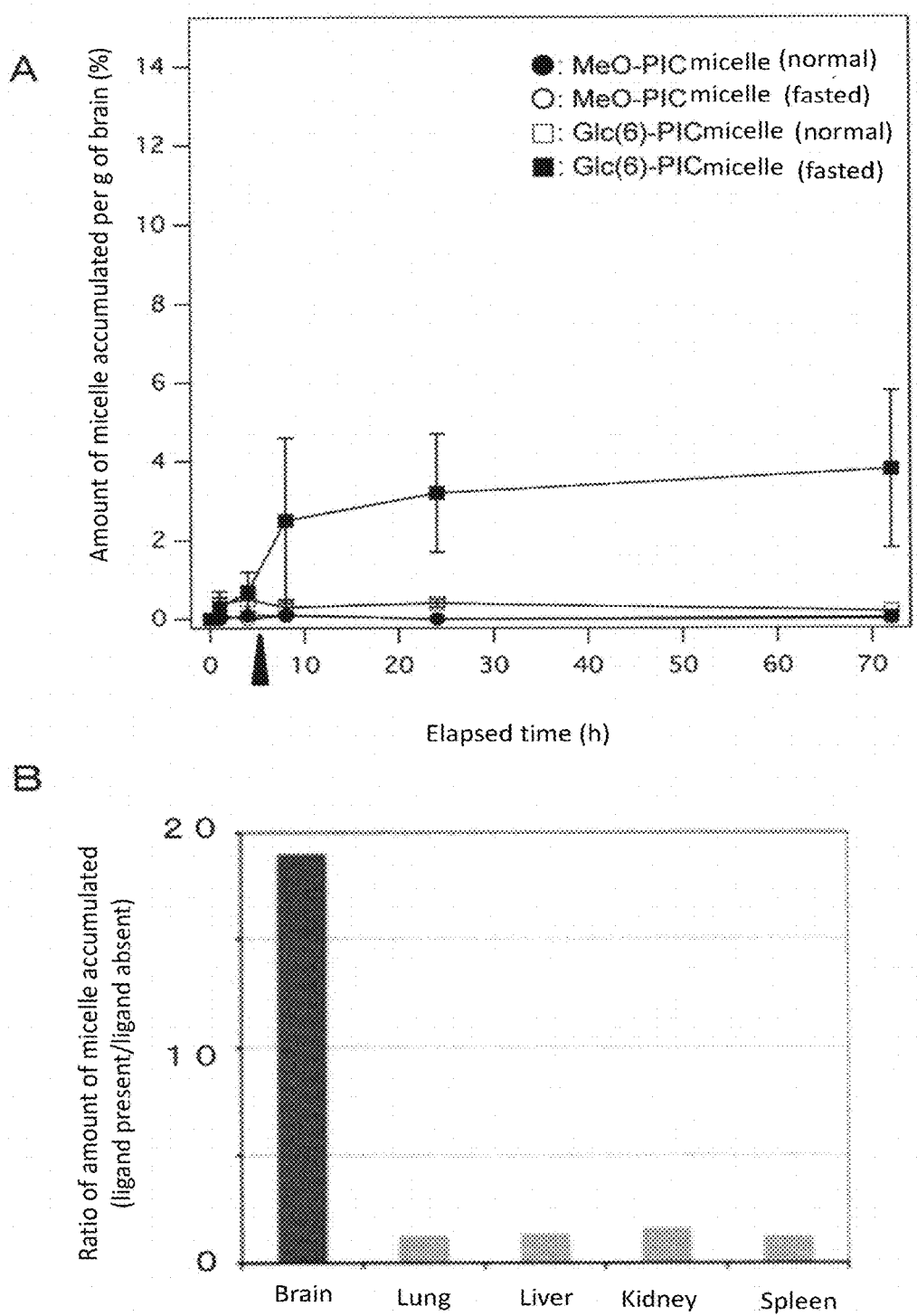
FIG. 3 is a diagram showing the selective and effective accumulation of the Glc(6)-Cy5-PIC micelle obtained in Example 1 in the brain.

As a result, when the micelle modified at the outer surface thereof with glucose via carbon at position 6 thereof (Glc (6)-PIC micelle) was administered to the fasted mice, the amount of the micelle accumulated in the brain was significantly increased at the same time with refeeding, and approximately 3.8% at maximum of the total dose of the micelle was accumulated per g of the brain (FIG. 3A). In this respect, the micelle concentration in blood was decreased at the same time with refeeding (data not shown). Such increase in the amount of the micelle accumulated in the brain was not observed in micelles unmodified at the outer surface thereof with glucose. Thus, these results demonstrated that for the accumulation of the Glc(6)-PIC micelle in the brain, it is important to decrease the blood glucose level of a mouse by fasting and to raise the blood glucose level of the mouse before or after micelle administration. However, in the fasted mice, some micelles were taken up into the brain after micelle administration and even before refeeding (filled square in FIG. 3A). Also, in the non-fasted mice, some micelles also taken up into the brain after micelle administration (open square in FIG. 3A). As a result of evaluating the amount of the micelle accumulated in each organ, the amount of the micelle accumulated in the brain was selectively increased by blood glucose control (FIG. 3B). Thus, it can be understood that increase in the amount of the micelle accumulated by blood glucose control is specific for the brain. The liver and the kidney exhibited approximately 8% and 4% accumulations, respectively, regardless of the presence or absence of blood glucose control (data not shown). If Glc(6)-PEG-P(Asp.) is used as all anionic polymers for preparing the micelle modified at the outer surface thereof with glucose via carbon at position 6 thereof (Glc(6)-PIC micelle), a micelle having 50% rate of glucose introduction can be obtained. If Glc(6)-PEG-P (Asp.) is used as half of these anionic polymers, a micelle having 25% rate of glucose introduction can be obtained. As a result of administering each obtained micelle by the method described above, the micelle having 25% rate of glucose introduction exhibited more than 3% accumulation in the brain, whereas the micelle having 50% rate of glucose introduction exhibited approximately 1.3% accumulation in the brain.

Figure 4:
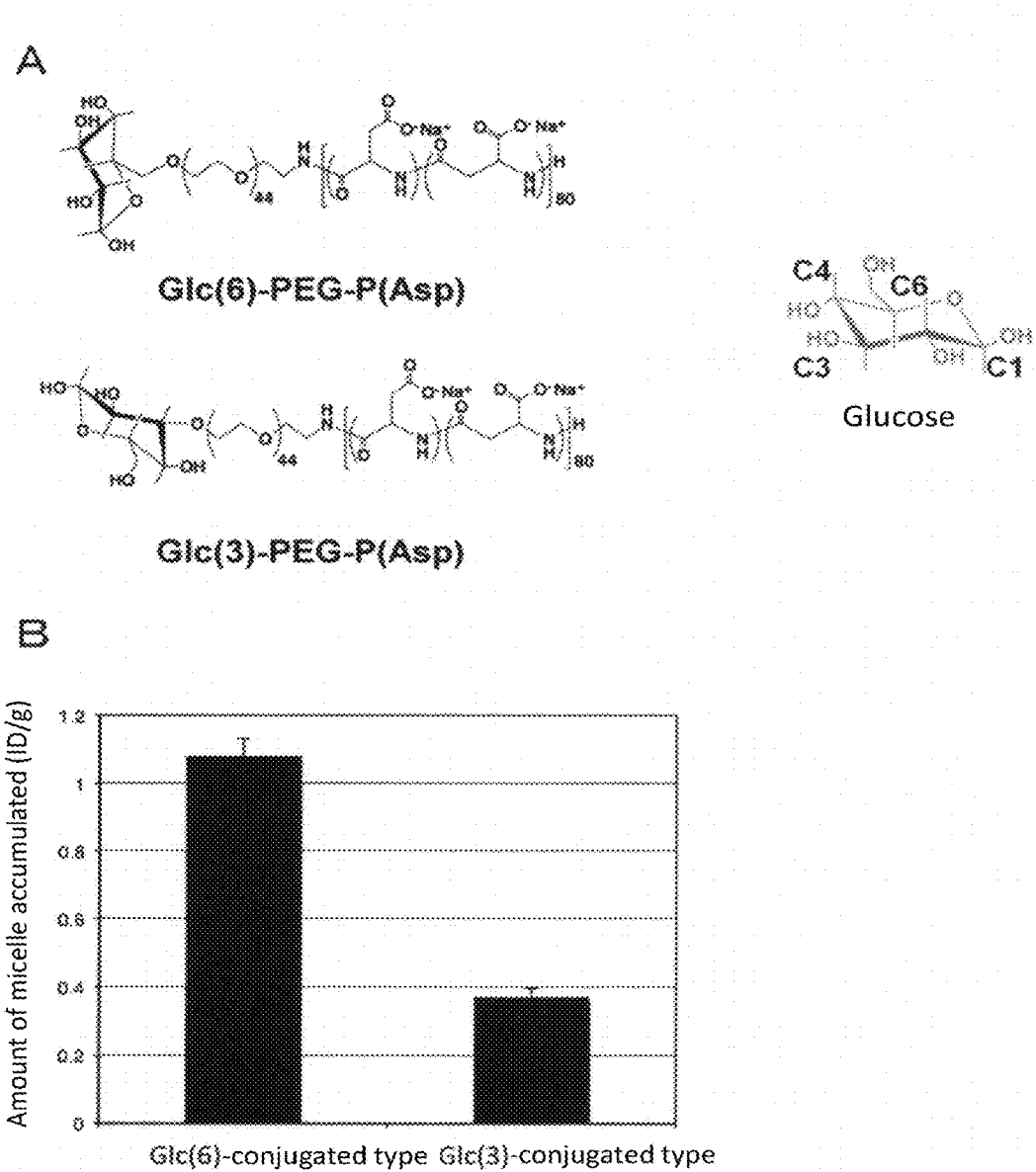
FIG. 4 is a diagram showing the accumulation of a micelle obtained by the conjugation of glucose via carbon at position 3 or 6 thereof with a polymer in the brain.

The micelles each modified at the outer surface with glucose via carbon at position 3 thereof (Glc(3)-PIC micelle and Glc(6)-PIC micelle) were compared in terms of the amount of each micelle accumulated in the brain. Specifically, the Glc(6)-Cy5-PIC micelle and the Glc(3)-Cy5-PIC micelle were each i.v. administered to fasted mice by the method described above. 6 hours later, the mice were refed, and the brain was harvested 8 hours after the administration (2 hours after the refeeding). The amount of each sample accumulated in the brain was calculated by the method described above. As a result, a larger number of the Glc(6)-PIC micelle than the Glc(3)-PIC micelle was found to be accumulated in the brain (FIG. 4B).

Figure 5:
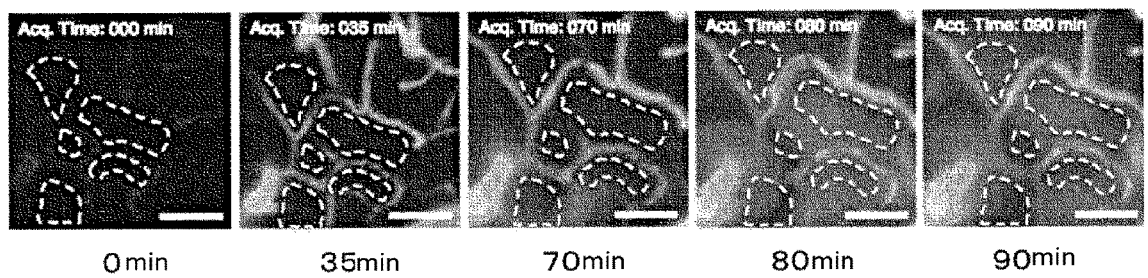
FIG. 5 is a diagram showing a fluorescent microscope image of the brain parenchyma when a micelle was taken up into the brain (FIG. 5A), and changes in blood glucose level and the amount of uptake into the brain (FIG. 5B).
Figure 5:
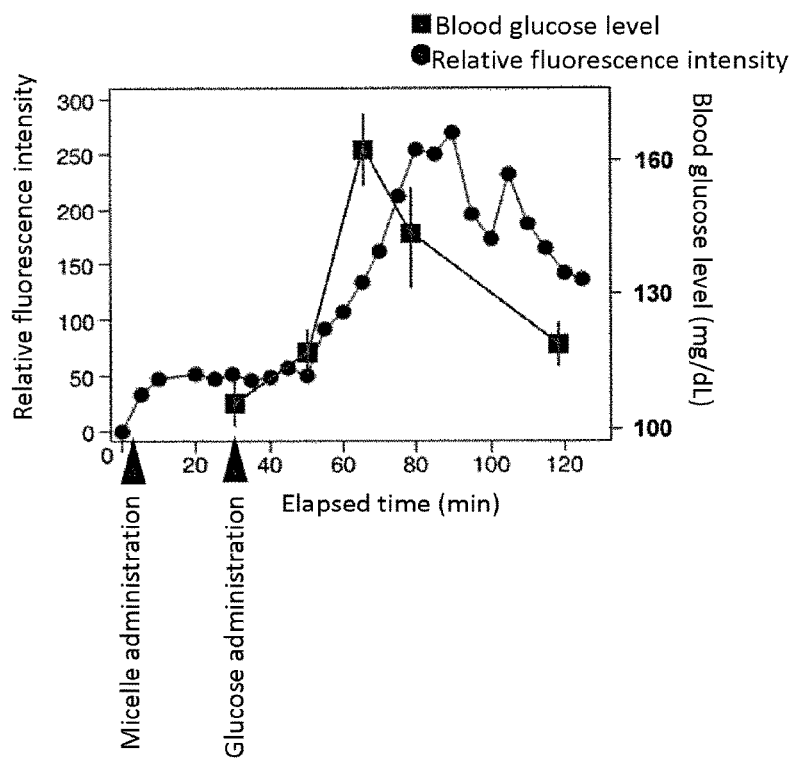

In order to further examine the detailed accumulation site of a micelle in the brain, in vivo observation under a confocal microscope was carried out. Specifically, first, 24-hour fasted mice (Balb/c, female, 6 weeks old) were subjected to craniotomy under 2.5% isoflurane anesthesia. Next, the anesthesia was maintained, while a catheter for the i.v. administration of the sample was placed into the microvein. Also, a catheter for the intraperitoneal administration (i.p.) of a glucose solution was placed into the peritoneal cavity, and each mouse was placed on the stage of a confocal microscope (Nikon AIR). After 5 minutes into the observation, the Glc(6)-Cy5-PIC micelle (1 mg/mL, 200 µL) was i.v. administered through the catheter (0 min in the graph of FIG. 5B is the timing of sample administration). Subsequently, a 20 v/v % glucose solution was i.p. administered through the catheter 30 minutes after the sample administration. The fluorescence was detected over approximately 3 hours using laser having an excitation wavelength of 638 nm to observe the behavior of the sample in the brain in real time (fluorescence wavelength: 662 to 737 nm). As a result, the fluorescence observed only in the vascular vessel was observed to ooze into the brain parenchyma (e.g., dotted-line areas) as the time passed (FIG. 5A). On the basis of the moving images obtained in this observation, the elapsed time in the observation was plotted on the abscissa, and average fluorescence intensity at ROI (region of interest) in five regions (dotted-line areas of the brain parenchyma shown in FIG. 5A) that did not overlap with the cerebrovascular vessels was plotted on the ordinate. As a result, the uptake of the micelle into the brain parenchyma was elevated following a rise in blood glucose level (FIG. 5B). The blood glucose levels of the mice were determined by collecting 5 µL of blood from the microvein of each mouse immediately before the i.p. administration of the glucose solution and 20 minutes, 30 minutes, 50 minutes, and 90 minutes after the administration and determining the blood glucose level using a blood glucose level measurement apparatus for laboratory animals (FIG. 5B). The uptake of the micelle into the brain occurred along with decrease in blood glucose level following a rise in blood glucose level, suggesting that the micelle may be administered after a rise in blood glucose level.

Figure 11:
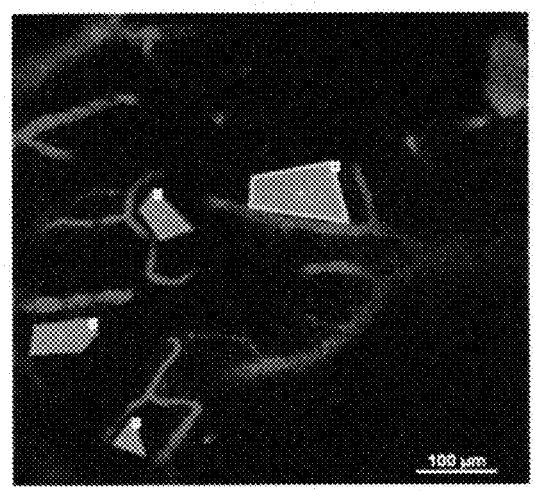
FIG. 11 is a diagram showing changes in fluorescence intensity in the brain parenchyma in the case of intravenously (i.v.) administering the Glc(6)-Cy5-PIC micelle 30 minutes after intraperitoneal (i.p.) administration of glucose.
Figure 11:
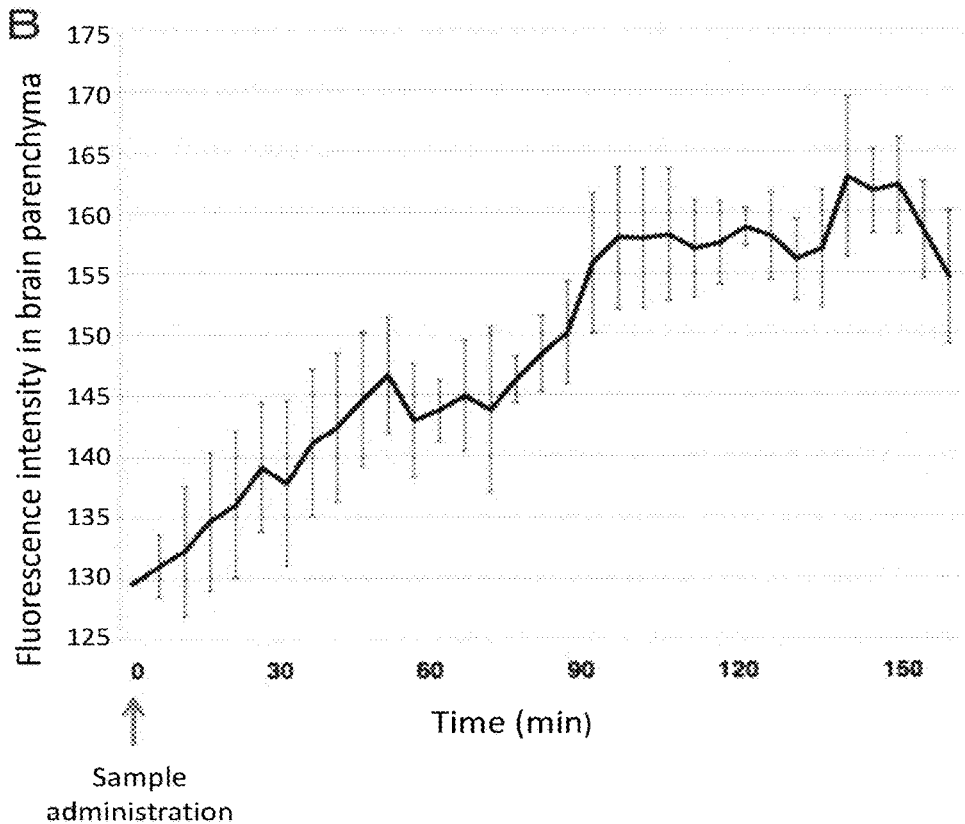

Next, it was confirmed that even if the micelle was administered after a rise in blood glucose level, the micelle could enter the brain parenchyma. Specifically, first, 24-hour fasted mice (Balb/c, female, 6 weeks old) were subjected to craniotomy under 2.5% isoflurane anesthesia. Next, the anesthesia was maintained, while a catheter for the intraperitoneal administration (i.p.) of a glucose solution was placed into the peritoneal cavity, and each mouse was placed on the stage of a confocal microscope (Nikon A1R). A 20 v/v % glucose solution was i.p. administered through the catheter. Subsequently, the Glc(6)-Cy5-PIC micelle (1 mg/mL, 200 µL) was i.v. administered through a catheter or i.p administered without the use of a catheter 30 minutes after the glucose administration to start observation (0 min in the graph of FIG. 11B represents the timing of sample administration). The fluorescence was detected over approximately 3 hours using laser having an excitation wavelength of 638 nm to observe in real time the accumulation of the sample in the four regions of the brain parenchyma shown in FIG. 11A with fluorescence intensity as an index (fluorescence wavelength: 662 to 737 nm). As a result, as shown in FIG. 11B, the uptake of the sample into the brain parenchyma was observed from immediately after the i.v. administration of the sample. The amount of this uptake was gradually increased as the time passed. The uptake was sustained over 3 hours. The time-dependent pattern of the amount of the sample taken up into the brain parenchyma was changed by changing the order in which glucose and the sample were administered. This means that the crossing timing at the blood-brain barrier can be controlled by changing the order in which glucose and the sample are administered.

This demonstrated that the composition of the present invention is capable of crossing the blood-brain barrier and effectively arriving at the brain parenchyma by blood glucose control.

Example 3: Preparation and Pharmacokinetic Evaluation Experiment of PICsome

PICsome was prepared as a hollow carrier having a diameter of approximately 100 nm and studied for the targeting effect thereof on the brain by pharmacokinetic evaluation.

3-1. Synthesis of Homo-P(Asp.-AP)

First, poly(β-benzyl-L-aspartate) (homo-PBLA polymer) was obtained by the polymerization of BLA-NCA. Specifically, 20 g of β-benzyl-L-aspartate-N-carboxylic anhydride (BLA-NCA) is dissolved in 33.3 mL of N,N'-dimethylformamide (DMF) and 300 mL of dichloromethane. 89.0 µL of N-butylamine is added to the BLA-NCA solution. The mixed solution was kept at 35° C., while polymerization was carried out for 40 hours. After the completion of the polymerization reaction was confirmed by IR analysis, the reaction mixture was added dropwise to 1 L of hexane/ethyl acetate solution (hexane:ethyl acetate=6:4), and the precipitated polymer was recovered by suction filtration, washed with diethyl ether, and then dried in vacuum to obtain 14.82 g of homo-PBLA polymer (79%).

Next, poly((5-aminopentyl)-aspartic acid) (homo-P(Asp.-AP)) was synthesized from the obtained homo-PBLA polymer. Specifically, 1 g of the benzene-freeze-dried homo-PBLA is dissolved in 10 mL of N-methyl-2-pyrrolidone (NMP). 17.2 mL of DAP was dissolved in 17.2 mL of NMP, and the solution is added to the homo-PBLA solution. The mixed solution was kept at 5° C., while reaction was carried out for 40 minutes. Then, 10 mL of an aqueous solution containing 20% by weight of acetic acid was added to the reaction solution, and the mixture was dialyzed in water using a dialysis membrane (molecular weight cutoff: 6,000-8,000). The intramembrane solution was freeze-dried to obtain 0.76 g of P(Asp.-AP) (82%).

3-2. Preparation of Glc(6)-Cy5-PICsome 20 mg of the Glc(6)-PEG-P(Asp.) and 40 mg of the Cy5-PEG-P(Asp.) obtained in Example 1 were dissolved in 60 mL of a 10 mM phosphate buffer solution (PB, pH 7.4, 0 mM NaCl) to prepare a 1 mg/mL mixed solution of Glc(6)-PEG-P(Asp.) and Cy5-PEG-P(Asp.). 50 mg of homo-P(Asp.-AP) was similarly dissolved in 50 mL of PB to prepare a 1 mg/mL homo-P(Asp.-AP) solution. Next, these two types of aqueous solutions, i.e., the mixed solution of Glc(6)-PEG-P(Asp.) and Cy5-PEG-P(Asp.) and the homo-P(Asp.-AP) solution, were mixed at 4.0 mL and 5.0 mL, respectively, in a 50 mL conical tube and stirred for 2 minutes by vortex (2000 rpm). Then, 5.6 mL of a PB solution containing a water-soluble condensing agent EDC (10 mg/mL) was added thereto, and the tube was left standing overnight to cross-link the core of a polyion complex. Then, polymers that were not involved in PICsome formation, and EDC by-products, etc. were removed using an ultrafiltration tube equipped with a membrane having a molecular weight cutoff of 100,000. The size (Z-average particle size) and polydispersity index (PDI) of the obtained Glc(6)-Cy5-PICsome were measured using Zetasizer (Malvern Instruments Ltd.). The shape of the micelle was observed using a transmission electron microscope (TEM, JEM-1400) after staining with uranyl acetate. The results demonstrated that PICsome having a diameter of 100 nm (PDI=0.086) was obtained (data not shown).

3-3. Pharmacokinetic Evaluation

Figure 6:
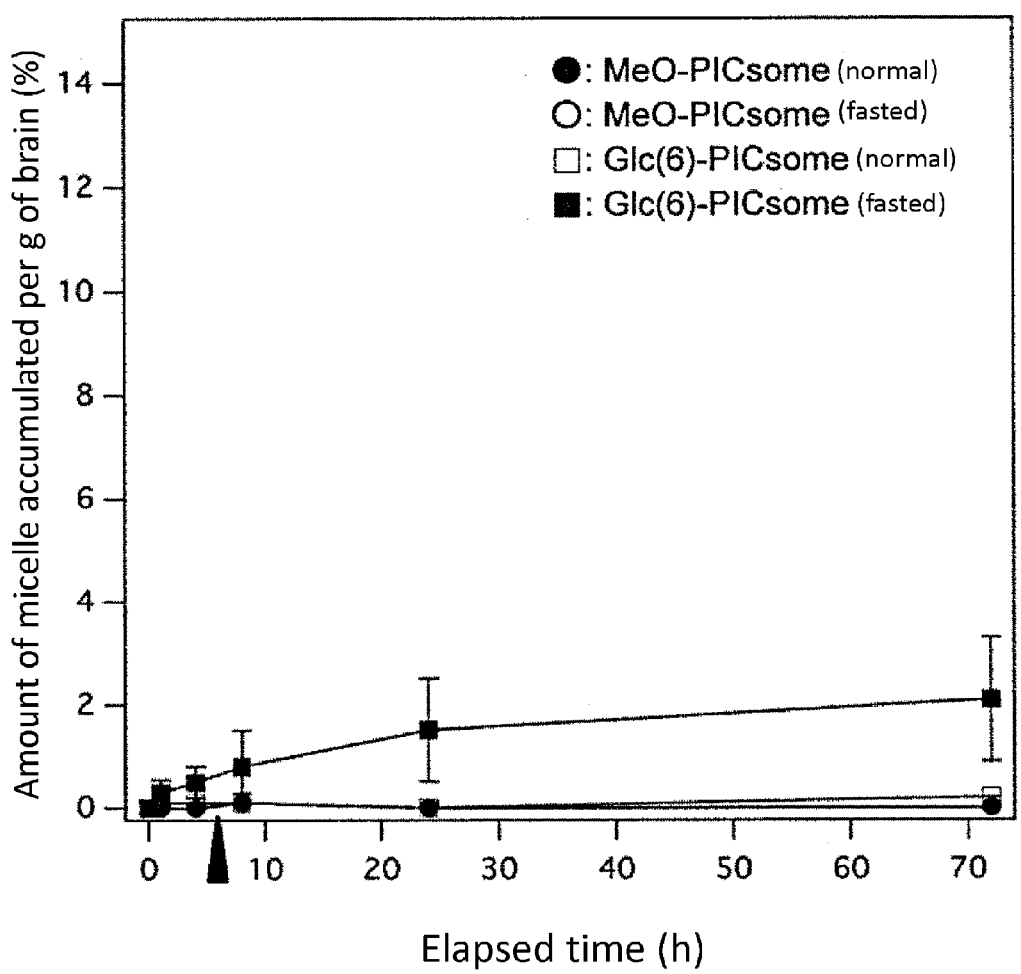
FIG. 6 is a diagram showing the accumulation of PICsome having a diameter of 100 nm in the brain.

Each PICsome was administered to mice and the accumulation of the PICsome in the brain was observed in totally the same way as in Example 2 except that the obtained PICsome was administered instead of the PIC micelle. As a result, only PICsome modified at the outer surface thereof with glucose was observed to accumulate rapidly in the brain after feeding (FIG. 6). The PICsome modified at the outer surface thereof with glucose was accumulated in an amount of approximately 2% per g of the brain (FIG. 6).

This demonstrated that the vesicle even having a diameter of 100 nm is capable of crossing the blood-brain barrier without problems.

Figure 13:
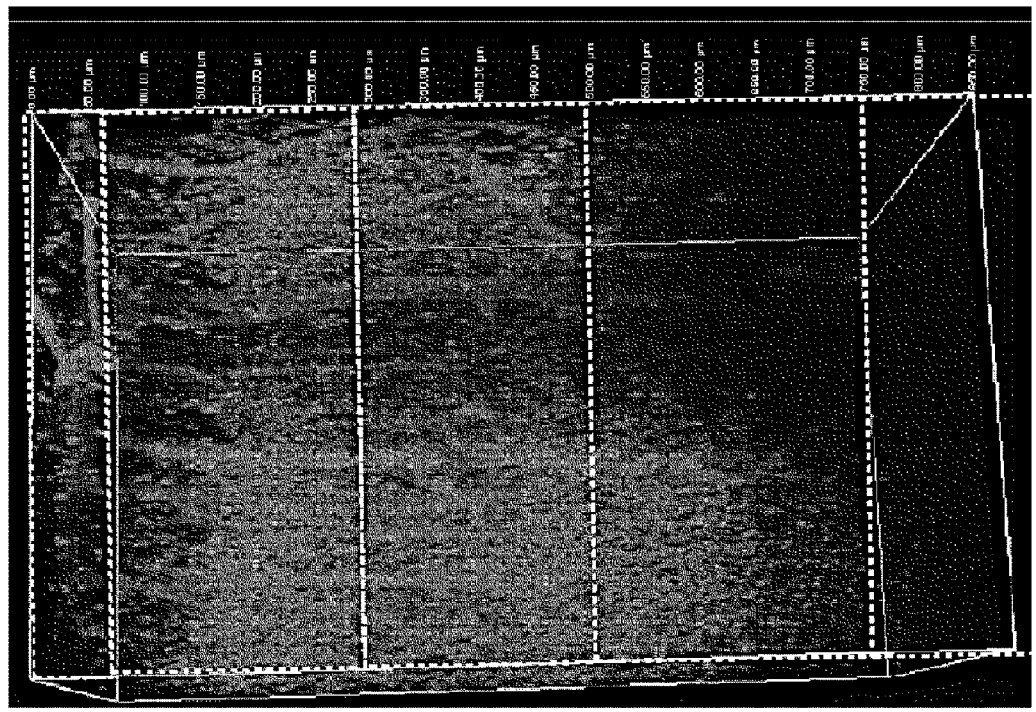
FIG. 13 is a diagram showing the localization of a PIC micelle after intravenous administration in the mouse cerebral cortex.
Figure 13:
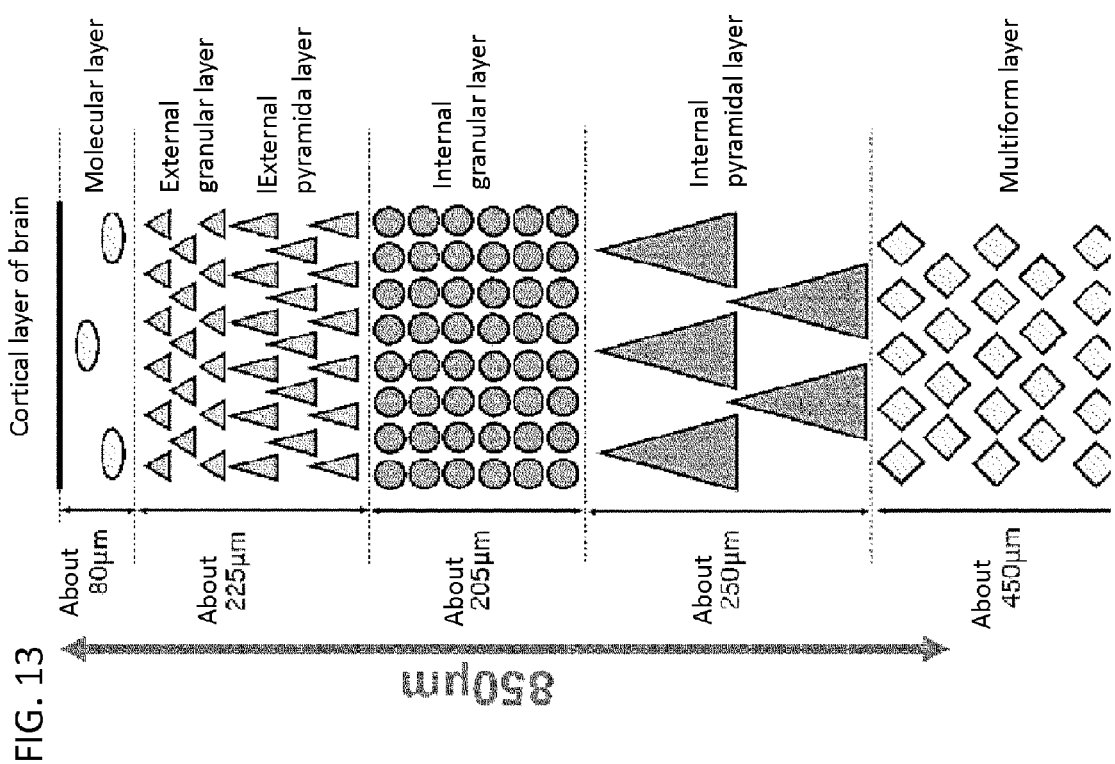

The localization of the vesicle in a deep region of the brain (cerebral cortex) was further observed using a two-photon microscope (multiphoton excitation laser Nikon A1RMP-IS-S33 for high-speed confocal laser microscopes). The obtained results are as shown in FIG. 13. In short, stronger fluorescence derived from the PIC micelle was observed in the deep region of the brain compared with the cortical layer of the brain.

Figure 14:
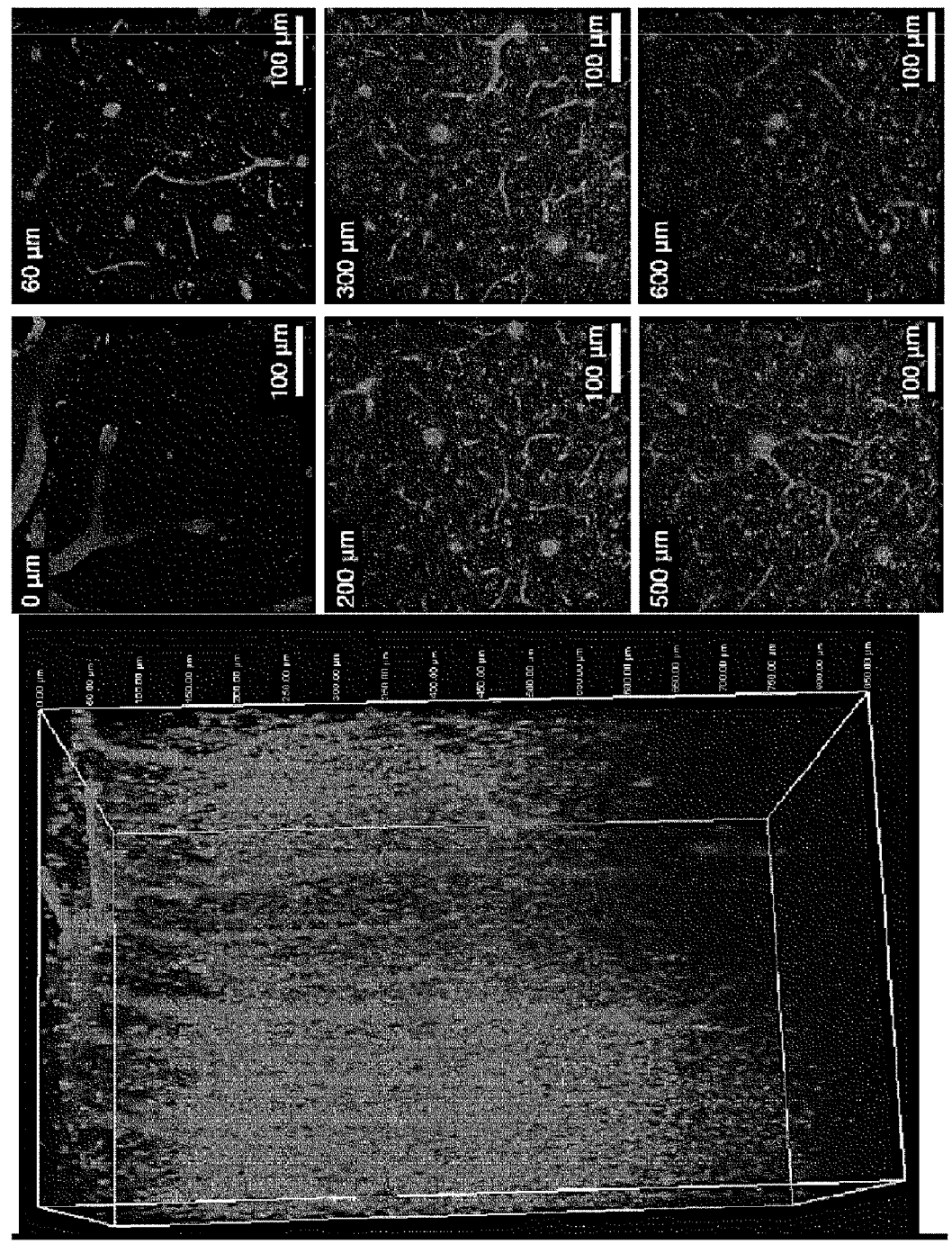
FIG. 14 is a diagram showing the localization of a PIC micelle after intravenous administration in a section of the mouse cerebral cortex.

Fluorescent images of sections positioned 0 μm, 60 μm, 200 μm, 300 μm, 500 μm, or 600 μm from the cortical layer of the brain were observed. As a result, the PIC micelle was confirmed to enter the brain parenchyma at any of the depths. A large amount of fluorescence was localized in the brain parenchyma particularly at 200 μm to 500 μm (FIG. 14).

Figure 15:
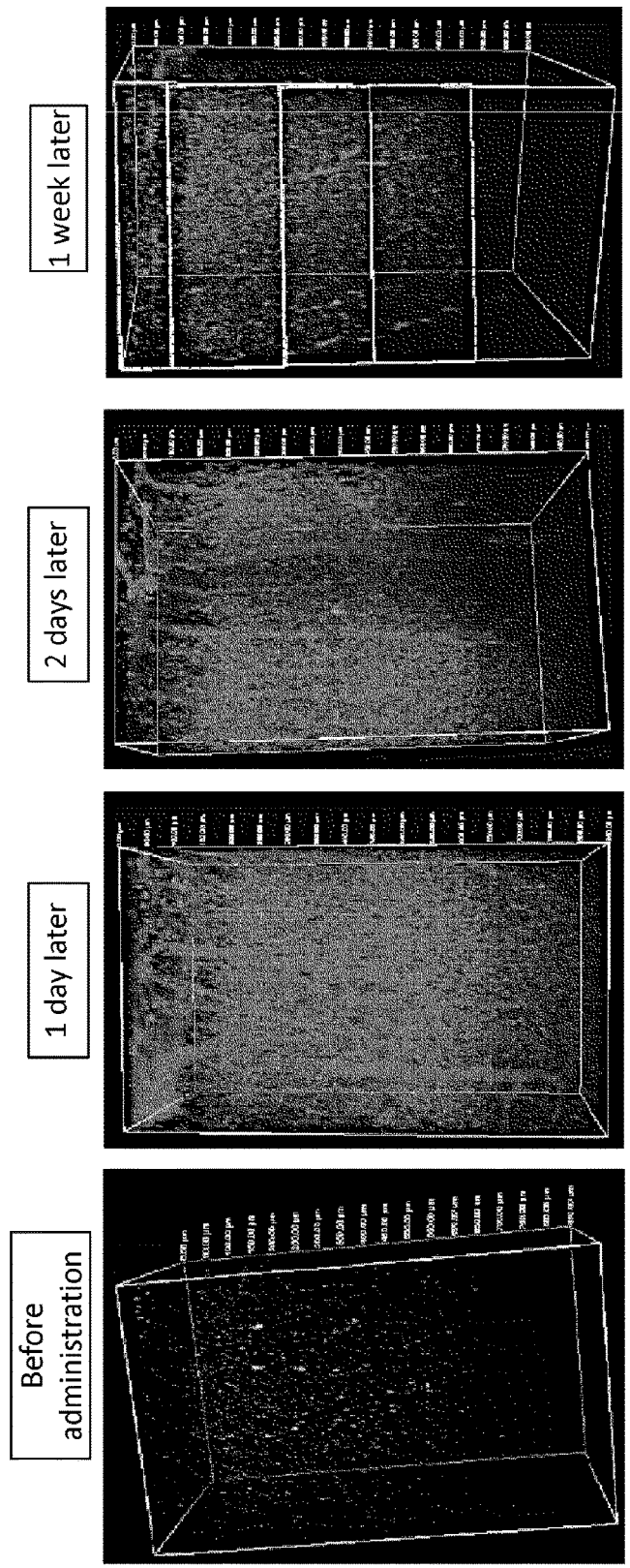
FIG. 15 is a diagram showing time-dependent changes in the localization of a PIC micelle after intravenous administration in the mouse cerebral cortex.

Time-dependent changes in fluorescence intensity in the cerebral cortex were further confirmed. As shown in FIG. 15, a large amount of fluorescence was localized in the brain parenchyma 1 day later to 1 week later.

These results demonstrated that the PIC micelle modified at the surface thereof with glucose, when administered to a subject in conjunction with the blood glucose control of the present invention, can be accumulated in the brain parenchyma even in a deep region (e.g., 60 μm to 600 μm) of the brain. This accumulation was sustained even 1 week after the administration. The brain contains a molecular layer, an external granular layer, an external pyramidal layer, an internal granular layer, an internal pyramidal layer, and a multiform layer in this order from the cortical layer (see e.g., FIGS. 13 to 15). The carrier was successfully delivered to the brain parenchyma in any of these layers. The delivery of the carrier was significantly effective, particularly, for the external pyramidal layer and the internal granular layer among these layers.

Example 4: Preparation and Pharmacokinetic Evaluation of siRNA Micelle

In this Example, pharmacokinetic evaluation was conducted in the same way as in Examples 2 and 3 using siRNA having a short blood retention time and low delivery efficiency. More specifically, in this Example, a micelle consisting of PEG-polycation conjugated with glucose and fluorescently labeled siRNA was used to evaluate the accumulation of the siRNA in the brain.

4-1. Synthesis of Glc(6)-PEG-P(Asp.-TEP)-Chol

First, BIG-PEG-PBLA-Chol was synthesized from the BIG-PEG-PBLA obtained by the method described in Example 1. Specifically, 120 mg of the BIG-PEG-PBLA was dissolved in 10 mL of NMP. 10 equivalents of 4-cholesterylamino-4-butanoic acid with respect to the terminal amino group of PBLA, and a catalytic amount of dimethylaminopyridine were added to the solution, and the mixture was then stirred at room temperature for 6 hours. The reaction solution was added dropwise to a diethyl ether/2-propanol (9:1) solution to precipitate the matter of interest. The precipitate was filtered and then dried under reduced pressure to obtain 130 mg of BIG-PEG-PBLA-Chol (yield: 95%).

Next, BIG-PEG-P(Asp-TEP)-Chol was synthesized from the obtained (BIG)-PEG-PBLA-Choi. Specifically, 100 mg of the BIG-PEG-PBLA-Chol was dissolved in 5 mL of NMP. The polymer solution was added dropwise to a tetraethylenepentamine (TEP) solution diluted with NMP, and the mixture was then reacted at 20° C. for 1 hour. The reaction solution was added dropwise to ice-cold 1 N hydrochloric acid, and the mixture was dialyzed at 4° C. using a dialysis membrane having a molecular weight cutoff of 12,000 to 14,000. The external dialysis solution used was 0.01 N hydrochloric acid. Then, the reaction solution was dialyzed against pure water used as an external dialysis solution, and the obtained solution was then freeze-dried to recover 56 mg of BIG-PEG-P(Asp-TEP)-Chol (yield: 73%).

Finally, Glc(6)-PEG-P(Asp-TEP)-Chol was obtained from the BIG-PEG-P(Asp-TEP)-Chol. Specifically, 56 mg of the BIG-PEG-P(Asp-TEP)-Chol was dissolved in 8 mL of a trifluoroacetic acid/pure water (8:2) solution, and the solution was reacted for 1 hour. The reaction solution was dialyzed against 0.01 N NaOH used as an external dialysis solution using a dialysis membrane (molecular weight cut-off: 1,000), and subsequently dialyzed against pure water. The obtained solution was freeze-dried to obtain 67 mg of Glc(6)-PEG-P(Asp.-TEP)-Chol (yield: 82%).

4-2. Preparation of Glc(6)-siRNA Micelle

Figure 7:
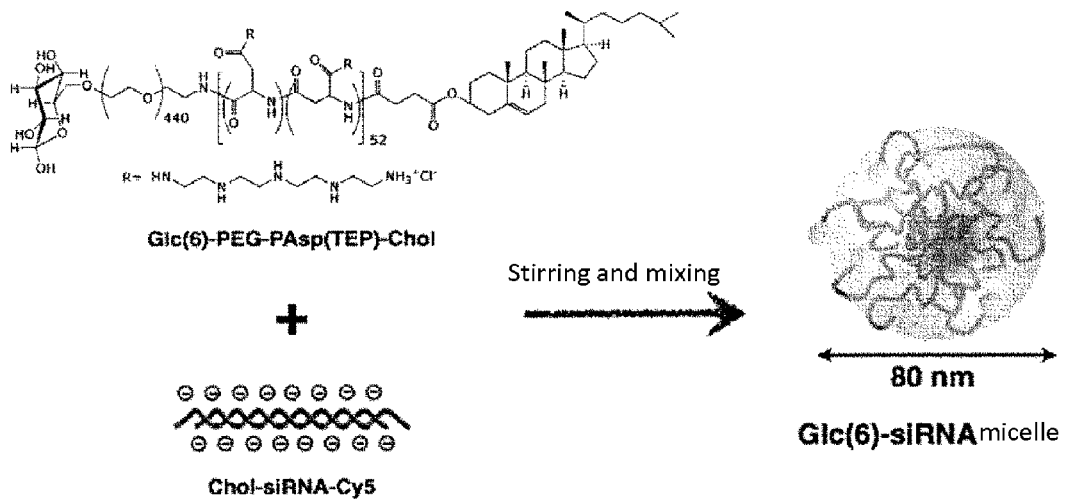
FIG. 7 shows the accumulation of an siRNA micelle modified at the outer surface thereof with glucose in the brain.
Figure 7:
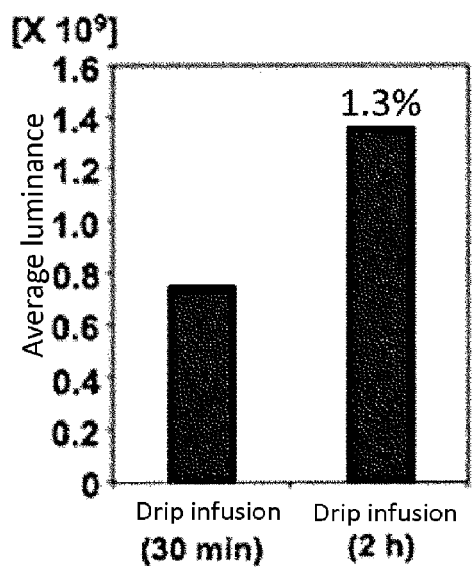

A Glc(6)-siRNA micelle was prepared according to the scheme of FIG. 7A. Specifically, 262.5 µL of Glc(6)-PEG-P(Asp.-TEP)-Chol (2 mg/mL) dissolved in a 10 mM HEPES buffer solution was diluted with 437.5 µL of a HEPES buffer solution. 279 µL of Cy5-siRNA-chol (75 µM) (scramble siRNA manufactured by Hokkaido System Science Co., Ltd.) was diluted with 1121 µL of a HEPES buffer solution. These two solutions thus obtained were mixed and pipetted 10 times to obtain a Glc(6)-siRNA micelle. Immediately before the in vivo experiment, 65 µL of a 5 M NaCl solution was added to 2.1 mL of the micelle solution, and the mixture became an isotonic solution by pipetting and was then used in administration. The size (Z-average particle size) and polydispersity index (PDI) of the obtained Glc(6)-Cy5-siRNA micelle were measured using Zetasizer (Malvern Instruments Ltd.). The shape of the micelle was observed using a transmission electron microscope (TEM, JEM-1400) after staining with uranyl acetate. The results demonstrated that an siRNA micelle having a diameter of 80 nm (PDI=0.104) was obtained.

4-3. Pharmacokinetic Evaluation

Figure 8:
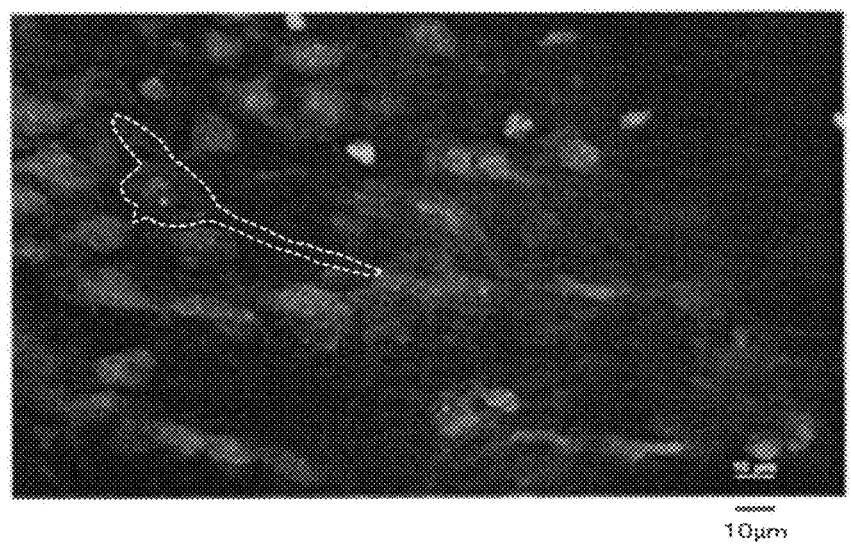
FIG. 8 is a fluorescent microscope image showing the accumulation of the siRNA micelle in brain cells.

The obtained Glc(6)-Cy5-siRNA micelle was subjected to precise continuous intravenous administration at a rate of 200 µL/2 hours over 30 minutes or 2 hours using a syringe pump (Harvard Apparatus), and a 20% glucose solution was intraperitoneally administered after 5 minutes into the administration. 1 hour after the completion of the siRNA micelle administration, the brain was harvested and homogenized using a Multi-Beads Shocker. Then, each luminance was evaluated using IVIS Imaging System (Xenogen). As a result, as the intravenous administration time was longer, the luminance of the brain was elevated. The accumulation in the brain based on the 2-hour intravenous administration was larger than that based on the 30-minute intravenous administration (FIG. 7B). As a result of calculating the amount of the micelle accumulated in the brain, the 2-hour intravenous administration was found to be able to deliver 1.3% of the amount of the siRNA micelle administered to the brain (per g). 6 hours after the completion of the administration, the brain was further harvested and observed under a confocal microscope (LSM510) to measure fluorescence intensity in the brain parenchyma. The results demonstrated that the siRNA micelle was accumulated in brain cells (FIG. 8).

The results of Example 4 demonstrated even a substance such as siRNA having a short blood retention time and low delivery efficiency can be delivered very effectively to the brain by the method of the present invention. According to the blood glucose control of the present invention, the siRNA micelle may be delivered to the brain parenchyma even by rapid intravenous administration. In this Example, the continuous intravenous administration was found to be able to drastically improve the amount of the siRNA micelle delivered to the brain parenchyma.

Example 5: Pharmacokinetic Evaluation of Block Copolymer Modified with Glucose

In this Example, Glc(6)-PEG-polyaspartic acid was administered to mice without forming a micelle, and evaluated for the pharmacokinetics thereof.

The Glc(6)-PEG-polyaspartic acid used was the Glc(6)-PEG-polyaspartic acid synthesized in Example 1. PEG-polyaspartic acid was used as a control.

The Glc(6)-PEG-polyaspartic acid and the control each having a concentration of 3 mg/mL were each intravenously administered at a dose of 200 µL to each of Balb/c mice (female, 6 weeks old, n=3). The administration was carried out at a constant rate over 2 hours. After 5 minutes into the administration, a 20% glucose solution was intraperitoneally administered thereto. 1 hour after the completion of the administration of the Glc(6)-PEG-polyaspartic acid and the control, the block copolymer modified with glucose was analyzed for the pharmacokinetics thereof.

Figure 9:
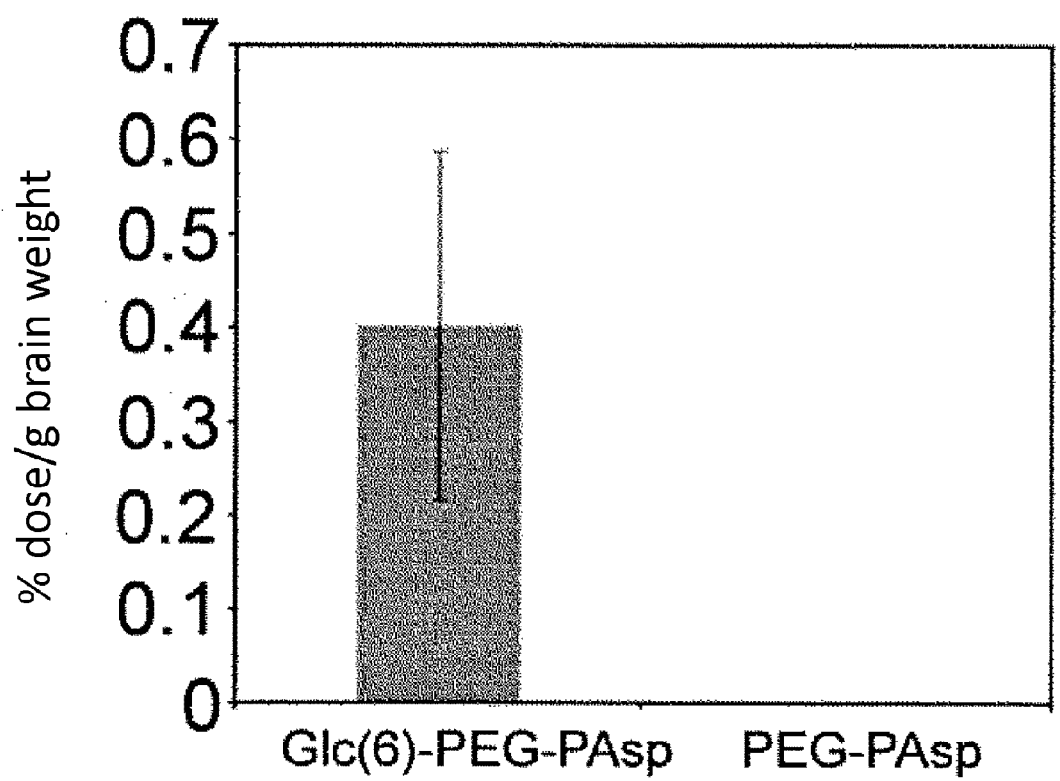
FIG. 9 is a diagram showing the accumulation of a polymer conjugated with one molecule of glucose in the brain.

The results are as shown in FIG. 9. As shown in FIG. 9, the PEG-polyaspartic acid unconjugated with glucose exhibited no accumulation in the brain, whereas the Glc(6)-PEG-polyaspartic acid containing the conjugated glucose exhibited accumulation in the brain at 0.4% of the total dose per g of the brain. Thus, the modification of the polymer with one molecule of glucose sufficed for the delivery thereof to the brain. Even donepezil hydrochloride, which reportedly breaks through the blood-brain barrier particularly easily, is accumulated only at 0.13% of the total dose per g of the brain (Drug Metabolism and Disposition, 1999, 27 (12): 1406-1414).

Example 6: Preparation and Pharmacokinetic Evaluation of Glucose-Conjugated Antibody In this Example, an antibody was conjugated with glucose and evaluated for the pharmacokinetics thereof. As a result, the antibody also exhibited accumulation in the brain by blood glucose control.

The antibody used was commercially available Mouse IgG, Isotype Control (Southern Biotechnology Associates Inc.). The conjugate of the antibody and glucose was prepared as follows.

6-1. Synthesis of Glucose-Introduced Polyethylene Glycol-Polyaspartic Acid Block Copolymer Fluorescently Labeled with DyLight 488

First, THP-PEG-OH was synthesized. Specifically, 0.104 mL of 2-(2-hydroxyethoxy)tetrahydropyran (THP) was dissolved in 100 mL of tetrahydrofuran (THF). 2.8 mL of a THF solution containing 0.3 M potassium naphthalene was added dropwise to the THP solution, then 8.9 mL of ethylene oxide (EO) was added thereto in an argon atmosphere, and the mixture was reacted at 40° C. for 1 day. Then, the reaction solution was reprecipitated with diethyl ether to obtain 8.56 g of polyethylene glycol having a tetrahydropyranyl group at one end and a 3-hydroxypropyl group at the other end (THP-PEG-OH) (molecular weight: 12,000) (yield: 95%).

Next, the OH group of the obtained THP-PEG-OH was mesylated. Specifically, 19.7 µL of methanesulfonyl chloride (MsCl) was dissolved in 20 mL of THF. Also, 1.4 g of the THP-PEG-OH (molecular weight: 12,000) was dissolved in 10 mL of tetrahydrofuran (THF), and 89 µL of triethylamine was added to the solution. The THP-PEG-OH solution was added dropwise to the MsCl solution cooled in a water bath, and the mixture was stirred for 3 hours and 30 minutes. The reaction mixture was added dropwise to 200 mL of diethyl ether, and the precipitated polymer was recovered by suction filtration, washed with diethyl ether, and then dried in vacuum to obtain 1.50 g of polyethylene glycol having a 3-methanesulfonyl group at one end and a tetrahydropyranyl group at the other end (MsO-PEG-THP) (yield: 100%).

Next, N$_3$-PEG-THP was synthesized from the obtained MsO-PEG-THP. Specifically, 15 g of the MsO-PEG-THP (molecular weight: 12,000) was dissolved in 100 mL of N,N'-dimethylformamide (DMF). 1.63 g of sodium azide was added to the reaction solution with stirring at room temperature. The mixed solution was kept at 45° C., while stirring was carried out for 71 hours. The mixed solution was brought back to room temperature, followed by the addition of 200 mL of pure water. The mixed solution was subjected to extraction with 200 mL of methylene chloride six times using a separatory funnel, and the obtained organic layer was concentrated to 150 mL using a rotary evaporator. The concentrate was added dropwise to 2 L of ethanol, and the precipitated polymer was recovered by suction filtration and then dried in vacuum to obtain 14.3 g of polyethylene glycol having an azide group at one end and a tetrahydropyranyl group at the other end (N$_3$-PEG-THP) (yield: 95%).

Next, the N$_3$-PEG-THP was deprotected to obtain N$_3$-PEG-OH. Specifically, 14.1 g of the N$_3$-PEG-THP (molecular weight; 12,000) was dissolved in 200 mL of methanol. 24 mL of an aqueous solution containing 1 N HCl was added into the mixed solution at room temperature. The reaction temperature was kept at 25° C., while the reaction solution was stirred for 4 hours. The reaction mixture was added dropwise to 2.5 L of diethyl ether, and the precipitated polymer was recovered by suction filtration, washed with diethyl ether, and then dried in vacuum to obtain 13.7 g of polyethylene glycol having an azide group at one end and a 3-hydroxypropyl group at the other end (N$_3$-PEG-OH) (yield: 96%).

Next, the N$_3$-PEG-OH was aminated to obtain N$_3$-PEG-NH$_2$. Specifically, 1.02 g of the N$_3$-PEG-OH (molecular weight: 12,000) was dissolved in 30 mL of tetrahydrofuran (THF), and 47.4 µL of triethylamine was added to the solution. 19.7 µL of methanesulfonyl chloride was dissolved in 20 mL of THF. The N$_3$-PEG-OH solution was cooled in a water bath of room temperature, while the solution was added to the N$_3$-PEG-OH solution. The mixed solution was stirred at room temperature for 6 hours. The precipitated salt was removed by filtration. The reaction mixture was added dropwise to a mixed solution containing 950 mL of diethyl ether and 50 mL of 2-propanol, and the precipitated polymer was recovered by suction filtration, washed with diethyl ether, and then dried in vacuum. The obtained powder was dissolved in 8 mL of a 28% aqueous ammonia solution, and the solution was reacted at room temperature for 3 days. The reaction solution was dialyzed against pure water using a dialysis membrane (molecular weight cutoff: 6000-8000). Then, a fraction in which the amination did not proceed was removed using Sephadex C-25 (GE Healthcare Japan Corp.), and the residue was freeze-dried to recover 620 mg of polyethylene glycol having an azide group at one end and a 3-aminopropyl group at the other end (N$_3$-PEG-NH$_2$) (yield: 61%).

Next, N$_3$-PEG-PBLA was synthesized from the N$_3$-PEG-NH$_2$. Specifically, 150 mg of the benzene-freeze-dried N$_3$-PEG-NH$_2$ (molecular weight: 12,000) was dissolved in 5.4 mL of dichloromethane. 218 mg of β-benzyl-L-aspartate-N-carboxylic anhydride was dissolved in 0.6 mL of DMF, and the solution was added to the N$_3$-PEG-NH$_2$ solution, followed by polymerization at 35° C. for 2 days in the presence of argon. After the completion of the polymerization reaction was confirmed by IR analysis, the reaction mixture was added dropwise to 150 mL of diethyl ether, and the precipitated polymer was recovered by suction filtration and dried in vacuum to obtain 250 mg of a block copolymer of polyethylene glycol having an azide group at one end and poly(β-benzyl-L-aspartate) (N$_3$-PEG-PBLA) (molecular weight: 12,000) (yield: 91%).

Next, N$_3$-PEG-P(Asp) was obtained from the N$_3$-PEG-PBLA. Specifically, 250 mg of the N$_3$-PEG-PBLA was dissolved in 4 mL of acetonitrile. 5.5 mL of an aqueous solution containing 0.5 N sodium hydroxide was added to the solution, and the mixture was stirred at room temperature for 1 hour. The reaction solution was dialyzed in water using a dialysis membrane (molecular weight cutoff: 6000-8000). The intramembrane solution was freeze-dried to obtain 189 mg of a block copolymer of polyethylene glycol having an azide group at one end and polyaspartic acid (N$_3$-PEG-P(Asp)) (molecular weight: 12,000) (yield: 89%).

Next, 6-amino-6-deoxy-1,2:3,5-di-O-isopropylidene-α-D-glucofuranose (P-aminoglucose) was synthesized. The P-aminoglucose was synthesized on the basis of the description of Carbohydr. Res. 19, 197-210 (1971).

A protected glucose-introduced polyethylene glycol-polyaspartic acid block copolymer was synthesized. Specifically, 137 mg of the 6-amino-6-deoxy-1,2:3,5-di-O-isopropylidene-α-D-glucofuranose (P-aminoglucose) was dissolved in 4 mL of N,N'-dimethylformamide (DMF). 40 mg of the block copolymer of polyethylene glycol having an azide group at one end and polyaspartic acid (N$_3$-PEG-P(Asp)) (molecular weight: 12,000) was dissolved in a mixed solvent containing 4 mL of DMF and 1 mL of water, and the solution was added to the P-aminoglucose solution. Then, 203 mg of 1-ethyl-3-(3-dimethylaminopropyl)carbodiimide hydrochloride was further added thereto. The obtained mixed solution was stirred at room temperature for 13 hours. Then, the mixed solution was dialyzed in DMSO using a dialysis membrane (molecular weight cutoff: 6,000-8,000) and subsequently dialyzed in water. The intramembrane solution was freeze-dried to obtain 49 mg of a protected glucose-introduced polyethylene glycol-polyaspartic acid block copolymer (yield: 96%).

Next, the protective groups in glucose were deprotected to obtain a glucose-introduced polyethylene glycol-polyaspartic acid block copolymer. Specifically, a solution containing trifluoroacetic acid and water mixed in amounts of 18 mL and 2 mL, respectively, was added to 49 mg of the protected glucose-introduced polyethylene glycol-polyaspartic acid block copolymer, and the mixture was stirred at room temperature for 20 minutes. Then, the reaction solution was kept at 4° C., while the reaction solution was dialyzed in water using a dialysis membrane (molecular weight cutoff: 6,000-8,000). The intramembrane solution was freeze-dried to obtain 40 mg of a glucose-introduced polyethylene glycol-polyaspartic acid block copolymer (yield: 87%).

The obtained copolymer was further labeled with a fluorescent dye DyLight 488. Specifically, 40 mg of the glucose-introduced polyethylene glycol-polyaspartic acid block copolymer was dissolved in 10 mL of dimethyl sulfoxide (DMSO). Also, DyLight 488 N-succinimide ester was dissolved in 5 mL of DMSO, and the solution was added to the glucose-introduced polyethylene glycol-polyaspartic acid block copolymer solution. The mixed solution was stirred at room temperature for 48 hours. Next, the mixed solution was dialyzed in water using a dialysis membrane (molecular weight cutoff: 6,000-8,000). The intramembrane solution was freeze-dried to obtain a yellow solid. The obtained solid was purified using a PD-10 column (GE Healthcare Japan Corp.). The eluate was dialyzed in water using a dialysis membrane (molecular weight cutoff: 6,000-8,000). The intramembrane solution was freeze-dried to obtain 33 mg of a glucose-introduced polyethylene glycol-polyaspartic acid block copolymer fluorescently labeled with DyLight 488.

6-2. Preparation of Glucose-Introduced Antibody

Next, the obtained glucose-introduced polyethylene glycol-polyaspartic acid block copolymer fluorescently labeled with DyLight 488 was conjugated with the antibody to obtain a glucose-introduced antibody. Specifically, the procedures were as follows.

First, the IgG antibody was labeled with Cy5. Specifically, 5 mL of a commercially available Mouse IgG, Isotype Control (Southern Biotechnology Associates Inc.) (5 mg/mL) solution was placed in the upper part of VIVASPIN (molecular weight cutoff: 10,000). Here, after addition of a 0.1 M phosphate buffer (pH 8.4), the operation of carrying out centrifugation at 2000 rpm at 4° C. was repeated to replace the solvent with the 0.1 M phosphate buffer (pH 8.4). Then, the solution was concentrated until the amount thereof became 2.5 mL. Next, 300 μL of N,N-dimethylformamide was added to Cy5 N-succinimide ester (Cy5-NHS ester) (for the labeling of 1 mg protein) (GE Healthcare Japan Corp.), and the mixture was pipetted. A 250 μL aliquot thereof was added to the IgG solution. Then, the mixed solution was gently shaken at room temperature for 4 hours. Then, ultrafiltration was repeated at 2000 rpm at 4° C. using VIVASPIN (molecular weight cutoff: 10,000) so that the IgG solution was purified while the solvent was replaced with D-PBS(−) to obtain 5 mL of a Cy5-labeled IgG (Cy5-IgG) (0.9 mg/mL) solution.

Next, in order to obtain a conjugate of the antibody and the copolymer obtained in the paragraph 6-1, dibenzylcyclooctyne (DBCO) was introduced to the antibody. Specifically, 2 mL of the 0.9 mg/mL Cy5-IgG solution was placed in the upper part of VIVASPIN (molecular weight cutoff: 10,000). After addition of a 0.1 M phosphate buffer (pH 8.4) to the upper part, ultrafiltration was repeated at 2000 rpm at 4° C. to replace the solvent with the 0.1 M phosphate buffer (pH 8.4). Then, the solution was concentrated until the amount thereof became 2 mL. Next, 200 μL of a DMF solution containing 0.41 mg/mL dibenzylcyclooctyne-N-succinimide ester (DBCO-NHS ester) was added to the IgG solution. The mixed solution was gently shaken at room temperature for 4 hours. After the completion of the reaction, the reaction solution was placed in the upper unit of VIVASPIN (molecular weight cutoff: 10,000). After addition of D-PBS(−), ultrafiltration was repeated at 2000 rpm at 4° C. so that the IgG solution was purified while the solvent was replaced with D-PBS(−) to obtain 4 mL of a DBCO-introduced Cy5-labeled IgG (Cy5-labeled DBCO-IgG) solution.

The DBCO was further reacted with the azide group of the copolymer obtained in the paragraph 6-1 to obtain a conjugate of the antibody and the copolymer. Specifically, first, 3.5 mg of the glucose-introduced polyethylene glycol-polyaspartic acid block copolymer fluorescently labeled with DyLight 488 was dissolved in 800 μL of D-PBS(−). The obtained solution was added to 2 mL of the Cy5-labeled DBCO-IgG solution. The mixed solution was left standing at −30° C. for 36 hours and then left standing at 4° C. for 4 hours for gradual thawing. The obtained reaction solution was placed in the upper part of VIVASPIN (molecular weight cutoff: 50,000). D-PBS(−) was added to the upper part, and ultrafiltration was repeated at 2000 rpm at 4° C. so that the IgG solution was purified to obtain 3 mL of a Cy5-labeled IgG (Glc-polymer conjugated IgG) solution (0.11 mg/mL) in which two molecules on average of the polyethylene glycol-polyaspartic acid block copolymer fluorescently labeled with DyLight 488 were conjugated with one molecule of the antibody.

6-3. Pharmacokinetic Evaluation of Antibody

Eight 6-weeks-old Balb/C female mice were fasted for 24 hours. The 8 mice were divided into group A, group B, and a control group (involving 3 mice, 3 mice, and 2 mice, respectively). Glc-polymer conjugated IgG and Cy5-IgG each having a concentration of 750 nM were intravenously injected at a dose of 200 μL to the mice in the groups A and B, respectively. 5 minutes thereafter, 200 μL of a 20% glucose solution was intraperitoneally administered to each mouse. The fluorescence intensity derived from Cy5 in each antibody was equivalent between the groups. The 3 mice in each of the groups A and B were anesthetized with diethyl ether 57 minutes after the antibody administration, and blood collection and organ harvest (brain, liver, kidney, lung, heart, spleen, and thigh muscle) were carried out 3 minutes thereafter. Aside from this, the 2 mice in the control group were also subjected to blood collection and organ harvest. The blood obtained by the blood collection from each mouse was centrifuged at 15,000 rpm at 4° C. to recover a supernatant. The weight of each organ as a whole was first measured for the organs harvested from these 8 mice. Then, half of the brain and approximately 200 mg of the liver were cut out. The unilateral kidney was obtained from each mouse, and the weight thereof was measured. The organ was placed, together with a metal cone, in a tube for Multi-Beads Shocker. 600 μL of 1×Passive Lysis Buffer was added to each of the brain and liver samples of 7 mice other than one mice in the control group; 300 μL of 1×Passive Lysis Buffer was added to each of the spleen, heart, and thigh muscle samples thereof; and 400 μL of 1×Passive Lysis Buffer was added to each of the kidney and lung samples thereof. On the other hand, as for the organ samples of the remaining one mouse (100% control) in the control group, the amount of samples based on the hypothesis that all of the intravenously injected samples would be accumulated in the corresponding organ was calculated, and the Cy5-IgG solution in this calculated amount was added to each organ sample. In addition, 1×Passive Lysis Buffer was added thereto such that the total amount of solutions added was the same as in the other 7 mice. All of the organ samples were each homogenized by repeating the operation at 2000 rpm for 30 seconds 5 times using Multi-Beads Shocker. The cone was removed from the tube of the organ, and each sample was then added at 100 μL/well to a multiplate. The fluorescence intensity was measured at an excitation wavelength of 643 nm and a fluorescence wavelength of 667 nm using a multiplate reader. The sample without the Cy5-IgG solution in the control group was used as a blank, while the fluorescence intensity of the sample supplemented with this solution was defined as 100%. The rate of accumulation of the antibody in each organ was calculated. The obtained rates of accumulation in the organs except for blood were calculated by dividing the rate of accumulation by the weight of the organ (g).

Figure 10:
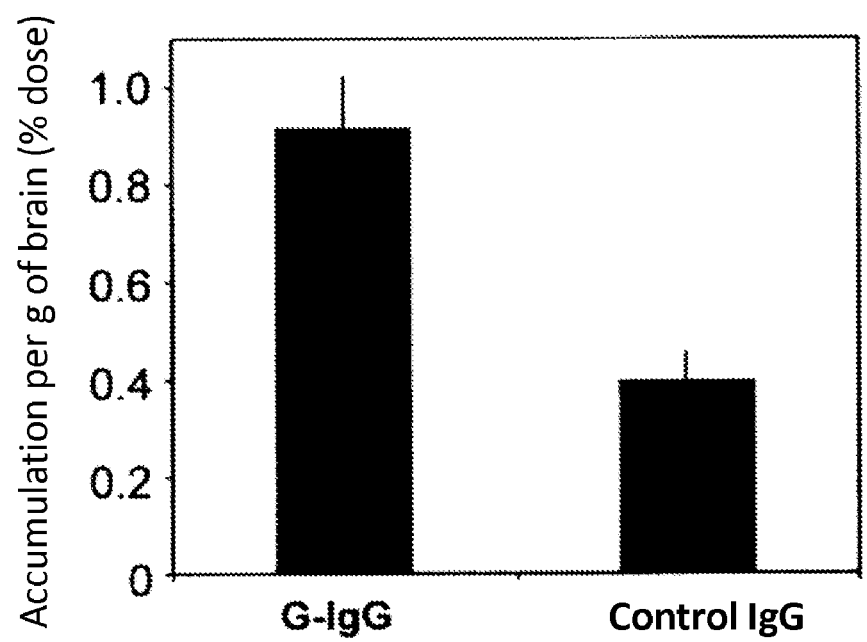
FIG. 10 is a diagram showing the accumulation of an IgG antibody linked via a linker to glucose in the brain. G-IgG represents glucose-linked IgG.

As a result, the antibody conjugated with glucose broke through the blood-brain barrier and arrived at the brain parenchyma. The amount of the antibody arriving at the brain parenchyma was twice the amount of the control (Cy5-IgG) (FIG. 10).

According to Examples 1 to 6, the PIC micelle modified at the outer surface thereof with glucose (Example 2), the PICsome (Example 3), the siRNA micelle (Example 4), the glucose-conjugated polymer (Example 5), and the glucose-conjugated antibody (Example 6), when administered to mice in conjunction with blood glucose control, were significantly accumulated in the brain across the blood-brain barrier. The blood-brain barrier has restrictive material penetration. Thus, many drugs fail to cross the blood-brain barrier and therefore, cannot exhibit the original effects thereof. According to the present invention, even a giant vesicle such as a micelle or PICsome successfully crossed the blood-brain barrier by administering a drug modified with glucose or a drug-incorporated vesicle modified with glucose, in conjunction with blood glucose control. This outcome provides a revolutionary approach of delivering a molecule that has conventionally failed to cross the blood-brain barrier, to the brain. This approach is applicable to various existing or future drugs for brain diseases and diagnostic imaging drugs for the brain and creates a new path to the treatment of brain diseases or the diagnostic imaging of the brain.

Example 7: Delivery to Vascular Endothelial Cell

According to Example 2, the micelle having 25% rate of glucose introduction exhibited more than 3% accumulation in the brain, whereas the micelle having 50% rate of glucose introduction exhibited approximately 1.3% accumulation in the brain. This probably means that the increased rate of glucose introduction reduces the dissociation between the micelle taken up into cerebrovascular endothelial cells and the cerebrovascular endothelial cells. Thus, in this Example, the relationship between the rate of glucose introduction and the accumulation of a micelle in cerebrovascular endothelial cells was confirmed.

First, a micelle having 10% rate of glucose introduction, a micelle having 25% rate of glucose introduction, or a micelle having 50% rate of glucose introduction was prepared by adjusting the amounts of Glc(6)-PEG-P(Asp.) and PEG-P(Asp.) mixed as described in Examples 1-7 and 2.

Each obtained micelle was i.v. administered to mice. 2 days later, tissue sections (thickness: 14 of the brain were prepared by a routine method, and cerebrovascular endothelial cells were stained by immunological fluorescent staining to observe the localization of the fluorescence of the micelle. The cerebrovascular endothelial cells were detected using an anti-PECAM-1 antibody (manufactured by Santa Cruz Biotechnology, Inc., product No: SC18916, Rat monoclonal) as a primary antibody and Alexa 488-conjugated goat anti-rat IgG (H+L) antibody (manufactured by Invitrogen Corp., product No: A11006) as a secondary antibody. Also, the micelle was detected on the basis of the fluorescence of Cy5.

Figure 12:
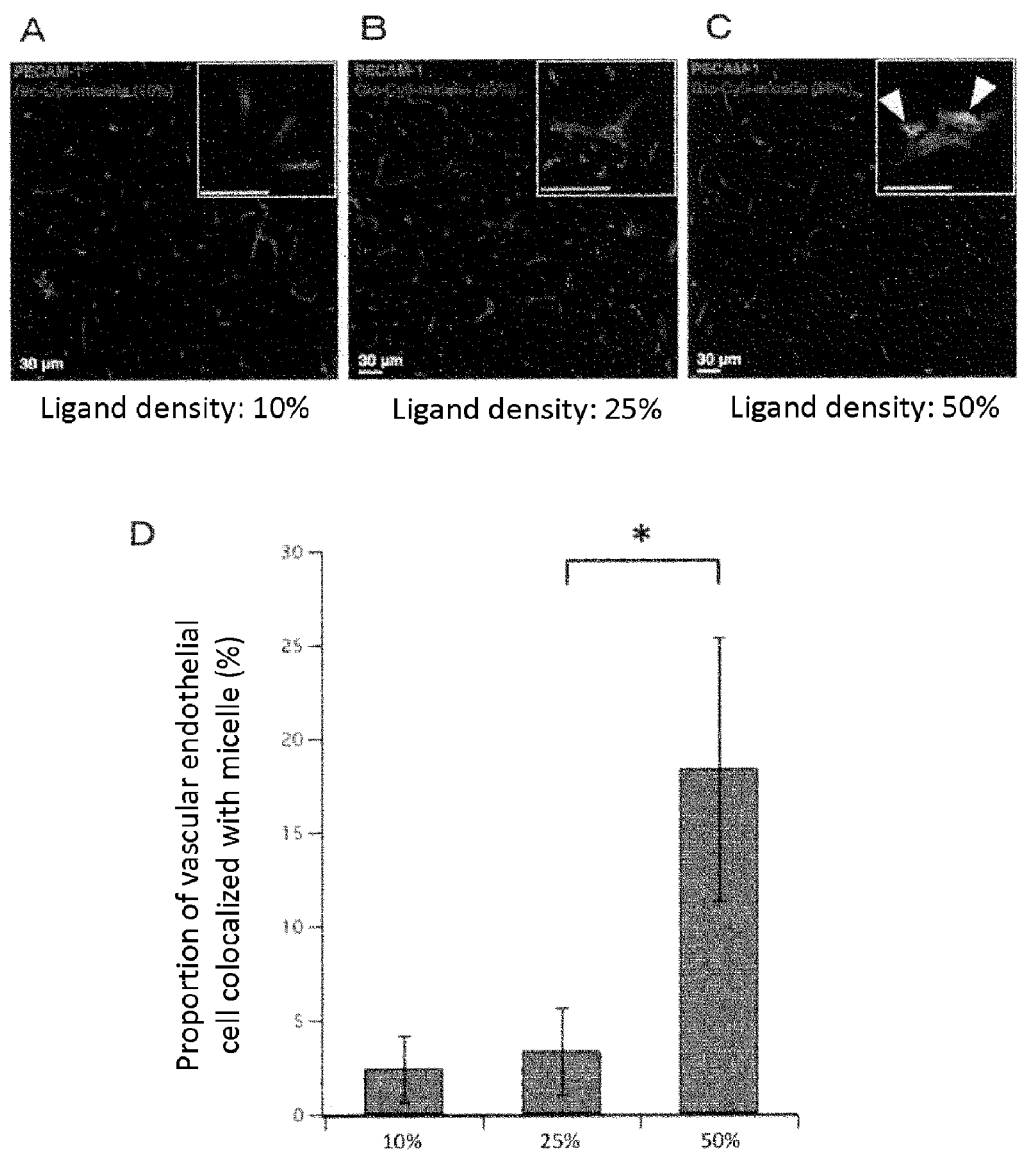
FIG. 12 is a diagram showing that Glc(6)-Cy5-PIC micelles can be partially accumulated in cerebrovascular endothelial cells.

As a result, as shown in FIG. 12A, the colocalization of the cerebrovascular endothelial cells and the micelle was observed particularly frequently in the brain of the mouse given the micelle having 50% rate of glucose introduction (arrowheads in FIG. 12A). As shown in FIG. 12B, the colocalization of the cerebrovascular endothelial cells and the micelle was observed for all of the micelles having 10%, 25%, or 50% rate of glucose introduction, whereas the frequency of localization to the cerebrovascular endothelial cells was significantly increased in the micelle having 50% rate of glucose introduction.

Examples 1 to 6 showed that a vesicle (e.g., a micelle) surface-covered with glucose or a compound (e.g., an antibody) conjugated with glucose can be delivered very efficiently to the brain parenchyma across cerebrovascular endothelial cells. On the other hand, the possibility was suggested that some vesicles or compounds are also accumulated in the cerebrovascular endothelial cells. Particularly, as for the micelle surface-covered with glucose, the increased rate of glucose introduction reduced the amount of micelles escaped from the cerebrovascular endothelial cells to the brain parenchyma, indicating that some of the micelles can also be accumulated in the cerebrovascular endothelial cells. As a result of further confirming this fact in Example 7, the micelle was actually found to be also accumulated in the cerebrovascular endothelial cells. The micelle having 50% rate of glucose introduction was found to be significantly accumulated in the cerebrovascular endothelial cells.

The invention claimed is:

1. A method for administering a drug to a subject, comprising:
  lowering blood glucose level in the subject; and subsequently
  administering a drug to the subject whose blood glucose level has been lowered and increasing blood glucose level in the subject,
  wherein the drug is included in a carrier comprising a conjugate of the formula (I), (II), (III), or (XVI), or a pharmaceutically acceptable salt thereof:

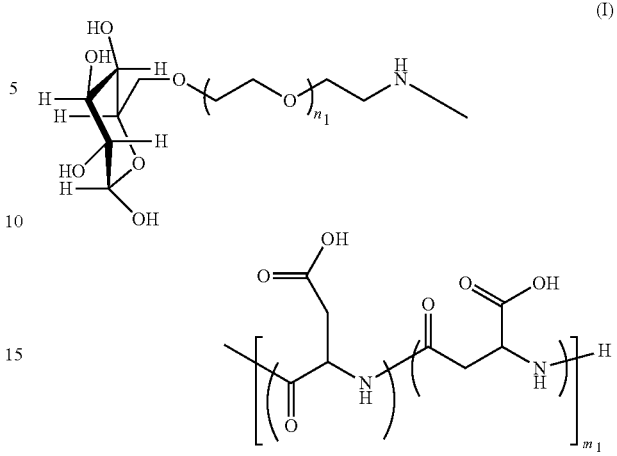

wherein $n_1$ and $m_1$ each represent 5 to 20,000,

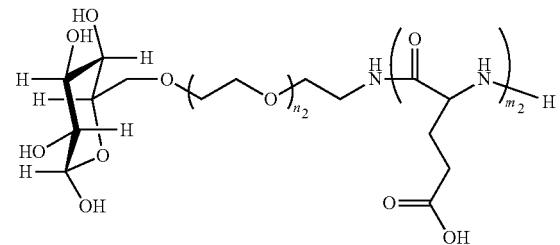

wherein $n_2$ and $m_2$ each represent 5 to 20,000,

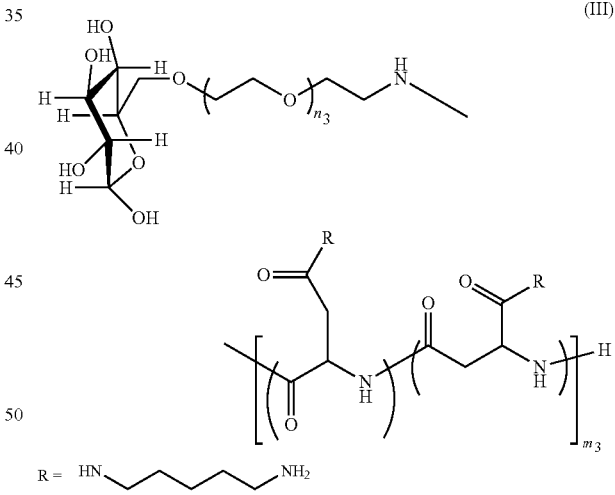

wherein $n_3$ and $m_3$ each represent 5 to 20,000, and

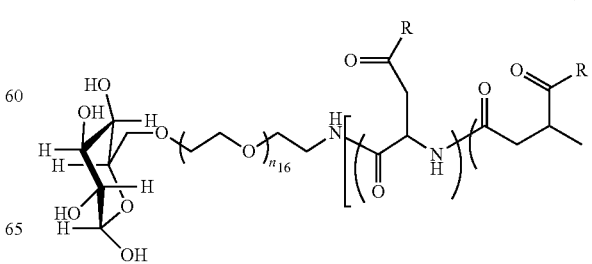

-continued

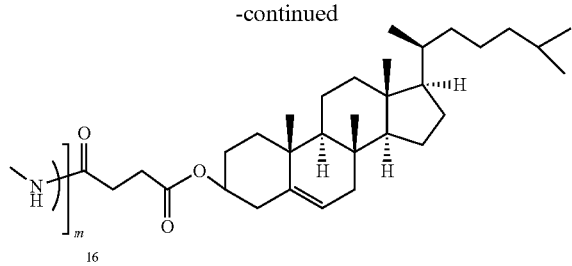

16

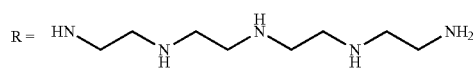

wherein $n_{16}$ represents an integer of 5 to 20,000, and $m_{16}$ represents an integer of 2 to 5,000.

2. The method of claim 1, wherein the drug is administered such that the drug is permeating across a blood-brain barrier in the subject.

3. The method of claim 1, wherein the drug is administered such that the drug is permeating across at least one of a blood-nerve barrier, a blood-retina barrier, and a blood-cerebrospinal fluid barrier in the subject.

4. The method of claim 1, wherein the carrier is a vesicle, and 10 to 40% by mol of a polymer constituting the vesicle is modified with glucose.

5. The method of claim 1, wherein the carrier is a vesicle, and 40 to 100% by mol of a polymer constituting the vesicle is modified with glucose.

6. The method of claim 1, wherein the carrier is a vesicle having a diameter of 400 nm or smaller.

7. The method of claim 1, wherein the drug is at least one selected from the group consisting of a biologically active substance, an antibody, a nucleic acid, a biocompatible fluorescent dye, and a contrast medium.

8. The method of claim 1, wherein the conjugate is capable of forming a vesicle such that the glucose in the formula (I), (II), (III), or (IV) is exposed on a surface of the vesicle.

9. The method of claim 1, wherein the drug is delivered to at least one of the brain and cerebrovascular endothelial cells in the subject.

10. The method of claim 1, wherein the blood glucose level is increased by administering glucose to the subject.

11. The method of claim 10, wherein the drug is administered concurrently with or before the administration of the glucose.

12. The method of claim 11, wherein the drug is administered in the form of an intravenous infusion for 10 minutes or longer.

13. The method of claim 1, wherein the subject is kept to have low blood glucose level or hypoglycemia for less than 48 hours before the administering of the drug.

14. The method of claim 1, wherein the carrier comprise a conjugate of the formula (I):

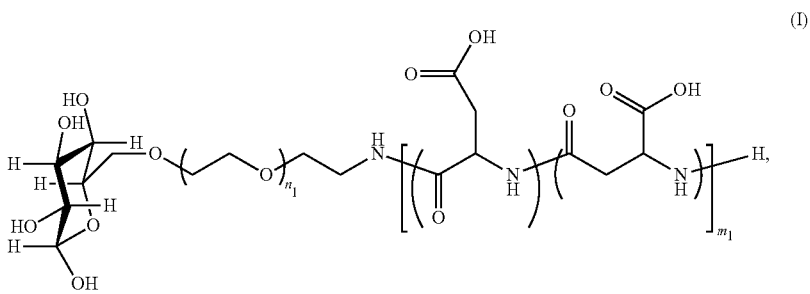

(I)

wherein $n_1$ and $m_1$ each represent 5 to 20,000.

15. The method of claim 1, wherein the blood glucose level is increased prior to the administrating of the drug such that the drug is administered while the blood glucose level is increased.

16. The method of claim 1, wherein the blood glucose level is increased within six hours after the administrating of the drug.

17. The method of claim 1, wherein the drug is administered such that the drug is accumulated to endothelial cells present in at least one of a blood-brain barrier, a blood-nerve barrier, a blood-retina barrier, and a blood-cerebrospinal fluid barrier.

18. The method of claim 1, wherein the blood glucose level is increased less than 1 hour prior to the administering of the drug.

19. A method of delivering a drug to at least one of a brain and cerebrovascular endothelial cells in a subject, comprising:
lowering blood glucose level in the subject; and subsequently
administering a drug to the subject whose blood glucose level has been lowered and increasing blood glucose level in the subject,
wherein the drug is included in a carrier comprising a conjugate of the formula (I), (II), (III), or (XVI), or a pharmaceutically acceptable salt thereof:

(I)

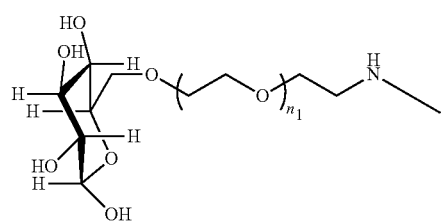

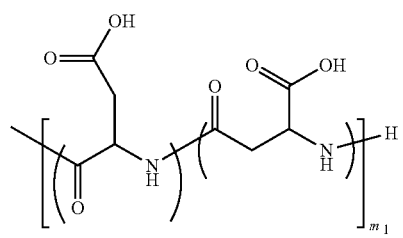

wherein $n_1$ and $m_1$ each represent 5 to 20,000, (II)

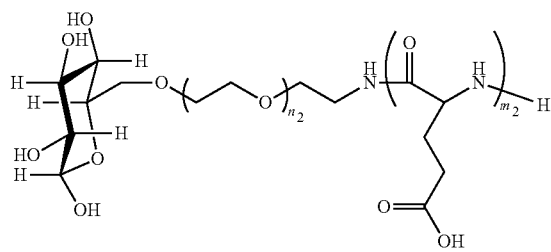

wherein $n_2$ and $m_2$ each represent 5 to 20,000, (III)

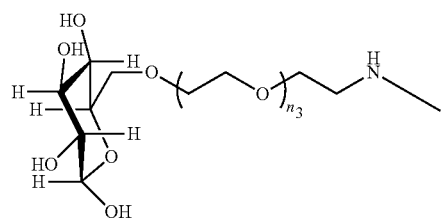

-continued

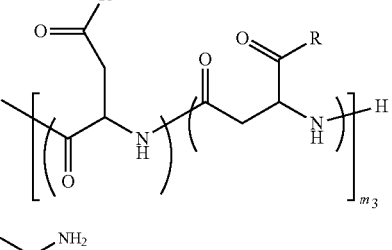

wherein $n_3$ and $m_3$ each represent 5 to 20,000, and (XVI)

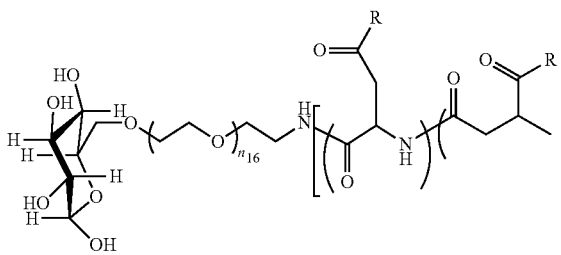

wherein $n_{16}$ represents an integer of 5 to 20,000, and $m_{16}$ represents an integer of 2 to 5,000.

20. The method of claim 19, wherein the subject is kept to have low blood glucose level or hypoglycemia for less than 48 hours before the administering of the drug.

21. The method of claim 19, wherein the carrier comprise a conjugate of the formula (I):

(I)

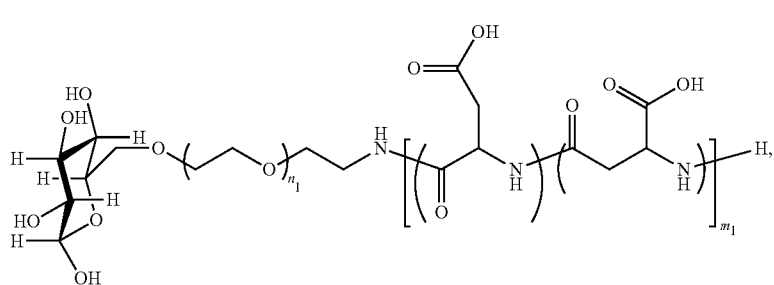

wherein $n_1$ and $m_1$ each represent 5 to 20,000.

22. The method of claim 19, wherein the blood glucose level is increased prior to the administrating of the drug such that the drug is administered while the blood glucose level is increased.

23. The method of claim 19, wherein the blood glucose level is increased within six hours after the administrating of the drug.

24. A method for administering a drug included in a vesicle comprising a conjugate of formula (I) to a subject, comprising:

lowering blood glucose level in a subject;
administering the drug included in the vesicle to the subject whose blood glucose level has been lowered; and
increasing blood glucose level in the subject,

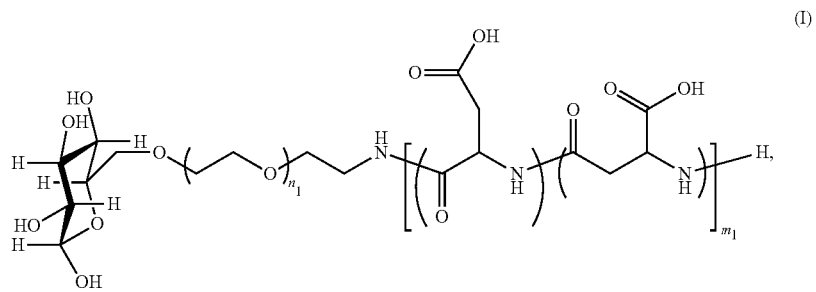

(I)

wherein $n_1$ and $m_1$ each represent 5 to 20,000.

* * * * *